(12) United States Patent
Pattabiraman et al.

(10) Patent No.: US 10,398,672 B2
(45) Date of Patent: Sep. 3, 2019

(54) METHODS AND COMPOSITIONS FOR TARGETING CANCER STEM CELLS

(71) Applicant: Whitehead Institute for Biomedical Research, Cambridge, MA (US)

(72) Inventors: Diwakar Pattabiraman, Cambridge, MA (US); Brian Bierie, Cambridge, MA (US); Wai Leong Tam, Singapore (SG); Robert A. Weinberg, Brookline, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 15/307,657

(22) PCT Filed: Apr. 29, 2015

(86) PCT No.: PCT/US2015/028239
§ 371 (c)(1),
(2) Date: Oct. 28, 2016

(87) PCT Pub. No.: WO2015/168255
PCT Pub. Date: Nov. 5, 2015

(65) Prior Publication Data
US 2017/0049745 A1    Feb. 23, 2017

Related U.S. Application Data

(60) Provisional application No. 61/986,082, filed on Apr. 29, 2014.

(51) Int. Cl.
| | |
|---|---|
| *A61K 31/352* | (2006.01) |
| *A61K 31/35* | (2006.01) |
| *G01N 33/50* | (2006.01) |
| *A61K 31/704* | (2006.01) |
| *C12N 5/00* | (2006.01) |
| *C12N 5/095* | (2010.01) |

(52) U.S. Cl.
CPC .......... *A61K 31/352* (2013.01); *A61K 31/704* (2013.01); *C12N 5/0093* (2013.01); *C12N 5/0695* (2013.01); *G01N 33/5011* (2013.01); *G01N 33/5041* (2013.01); *G01N 33/5073* (2013.01); *C12N 2501/727* (2013.01); *C12N 2506/30* (2013.01); *G01N 2333/91205* (2013.01); *G01N 2800/52* (2013.01); *Y02A 50/471* (2018.01)

(58) Field of Classification Search
CPC .............................. A61K 31/352; A61K 31/35
USPC ...................................................... 424/1.65
See application file for complete search history.

(56) References Cited

U.S. PATENT DOCUMENTS

| | | | |
|---|---|---|---|
| 3,854,480 | A | 12/1974 | Zaffaroni |
| 4,452,775 | A | 6/1984 | Kent |
| 4,675,189 | A | 6/1987 | Kent et al. |
| 5,075,109 | A | 12/1991 | Tice et al. |
| 5,133,974 | A | 7/1992 | Paradissis et al. |
| 5,211,657 | A | 5/1993 | Yamada et al. |
| 5,223,409 | A | 6/1993 | Ladner et al. |
| 5,407,686 | A | 4/1995 | Patel et al. |
| 5,736,152 | A | 4/1998 | Dunn |
| 6,124,133 | A | 9/2000 | Taylor et al. |
| 2002/0042079 | A1 | 4/2002 | Simon et al. |
| 2004/0101936 | A1 | 5/2004 | Endo et al. |
| 2004/0110728 | A1 | 6/2004 | MacDonald et al. |
| 2005/0182006 | A1 | 8/2005 | McSwiggen et al. |
| 2005/0209310 | A1 | 9/2005 | Chaplin et al. |
| 2006/0040980 | A1 | 2/2006 | Lind et al. |
| 2006/0141549 | A1 | 6/2006 | Mahajan et al. |
| 2007/0105133 | A1 | 5/2007 | Clarke et al. |
| 2007/0172818 | A1 | 7/2007 | Fisher et al. |
| 2008/0033189 | A1 | 2/2008 | Naidu |
| 2008/0267957 | A1 | 10/2008 | Arnold et al. |
| 2009/0054312 | A1 | 2/2009 | Wolf et al. |
| 2009/0203713 | A1 | 8/2009 | Beachy et al. |
| 2010/0069458 | A1 | 3/2010 | Atadja et al. |
| 2010/0162416 | A1 | 6/2010 | Krtolica et al. |
| 2010/0255999 | A1 | 10/2010 | Mitsiades et al. |
| 2011/0191868 | A1 | 8/2011 | Gupta et al. |
| 2012/0159655 | A1 | 6/2012 | Lorens et al. |
| 2014/0294729 | A1 | 10/2014 | Gupta et al. |

(Continued)

FOREIGN PATENT DOCUMENTS

| | | |
|---|---|---|
| WO | WO 93/018778 A1 | 9/1993 |
| WO | WO 94/029328 A1 | 12/1994 |

(Continued)

OTHER PUBLICATIONS

Al-Hajj et al., Prospective identification of tumorigenic breast cancer cells. Proc Natl Acad Sci U S A. Apr 1, 2003;100(7):3983-8. Epub Mar. 10, 2003.

Allen et al., Synthesis of C-2 functionalised 1,6,8-trioxadispiro[4.1.5.3]pentadec-13-enes. J. Chem. Soc., Perkin Trans. 1998;1:2403-2412.

Andarawewa et al., Ionizing radiation predisposes nonmalignant human mammary epithelial cells to undergo transforming growth factor beta induced epithelial to mesenchymal transition. Cancer Res. Sep. 15, 2007;67(18):8662-70.

(Continued)

*Primary Examiner* — Yan Xiao
(74) *Attorney, Agent, or Firm* — Wolf, Greenfield & Sacks, P.C.

(57) ABSTRACT

Aspects of the disclosure relate to methods that involve activating the Protein Kinase A (PKA) pathway to induce cancer stem cells (CSCs) to undergo a mesenchymal to epithelial transition. Methods provided herein are useful, in some embodiments, because they render CSCs amenable to treatment with conventional cancer therapies. In some embodiments, methods are provided that involve assaying PKA pathway activity to identify compounds that selectively target CSCs.

6 Claims, 23 Drawing Sheets

(56) References Cited

U.S. PATENT DOCUMENTS

| | | | |
|---|---|---|---|
| 2015/0157584 A1* | 6/2015 | Guan | A61K 31/15 424/172.1 |
| 2016/0017292 A1 | 1/2016 | Tam et al. | |

FOREIGN PATENT DOCUMENTS

| | | |
|---|---|---|
| WO | WO 95/024929 | 9/1995 |
| WO | WO 99/005156 A1 | 2/1999 |
| WO | WO 2002/102805 A1 | 12/2002 |
| WO | WO 2003/035661 A1 | 5/2003 |
| WO | WO 2003/045932 A1 | 6/2003 |
| WO | WO 2003/048166 A1 | 6/2003 |
| WO | WO 2004/000859 A2 | 12/2003 |
| WO | WO 2005/056549 A1 | 6/2005 |
| WO | WO 2006/004795 A2 | 1/2006 |
| WO | WO 2006/101925 A2 | 9/2006 |
| WO | WO 2007/005611 A2 | 1/2007 |
| WO | WO 2007/024971 A2 | 3/2007 |
| WO | WO 2007/035744 A1 | 3/2007 |
| WO | WO 2008/051493 A2 | 5/2008 |
| WO | WO 2008/122038 A1 | 10/2008 |
| WO | WO 2009/126310 | 10/2009 |
| WO | WO 2013/119923 A1 | 8/2013 |
| WO | WO 2013119923 * | 8/2013 |

OTHER PUBLICATIONS

Baba et al., PKA-dependent regulation of the histone lysine demethylase complex PHF2-ARID5B. Nat Cell Biol. Jun. 2011;13(6):668-75. doi:10.1038/ncb2228. Epub May 1, 2011.

Bao et al., Glioma stem cells promote radioresistance by preferential activation of the DNA damage response. Nature. Dec. 7, 2006;444(7120):756-60. Epub Oct. 18, 2006.

Carbone et al., Multistep and multifactorial carcinogenesis: when does a contributing factor become a carcinogen? Semin Cancer Biol. Dec. 2004;14(6):399-405.

Carell et al., A Novel Procedure for the Synthesis of Libraries Containing Small Organic Molecules. Angew. Chem. Int. Ed. Engl. 1994;33: 2059-2061. doi:10.1002/anie.199420591.

Carell et al., A Solution-Phase Screening Procedure for the Isolation of Active Compounds from a Library of Molecules. Angew. Chem. Int. Ed. Engl. 1994;33: 2061-2064.

Carpenter et al., Motility induction in breast carcinoma by mammary epithelial laminin 332 (laminin 5). Mol Cancer Res. Apr. 2009;7(4):462-75. doi: 10.1158/1541-7786.MCR-08-0148. Epub Apr. 7, 2009.

Carter et al., Antisense technology for cancer therapy: does it make sense? Br J Cancer. May 1993;67(5):869-76.

Cheng et al., Phosphorylation and activation of cAMP-dependent protein kinase by phosphoinositide-dependent protein kinase. Proc Natl Acad Sci U S A. Aug. 18, 1998;95(17):9849-54.

Cho et al., An unnatural biopolymer. Science. Sep. 3, 1993;261(5126):1303-5.

Choung et al., Chemical modification of siRNAs to improve serum stability without loss of efficacy. Biochem Biophys Res Commun. Apr. 14, 2006;342(3):919-27.

Cifone et al., Correlation of patterns of anchorage-independent growth with in vivo behavior of cells from a murine fibrosarcoma. Proc Natl Acad Sci U S A. Feb. 1980;77(2):1039-43.

Cull et al., Screening for receptor ligands using large libraries of peptides linked to the C terminus of the lac repressor. Proc Natl Acad Sci U S A. Mar. 1, 1992;89(5):1865-9.

Cwirla et al., Peptides on phage: a vast library of peptides for identifying ligands. Proc Natl Acad Sci U S A. Aug. 1990;87(16):6378-82.

Czarnik, Encoding methods for combinatorial chemistry. Curr Opin Chem Biol. Jun. 1997;1(1):60-6.

Dasgupta et al., Nicotine induces cell proliferation, invasion and epithelial-mesenchymal transition in a variety of human cancer cell lines. Int J Cancer. Jan. 1, 2009;124(1):36-45. doi: 10.1002/ijc.23894.

De Paula et al., Hydrophobization and bioconjugation for enhanced siRNA delivery and targeting. RNA. Apr. 2007;13(4):431-56.

Dean et al., Tumour stem cells and drug resistance. Nat Rev Cancer. Apr. 2005;5(4):275-84.

Devlin et al., Random peptide libraries: a source of specific protein binding molecules. Science. Jul. 27, 1990;249(4967):404-6.

Dewitt et al., "Diversomers": an approach to nonpeptide, nonoligomeric chemical diversity. Proc Natl Acad Sci U S A. Aug. 1, 1993;90(15):6909-13.

Diehn et al., Cancer stem cells and radiotherapy: new insights into tumor radioresistance. J Natl Cancer Inst. Dec. 20, 2006;98(24):1755-7.

Docherty et al., TGF-beta1-induced EMT can occur independently of its proapoptotic effects and is aided by EGF receptor activation. Am J Physiol Renal Physiol. May 2006;290(5):F1202-12. Epub Dec 20, 2005.

Dontu et al., In vitro propagation and transcriptional profiling of human mammary stem/progenitor cells. Genes Dev. May 15, 2003;17(10):1253-70.

Dosaka-Akita et al., Abnormal p53 expression in human lung cancer is associated with histologic subtypes and patient smoking history. Am J Clin Pathol. Nov. 1994;102(5):660-4.

Drinyaev et al., Antitumor effect of avermectins. Eur J Pharmacol. Oct. 6, 2004;501(1-3):19-23.

Elenbaas et al., Human breast cancer cells generated by oncogenic transformation of primary mammary epithelial cells. Genes Dev. Jan. 1, 2001;15(1):50-65.

Erb et al., Recursive deconvolution of combinatorial chemical libraries. Proc Natl Acad Sci U S A. Nov. 22, 1994;91(24):11422-6.

Felici et al., Selection of antibody ligands from a large library of oligopeptides expressed on a multivalent exposition vector. J Mol Biol. Nov. 20, 1991;222(2):301-10.

Feng et al., Neoplastic reversion accomplished by high efficiency adenoviral-mediated delivery of an anti-ras ribozyme. Cancer Res. May 15, 1995;55(10):2024-8.

Fernandes, Technological advances in high-throughput screening. Curr Opin Chem Biol. Oct. 1998;2(5):597-603.

Fillmore et al., Human breast cancer cell lines contain stem-like cells that self-renew, give rise to phenotypically diverse progeny and survive chemotherapy. Breast Cancer Res. 2008;10(2):R25. doi: 10.1186/bcr1982.

Finn et al., Dasatinib, an orally active small molecule inhibitor of both the src and abl kinases, selectively inhibits growth of basal-type/"triple-negative" breast cancer cell lines growing in vitro. Breast Cancer Res Treat. Nov. 2007;105(3):319-26.

Fodor et al., Multiplexed biochemical assays with biological chips. Nature. Aug. 5, 1993;364(6437):555-6.

French et al., Antitumor activity of sphingosine kinase inhibitors. J Pharmacol Exp Ther. Aug. 2006;318(2):596-603.

Frisch et al., Disruption of epithelial cell-matrix interactions induces apoptosis. J Cell Biol. Feb. 1994;124(4):619-26.

Gallop et al., Applications of combinatorial technologies to drug discovery. 1. Background and peptide combinatorial libraries. J Med Chem. Apr. 29, 1994;37(9):1233-51.

Grande et al., Transforming growth factor-beta and epidermal growth factor synergistically stimulate epithelial to mesenchymal transition (EMT) through a MEK-dependent mechanism in primary cultured pig thyrocytes. J Cell Sci. Nov. 15, 2002;115(Pt 22):4227-36.

Gregory et al., The miR-200 family and miR-205 regulate epithelial to mesenchymal transition by targeting ZEB1 and SIP1. Nat Cell Biol. May 2008;10(5):593-601. doi: 10.1038/ncb1722. Epub Mar. 30, 2008.

Gu et al., Measuring cell motility using quantum dot probes. Methods Mol Biol. 2007;374:125-31.

Gupta et al., Identification of selective inhibitors of cancer stem cells by high-throughput screening. Cell. Aug. 21, 2009;138(4):645-59. Epub Aug. 13, 2009.

Gura, Systems for identifying new drugs are often faulty. Science. Nov. 7, 1997;278(5340):1041-2.

Hahn et al., Creation of human tumour cells with defined genetic elements. Nature. Jul. 29, 1999;400(6743):464-8.

(56) References Cited

OTHER PUBLICATIONS

Herschlag et al., An RNA chaperone activity of non-specific RNA binding proteins in hammerhead ribozyme catalysis. EMBO J. Jun. 15, 1994;13(12):2913-24. Erratum in: EMBO J Aug. 15, 1994;13(16):3926.
Hollier et al., The epithelial-to-mesenchymal transition and cancer stem cells: a coalition against cancer therapies. J Mammary Gland Biol Neoplasia. Mar. 2009;14(1):29-43. Epub Feb. 26, 2009.
Houghten et al., The use of synthetic peptide combinatorial libraries for the identification of bioactive peptides. Biotechniques. Sep. 1992;13(3):412-21.
Hurt et al., CD44+ CD24(−) prostate cells are early cancer progenitor/stem cells that provide a model for patients with poor prognosis. Br J Cancer. Feb. 26, 2008;98(4):756-65. Epub Feb. 12, 2008.
Iwase et al., Synthesis and properties of modified siRNA having amide-linked oligoribonucleosides at their 3' overhang regions. Nucleic Acids Symp Ser (Oxf). 2006;(50):175-6.
Jankowsky et al., Oligonucleotide facilitators may inhibit or activate a hammerhead ribozyme. Nucleic Acids Res. Feb. 1, 1996;24(3):423-9.
Jia et al., Activation of protein kinase A and exchange protein directly activated by cAMP promotes adipocyte differentiation of human mesenchymal stem cells. PLoS One. 2012;7(3):e34114. doi:10.1371/journal.pone.0034114. Epub Mar. 27, 2012.
Jiang et al., Role of Wnt/beta-catenin signaling pathway in epithelial-mesenchymal transition of human prostate cancer induced by hypoxia-inducible factor-1alpha. Int J Urol. Nov. 2007;14(11):1034-9.
Jinushi et al., Milk fat globule EGF-8 promotes melanoma progression through coordinated Akt and twist signaling in the tumor microenvironment. Cancer Res. Nov. 1, 2008;68(21):8889-98. doi: 10.1158/0008-5472.CAN-08-2147.
Jones et al., Tagging ribozyme reaction sites to follow trans-splicing in mammalian cells. Nat Med. Jun. 1996;2(6):643-8.
Kelland, Of mice and men: values and liabilities of the athymic nude mouse model in anticancer drug development. Eur J Cancer. Apr. 2004;40(6):827-36.
Kerbel, Human tumor xenografts as predictive preclinical models for anticancer drug activity in humans: better than commonly perceived—but they can be improved. Cancer Biol Ther. Jul.-Aug. 2003;2(4 Suppl 1):S134-9.
Kim et al., Occurrence of ionophore antibiotics in water and sediments of a mixed-landscape watershed. Water Res. Jul. 2006;40(13):2549-60.
Klein et al., Targeting the EGFR and the PKB pathway in cancer. Curr Opin Cell Biol. Apr. 2009;21(2):185-93. doi: 10.1016/j.ceb.2008.12.006. Epub Feb. 11, 2009.
Krawetz et al., Wnt6 induces the specification and epithelialization of F9 embryonal carcinoma cells to primitive endoderm. Cell Signal. Mar. 2008;20(3):506-17. Epub Nov. 7, 2007.
Kunz-Schughart et al., The use of 3-D cultures for high-throughput screening: the multicellular spheroid model. J Biomol Screen. Jun. 2004;9(4):273-85.
Lam et al., A new type of synthetic peptide library for identifying ligand-binding activity. Nature. Nov. 7, 1991;354:82-84. doi:10.1038/354082a0.
Lam, Application of combinatorial library methods in cancer research and drug discovery. Anticancer Drug Des. Apr. 1997;12(3):145-67.
Lamouille et al., Molecular mechanisms of epithelial-mesenchymal transition. Nat Rev Mol Cell Biol. Mar. 2014;15(3):178-96. doi: 10.1038/nrm3758.
Lange et al., In vitro and in vivo effects of synthetic ribozymes targeted against BCR/ABL mRNA. Leukemia. Nov. 1993;7(11):1786-94.
Lee et al., The epithelial-mesenchymal transition: new insights in signaling, development, and disease. J Cell Biol. Mar. 27, 2006;172(7):973-81.
Lester et al., uPAR induces epithelial-mesenchymal transition in hypoxic breast cancer cells. J Cell Biol. Jul. 30, 2007;178(3):425-36.
Lewin et al., Ribozyme rescue of photoreceptor cells in a transgenic rat model of autosomal dominant retinitis pigmentosa. Nat Med. Aug. 1998;4(8):967-71. Erratum in: Nat Med Sep. 1998;4(9):1081.
Li et al., Identification of pancreatic cancer stem cells. Cancer Res. Feb. 1, 2007;67(3):1030-7.
Lim et al., Epigenetic changes induced by reactive oxygen species in hepatocellular carcinoma: methylation of the E-cadherin promoter. Gastroenterology. Dec. 2008;135(6):2128-40, 2140.e1-8. doi: 10.1053/j.gastro.2008.07.027. Epub Jul. 31, 2008.
Lim et al., FTY720 analogues as sphingosine kinase 1 inhibitors: enzyme inhibition kinetics, allosterism, proteasomal degradation, and actin rearrangement in MCF-7 breast cancer cells. J Biol Chem. May 27, 2011;286(21):18633-40. doi: 10.1074/jbc.M111.220756.
Littlewood et al., A modified oestrogen receptor ligand-binding domain as an improved switch for the regulation of heterologous proteins. Nucleic Acids Res. May 25, 1995;23(10):1686-90.
Liu et al., Activated androgen receptor downregulates E-cadherin gene expression and promotes tumor metastasis. Mol Cell Biol. Dec. 2008;28(23):7096-108. doi: 10.1128/MCB.00449-08. Epub Sep. 15, 2008.
Liu et al., Analysis of gene expression and chemoresistance of CD133+ cancer stem cells in glioblastoma. Mol Cancer. Dec. 2, 2006;5:67.
Liu et al., The prognostic role of a gene signature from tumorigenic breast-cancer cells. N. Engl J Med. Jan. 18, 2007;356(3):217-26.
Lo et al., Epidermal growth factor receptor cooperates with signal transducer and activator of transcription 3 to induce epithelial-mesenchymal transition in cancer cells via up-regulation of TWIST gene expression. Cancer Res. Oct. 1, 2007;67(19):9066-76.
Mani et al., The epithelial-mesenchymal transition generates cells with properties of stem cells. Cell. May 16, 2008;133(4):704-15.
Manotham et al., Transdifferentiation of cultured tubular cells induced by hypoxia. Kidney Int. Mar. 2004;65(3):871-80.
Mitani et al., Salinomycin: a new monovalent cation ionophore. Biochem Biophys Res Commun. Oct. 27, 1975;66(4):1231-6.
Molina-Oritiz et al., Functional characterization of Snail2 mediated E-cadherin repression. Int Workshop Cancer Stem Cells. $2^{nd}$ ed. Dec. 2, 2007;65.
Morel et al., Generation of breast cancer stem cells through epithelial-mesenchymal transition. PLoS One. Aug. 6, 2008;3(8):e2888.
Moustakas et al., Signaling networks guiding epithelial-mesenchymal transitions during embryogenesis and cancer progression. Cancer Sci. Oct. 2007;98(10):1512-20. Epub Jul. 23, 2007.
Mushinski et al., Inhibition of tumor cell motility by the interferon-inducible GTPase MxA. J Biol Chem. May 29, 2009;284(22):15206-14. doi: 10.1074/jbc.M806324200. Epub Mar. 18, 2009.
Nakamura et al., Polarized hydroxyapatite promotes spread and motility of osteoblastic cells. J Biomed Mater Res A. Feb. 2010;92(2):783-90. doi: 10.1002/jbm.a.32404.
O'Brien et al., A human colon cancer cell capable of initiating tumour growth in immunodeficient mice. Nature. Jan. 4, 2007;445(7123):106-10. Epub Nov. 19, 2006.
Ohkawa et al., Multiple site-specific cleavage of HIV RNA by transcribed ribozymes from shotgun-type trimming plasmid. Nucleic Acids Symp Ser. 1993;(29):121-2.
Onder et al., Loss of E-cadherin promotes metastasis via multiple downstream transcriptional pathways. Cancer Res. May 15, 2008;68(10):3645-54.
Pagliarini et al., A genetic screen in Drosophila for metastatic behavior. Science. Nov. 14, 2003;302(5648):1227-31. Epub Oct. 9, 2003.
Pérez-Caro et al., Killing time for cancer stem cells (CSC): discovery and development of selective CSC inhibitors. Curr Med Chem. 2006;13(15):1719-25.
Phillips et al., The response of CD24(−/low)/CD44+ breast cancer-initiating cells to radiation. J Natl Cancer Inst. Dec. 20, 2006;98(24):1777-85.
Pyne et al., Sphingosine kinase inhibitors and cancer: seeking the golden sword of Hercules. Cancer Res. Nov. 1, 2011;71(21):6576-82. doi:10.1158/0008-5472.CAN-11-2364.
Qin et al., The mammalian Scribble polarity protein regulates epithelial cell adhesion and migration through E-cadherin. J Cell Biol. Dec. 19, 2005;171(6):1061-71. Epub Dec. 12, 2005.

(56) References Cited

OTHER PUBLICATIONS

Quattrone et al., Reversion of the invasive phenotype of transformed human fibroblasts by anti-messenger oligonucleotide inhibition of urokinase receptor gene expression. Cancer Res. Jan. 1, 1995;55(1):90-5.

Ricci-Vitiani et al., Identification and expansion of human colon-cancer-initiating cells. Nature. Jan. 4, 2007;445(7123):111-5. Epub Nov. 19, 2006.

Sakai et al., Inducible expression of p57KIP2 inhibits glioma cell motility and invasion. J Neurooncol. Jul. 2004;68(3):217-23.

Sato et al., Targeted disruption of TGF-beta1/Smad3 signaling protects against renal tubulointerstitial fibrosis induced by unilateral ureteral obstruction. J Clin Invest. Nov. 2003;112(10):1486-94.

Sawhney et al., Bioerodible hydrogels based on photopolymerized poly(ethylene glycol)-co-poly(.alpha.-hydroxy acid) diacrylate macromers. Macromolecules. 1993;26(4):581-587.

Scott et al., Searching for peptide ligands with an epitope library. Science. Jul. 27, 1990;249(4967):386-90.

Shipitsin et al., Molecular definition of breast tumor heterogeneity. Cancer Cell. Mar. 2007;11(3):259-73.

Singh et al., Identification of human brain tumour initiating cells. Nature. Nov. 18, 2004;432(7015):396-401.

Sledge et al., Phase III trial of doxorubicin, paclitaxel, and the combination of doxorubicin and paclitaxel as front-line chemotherapy for metastatic breast cancer: an intergroup trial (E1193). J Clin Oncol. Feb. 15, 2003;21(4):588-92.

Sobrado et al., New insight in the regulation of E-cadherin and EMT: the role of BHLH factors E2-A2 and E2-2B. Int Workshop Cancer Stem Cells. $2^{nd}$ ed. Dec. 2, 2007;88.

Stewart et al., Lentivirus-delivered stable gene silencing by RNAi in primary cells. RNA. Apr. 2003;9(4):493-501.

Stingl et al., Purification and unique properties of mammary epithelial stem cells. Nature. Feb. 23, 2006;439(7079):993-7. Epub Jan. 4, 2006.

Sullenger et al., Ribozyme-mediated repair of defective mRNA by targeted, trans-splicing. Nature. Oct. 13, 1994;371(6498):619-22.

Sundberg, High-throughput and ultra-high-throughput screening: solution-and cell-based approaches. Curr Opin Biotechnol. Feb. 2000;11(1):47-53.

Szotek et al., Ovarian cancer side population defines cells with stem cell-like characteristics and Mullerian Inhibiting Substance responsiveness. Proc Natl Acad Sci U S A. Jul. 25, 2006;103(30):11154-9. Epub Jul. 18, 2006.

Tam et al., Protein kinase C α is a central signaling node and therapeutic target for breast cancer stem cells. Cancer Cell. Sep. 9, 2013;24(3):347-64. doi: 10.1016/j.ccr.2013.08.005.

Tang et al., C3a mediates epithelial-to-mesenchymal transition in proteinuric nephropathy. J Am Soc Nephrol. Mar. 2009;20(3):593-603. doi: 10.1681/ASN.2008040434. Epub Jan. 21, 2009.

Tang et al., Cancer stem cell: target for anti-cancer therapy. FASEB J. Dec. 2007;21(14):3777-85. Epub Jul. 11, 2007.

Tarin et al., The fallacy of epithelial mesenchymal transition in neoplasia. Cancer Res. Jul. 15, 2005;65(14):5996-6000; discussion 6000-1.

Templeton et al., Cancer stem cells: progress and challenges in lung cancer. Stem Cell Investigation. 2014;1:9.

Thiery, Epithelial-mesenchymal transitions in tumour progression. Nat Rev Cancer. Jun. 2002;2(6):442-54.

Thomson et al., Kinase switching in mesenchymal-like non-small cell lung cancer lines contributes to EGFR inhibitor resistance through pathway redundancy. Clin Exp Metastasis. 2008;25(8):843-54. doi: 10.1007/s10585-008-9200-4.

Tonelli et al., FTY720 and (S)-FTY720 vinylphosphonate inhibit sphingosine kinase 1 and promote its proteasomal degradation in human pulmonary artery smooth muscle, breast cancer and androgen-independent prostate cancer cells. Cell Signal. Oct. 2010;22(10):1536-42. doi: 10.1016/j.cellsig.2010.05.022.

Valera et al., Expression of GLUT-2 antisense RNA in beta cells of transgenic mice leads to diabetes. J Biol Chem. Nov. 18, 1994;269(46):28543-6.

Wahab et al., A critical look at growth factors and epithelial-to-mesenchymal transition in the adult kidney. Interrelationships between growth factors that regulate EMT in the adult kidney. Nephron Exp Nephrol. 2006;104(4):e129-34. Epub Aug. 10, 2006.

Xia et al., Gene silencing activity of siRNAs with a ribo-difluorotoluyl nucleotide. ACS Chem Biol. Apr. 25, 2006;1(3):176-83.

Yang et al., Twist, a master regulator of morphogenesis, plays an essential role in tumor metastasis. Cell. Jun. 25, 2004;117(7):927-39.

Young et al., Integrating high-content screening and ligand-target prediction to identify mechanism of action. Nat Chem Biol. Jan. 2008;4(1):59-68.

Zavadil et al., TGF-beta and epithelial-to-mesenchymal transitions. Oncogene. Aug. 29, 2005;24(37):5764-74.

Zeng et al., Biliverdin reductase mediates hypoxia-induced EMT via PI3-kinase and Akt. J Am Soc Nephrol. Feb. 2008;19(2):380-7. doi: 10.1681/ASN.2006111194. Epub Jan. 9, 2008.

Zuckermann et al. Discovery of nanomolar ligands for 7-transmembrane G-protein-coupled receptors from a diverse N-(substituted)glycine peptoid library. J Med Chem. Aug. 19, 1994;37(17):2678-85.

Chan et al., Cancer stem cells in bladder cancer: a revisited and evolving concept. Curr Opin Urol. Sep. 2010;20(5):393-7. doi:10.1097/MOU.0b013e32833cc9df.

Economopoulou et al., The role of cancer stem cells in breast cancer initiation and progression: potential cancer stem cell-directed therapies. Oncologist. 2012;17(11):1394-401. doi:10.1634/theoncologist.2012-0163. Epub Aug. 31, 2012.

Geiger et al., Antitumor activity of a PKC-alpha antisense oligonucleotide in combination with standard chemotherapeutic agents against various human tumors transplanted into nude mice. Anticancer Drug Des. Jan. 1998;13(1):35-45.

Hedvat et al., The JAK2 inhibitor AZD1480 potently blocks Stat3 signaling and oncogenesis in solid tumors. Cancer Cell. Dec. 8, 2009;16(6):487-97. doi: 10.1016/j.ccr.2009.10.015.

Neve et al., A collection of breast cancer cell lines for the study of functionally distinct cancer subtypes. Cancer Cell. Dec. 2006;10(6):515-27.

Von Pawel, Gefitinib (Iressa, ZD1839): a novel targeted approach for the treatment of solid tumors. Bull Cancer. May 1, 2004;91(5):E70-6.

Xin et al., Antiangiogenic and antimetastatic activity of JAK inhibitor AZD1480. Cancer Res. Nov. 1, 2011;71(21):6601-10. doi: 10.1158/0008-5472.CAN-11-1217. Epub Sep. 15, 2011.

\* cited by examiner

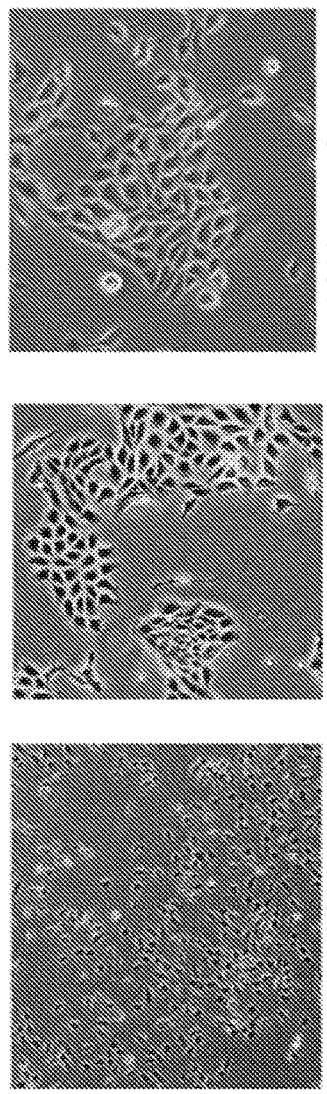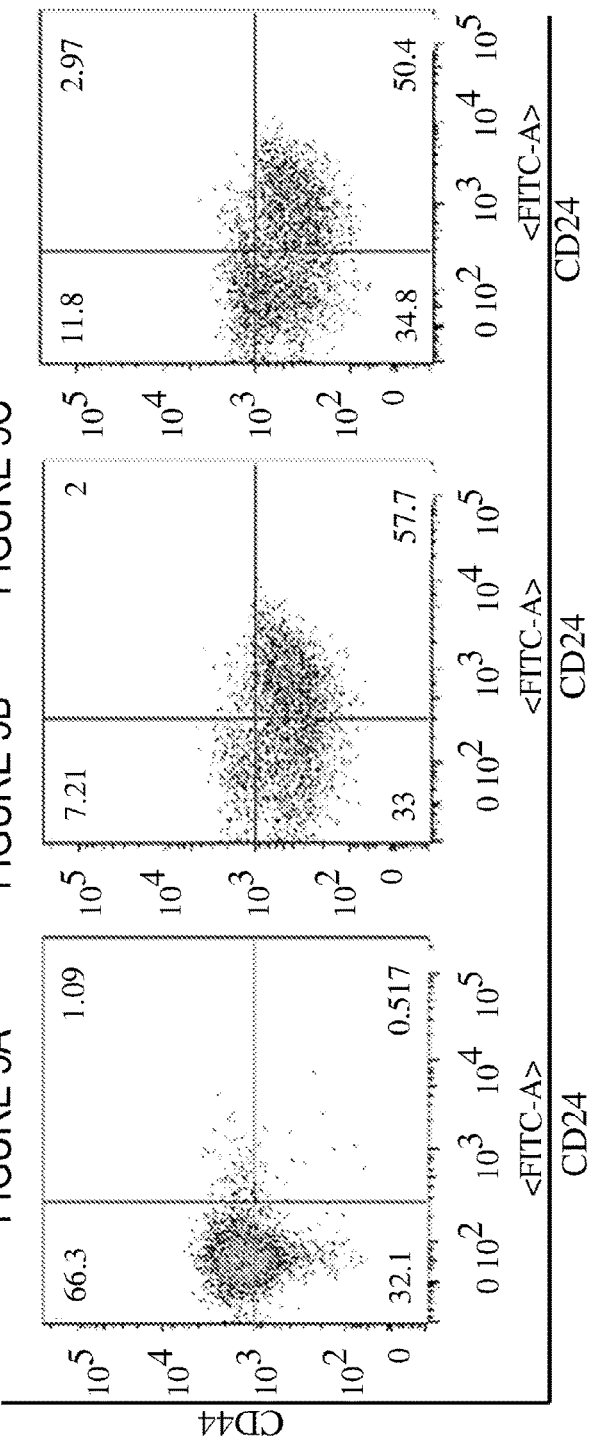

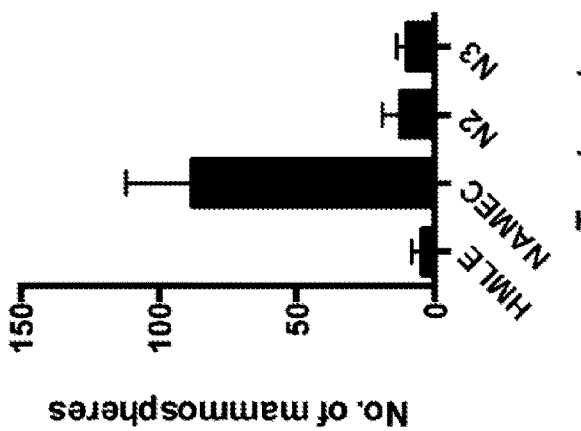
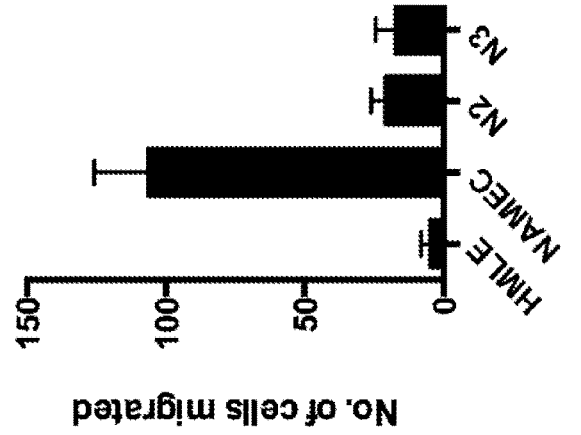
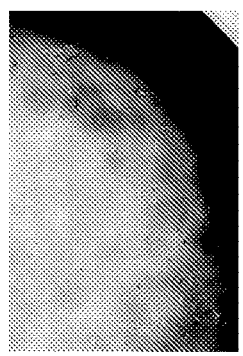
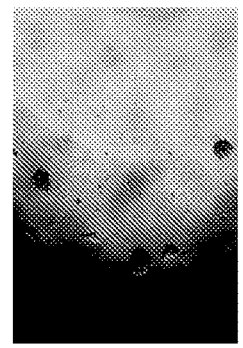
FIGURE 6B
FIGURE 6C
FIGURE 6D
FIGURE 6E
FIGURE 6F

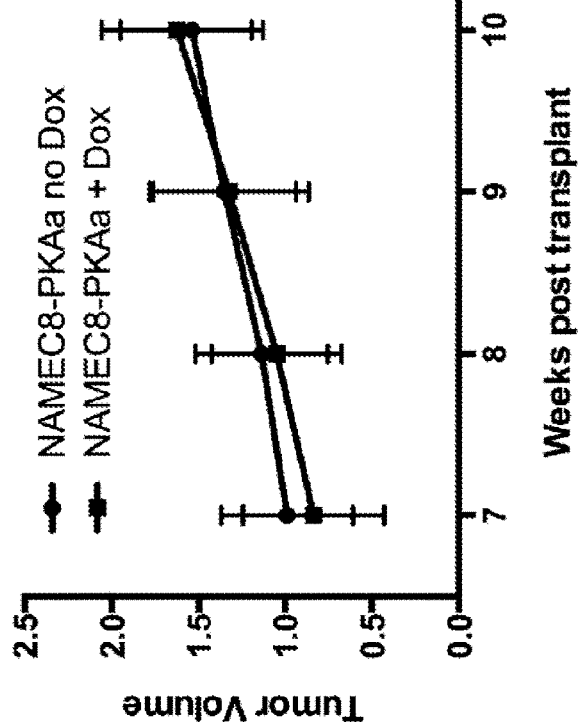
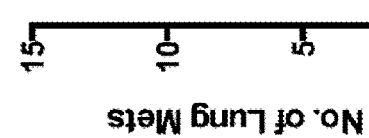
FIGURE 14B
FIGURE 14C

Secondary Transplantation

| Cell Line | Cells Transplanted | Tumors | Tumor-initiating frequency |
|---|---|---|---|
| NAMEC-Ras PKAa +Dox | 10^6 | 1/10 | 1/2508575 |
|  | 10^5 | 0/10 |  |
|  | 10^4 | 1/10 |  |
|  | 10^3 | 0/10 |  |
| NAMEC-Ras PKAa no Dox | 10^6 | 8/10 | 1/124991 |
|  | 10^5 | 5/10 |  |
|  | 10^4 | 4/10 |  |
|  | 10^3 | 1/10 |  |

FIGURE 14E

METHODS AND COMPOSITIONS FOR TARGETING CANCER STEM CELLS

RELATED APPLICATIONS

This application is a national stage filing under U.S.C. § 371 of PCT International Application PCT/US2015/028239, filed Apr. 29, 2015 entitled "METHODS AND COMPOSITIONS FOR TARGETING CANCER STEM CELLS," which claims the benefit under 35 U.S.C. § 119(e) of U.S. provisional application No. 61/986,082, filed Apr. 29, 2014, which are incorporated by reference herein in their entirety.

STATEMENT OF FEDERALLY SPONSORED RESEARCH

This invention was made with government support under grant number CA078461 awarded by the National Institutes of Health. The government has certain rights in the invention.

BACKGROUND

A number of issues confound treatment of carcinomas. First, most deaths from carcinomas (~90%) result from metastatic spread of the disease to distant sites rather than from the primary tumors; in the case of breast cancer, nearly all deaths result from metastatic dissemination. Second, the development of therapeutic resistance to initially treated tumors results in the relapse of cancers into more aggressive forms that are even more difficult to contain. Both of these properties of aggressive carcinomas can be traced to intrinsic intratumoral heterogeneity, which can arise through various mechanisms, prominent among these being the presence of subpopulations of more mesenchymal CSCs in carcinomas.

As one example, breast cancer is one of the most common cancers in women, accounting for over 30% of all cancer incidence in women in the United States. Basal-like breast cancers account for 8-20% of incident breast cancers and stain negatively for ER (estrogen receptor) and HER2 and stain positively for cytokeratin. Despite various definitions of this subtype of breast cancer and its heterogeneous nature, a unifying property is the poor clinical outcome of patients suffering from this disease, which results from its aggressive clinical history and strong association with the development of metastatic relapse. The standard-of-care for basal-like breast cancers has remained largely unchanged, continuing to rely on conventional radio- and chemotherapy, partly be due to the lack of highly specific markers to adequately characterize the genetic and epigenetic heterogeneity of this subtype, which is currently based essentially on exclusion of markers such as ER, PR (progesterone receptor) and HER2.

SUMMARY

Provided herein are methods and related compositions for treating cancer. Aspects of the disclosure relate to a recognition that cancer stem cells (CSCs) are intrinsically more resistant to many forms of conventional therapy and capable of causing tumor regrowth following cessation of therapy. Methods provided herein are particularly useful because they reduce or eliminate the presence of CSCs, which otherwise would have the ability to seed tumors and bring about a relapse or recurrence after a conventional therapy (e.g., treatment with a chemotherapeutic agent). Certain aspects are based on a discovery of regulatory pathways that control stem-like properties of CSCs and that when targeted can cause CSCs to lose their stem-like properties and transitioning the cells to a more differentiated state (e.g., via a mesenchymal to epithelial transition). In some embodiments, protein kinase A pathway is identified as a key pathway that when activated induces a mesenchymal to epithelial transition in CSCs making them more differentiated and sensitizing them to treatment with conventional therapies (e.g., treatment with a chemotherapeutic agents, radiotherapy, etc.). In some embodiments, PKA pathway activators are provided that are useful for inhibiting the tumorigenic potential and chemotherapeutic resistance of CSCs by causing the cells to undergo a MET. In other embodiments, methods are provided that involve assaying PKA pathway activity to identify compounds that selectively target CSCs.

Aspects of the disclosure relate to methods of inducing cancer stem cells to undergo a mesenchymal to epithelial transition. In some embodiments, the methods involve contacting the cancer stem cells with a Protein Kinase A (PKA) pathway activator in an amount sufficient to induce the cells to undergo a mesenchymal to epithelial transition.

Aspects of the disclosure relate to methods of sensitizing cancer stem cells to treatment. In some embodiments, the methods involve inducing cancer stem cells to undergo a mesenchymal to epithelial transition by contacting the cancer stem cells with an effective amount of a Protein Kinase A (PKA) pathway activator. In some embodiments, the treatment comprises administration of a chemotherapeutic agent or radiotherapy.

Aspects of the disclosure relate to methods of eradicating cancer stem cells. In some embodiments, the methods involve contacting the cancer stem cells with a Protein Kinase A (PKA) pathway activator in an amount sufficient to induce the cells to undergo a mesenchymal to epithelial transition, and contacting the cells with an effective amount of a chemotherapeutic agent and/or radiotherapy. In some embodiments, cancer stem cells are further contacted with the PKA pathway activator simultaneously with the chemotherapeutic agent and/or radiotherapy. In some embodiments, the cells are or were contacted with the PKA pathway activator within 1 hour, 1 day, 1 week, 1 month or more prior to being contacted with the chemotherapeutic agent and/or radiotherapy. In some embodiments, the methods involve contacting cells with a chemotherapeutic agent and/or radiotherapy, in which prior to being contacted with the chemotherapeutic agent and/or radiotherapy the cells were induced to undergo a mesenchymal to epithelial transition by being contacted with an effective amount of a Protein Kinase A (PKA) pathway activator.

In some embodiments, a PKA pathway activator induces adenylyl cyclase activity, thereby increasing cyclic AMP (cAMP) levels in the cells. In certain embodiments, a PKA pathway activator inhibits phosphodiesterase activity, thereby increasing cAMP levels in the cells. In some embodiments, a PKA pathway activator is selected from cholera toxin, forskolin, colforsin daropate (CD) and derivatives of any one of them. In some embodiments, a PKA pathway activator induces CREB-dependent transcription in the cells. In certain embodiments, a PKA pathway activator results in at least a 10 fold reduction in the half maximal inhibitory concentration (IC50) of the chemotherapeutic agent against growth or survival of the cells.

In certain embodiments, cells contacted with the PKA pathway activator express cAMP-dependent protein kinase catalytic subunit β, which is activated in response to the PKA pathway activator. In some embodiments, cells contacted with the PKA pathway activator express cAMP-dependent protein kinase catalytic subunit α, which is activated in response to the PKA pathway activator. In certain embodiments, cells contacted with the PKA pathway activator express PHF2, which is activated in response to the PKA pathway activator.

In some embodiments, a mesenchymal to epithelial transition is associated with a decrease in expression of CD44 and an increase in expression of CD24 in the cells. In certain embodiments, a mesenchymal to epithelial transition is associated with a decrease in Snail, Twist, Zeb1 and or Vimentin in the cells. In some embodiments, a mesenchymal to epithelial transition is associated with a decrease in tumor-initiation capacity of the cells.

In certain embodiments, a chemotherapeutic agent is a DNA intercalating agent or a mitotic inhibitor. In some embodiments, a DNA intercalating agent is doxorubicin. In some embodiments, a mitotic inhibitor comprises paclitaxel, docetaxel, vinblastine, vincristine, and/or vinorelbine.

Aspects of the disclosure relate to methods of treating a subject having a carcinoma. In some embodiments, the methods involve inducing cancer stem cells of the carcinoma to undergo a mesenchymal to epithelial transition by administering to the subject an effective amount of a Protein Kinase A (PKA) pathway activator. In some embodiments, the methods involve administering to the subject a Protein Kinase A (PKA) pathway activator in an amount sufficient to induce cancer stem cells of the carcinoma to undergo a mesenchymal to epithelial transition. In some embodiments, the methods further involve administering to the subject an effective amount of a chemotherapeutic agent and/or radiotherapy.

Aspects of the disclosure relate to methods of treating a subject having a carcinoma that contains cancer stem cells resistant to a chemotherapeutic agent or radiotherapy. In some embodiments, the methods involve administering to the subject an effective amount of a Protein Kinase A (PKA) pathway activator, wherein the PKA inhibitor sensitizes the cancer stem cells to the chemotherapeutic agent or radiotherapy. In some embodiments, the methods further involve administering to the subject an effective amount of a chemotherapeutic agent and/or radiotherapy. In some embodiments, a subject is administered the PKA pathway activator within 1 hour, 1 day, 1 week, 1 month or more prior to being administered the chemotherapeutic agent and/or radiotherapy. In some embodiments, a subject is administered the PKA pathway activator simultaneously with the chemotherapeutic agent.

In some embodiments, methods of treating a subject having a carcinoma are provided that involve administering to the subject a chemotherapeutic agent or radiotherapy, wherein prior to being administered the chemotherapeutic agent the subject was administered a Protein Kinase A (PKA) pathway activator in an amount sufficient to sensitize cancer stem cells of the carcinoma to the chemotherapeutic agent or radiotherapy. In some embodiments, the cells are or were contacted with the PKA pathway activator within 1 hour, 1 day, 1 week, 1 month or more prior to being contacted with the chemotherapeutic agent or radiotherapy. In some embodiments, the PKA pathway activator induces adenylyl cyclase activity, thereby increasing cyclic AMP (cAMP) levels in the cells. In some embodiments, the PKA pathway activator inhibits phosphodiesterase activity, thereby increasing cAMP levels in the cells. In some embodiments, the PKA pathway activator is selected from cholera toxin, forskolin, colforsin daropate (CD) and derivatives of any one of them. In some embodiments, the PKA pathway activator activates cAMP-dependent protein kinase catalytic subunit β in cells of the carcinoma. In some embodiments, the PKA pathway activator activates cAMP-dependent protein kinase catalytic subunit α in cells of the carcinoma. In some embodiments, the PKA pathway activator activates PHF2 in cells of the carcinoma. In some embodiments, administration of the PKA pathway activator induces CREB-dependent transcription in cells of the carcinoma. In some embodiments, administration of the PKA pathway activator results in phosphorylation of the PKA substrate in cells of the carcinoma. In some embodiments, the mesenchymal to epithelial transition is associated with a decrease in expression of CD44 and an increase in expression of CD24 in the cells. In some embodiments, the mesenchymal to epithelial transition is associated with a decrease in Snail, Twist, Zeb1 and/or Vimentin expression in the cells. In some embodiments, the mesenchymal to epithelial transition is associated with a decrease in tumor initiation capacity of the cells. In some embodiments, the chemotherapeutic agent is a DNA intercalating agent or a mitotic inhibitor. In some embodiments, DNA intercalating agent is doxorubicin. In some embodiments, the mitotic inhibitor comprises paclitaxel, docetaxel, vinblastine, vincristine, and/or vinorelbine. In some embodiments, the methods further involve evaluating effectiveness of the PKA pathway activator by detecting a level and/or activity of a component of the PKA pathway following administration of the PKA pathway activator.

Aspects of the disclosure relate to method of treating a subject having a carcinoma that involve (i) administering to the subject a PKA pathway activator; (ii) evaluating effectiveness of the PKA pathway activator by determining the level and/or activity of a component of the PKA pathway in cells of the carcinoma following administration of the PKA pathway activator; and (iii) if the PKA pathway activator is determined to be effective, administering a chemotherapeutic agent or radiotherapy to the subject. In some embodiments, the PKA pathway activator sensitizes the carcinoma to the chemotherapeutic agent or radiotherapy. In certain embodiments, evaluating effectiveness of the PKA pathway activator comprises determining whether the cAMP-dependent protein kinase catalytic subunit β is activated in response to administration of the PKA pathway activator. In some embodiments, evaluating effectiveness of the PKA pathway activator comprises determining whether cAMP-dependent protein kinase catalytic subunit α is activated in response to administration of the PKA pathway activator. In certain embodiments, evaluating effectiveness of the PKA pathway activator comprises determining whether PHF2 is activated in response to administration of the PKA pathway activator, optionally by measuring phosphorylation of PHF2. In some embodiments, evaluating effectiveness of the PKA pathway activator comprises determining whether CREB-dependent transcription is induced in response to administration of the PKA pathway activator. In certain embodiments, evaluating effectiveness of the PKA pathway activator comprises determining whether a substrate of PKA has been phosphorylated in response to administration of the PKA pathway activator. In some embodiments, evaluating effectiveness of the PKA pathway activator comprises determining whether cAMP levels are increased in response to administration of the PKA pathway activator. In certain embodiments, the carcinoma is a breast cancer. In some embodiments, the carcinoma is a basal-like breast cancer or ER-negative breast cancer. In some embodiments, the methods comprise determining that the subject has a basal-like breast cancer or ER-negative breast cancer prior to administering the PKA pathway activator to the subject.

In some embodiments, methods of treating a subject having a carcinoma are provided that involve (i) determining the extent to which the subject is susceptible to relapse by evaluating the extent to which the PKA pathway is active in cells of the carcinoma; and (ii) treating the subject for the carcinoma based on the extent to which the subject is susceptible to relapse, as determined in step (i). In some embodiments, the carcinoma is breast cancer. In some embodiments, the breast cancer is basal-like breast cancer or ER-negative breast cancer. In some embodiments, if the cells have less than a threshold level of PKA pathway activity, the subject has a relatively high likelihood of relapse, and if the cells have greater than or equal to the threshold level of PKA pathway activity, the subject has relatively low likelihood of relapse. In some embodiments, the breast cancer is a basal-like breast cancer or ER-negative breast cancer. In some embodiments, determining the extent to which the PKA pathway is active comprises detecting the level or activity of PHF2 and/or PKA catalytic subunit α and/or PKA catalytic subunit β in cells of the cancer.

In some embodiments, methods of treating a subject having a carcinoma are provided that involve (i) determining that the carcinoma comprises cancer stem cells; and (ii) administering a PKA pathway activator to the subject. In some embodiments, the carcinoma is enriched for cancer stem cells. In some embodiments, the carcinoma is characterized by increased expression of CD44 and decreased expression of CD24.

In some embodiments, method of inhibiting cancer stem cell-dependent tumor formation, progression, and/or spread in a subject are provided that comprise administering a PKA pathway activator to the subject. In some embodiments, the methods further involve administering a chemotherapeutic agent and/or radiotherapy to the subject.

Aspects of the disclosure relate to methods of identifying a candidate compound for sensitizing cancer stem cells to treatment with a chemotherapeutic agent and/or radiotherapy. In some embodiments, the methods involve (i) contacting cells with a test compound; and (ii) determining whether the Protein Kinase A (PKA) pathway is activated in the cells in response to the test compound, wherein activation of the PKA pathway in the cells indicates that the test compound is a candidate compound for sensitizing cancer stem cells to treatment with a chemotherapeutic agent and/or radiotherapy. In some embodiments, the cells that are contacted with the test compound express one or more cancer stem cell marker.

Aspects of the disclosure relate to methods of analyzing activity of a test compound. In some embodiments, the methods involve (i) contacting cells with a test compound; (ii) determining whether the Protein Kinase A (PKA) pathway is activated in the cells in response to the test compound; and (iii) if the PKA pathway is activated in the cells following treatment with the test compound, determining whether the test compound sensitizes cancer stem cells to treatment with a chemotherapeutic agent and/or radiotherapy. In some embodiments, the cells that are contacted with a test compound express one or more cancer stem cell marker. In some embodiments, step (ii) comprises determining whether the cAMP-dependent protein kinase catalytic subunit β is activated in response to the test compound. In some embodiments, step (ii) comprises determining whether cAMP-dependent protein kinase catalytic subunit α is activated in response to the test compound. In some embodiments, step (ii) comprises determining whether PHF2 is activated in response to the test compound, optionally by measuring phosphorylation of PHF2. In some embodiments, step (ii) comprises determining whether CREB-dependent transcription is induced in response to the test compound. In some embodiments, step (ii) comprises determining whether a substrate of PKA has been phosphorylated in response to the test compound. In some embodiments, step (ii) comprises determining whether cAMP levels are increased in response to the test compound. In some embodiments, step (ii) comprises determining whether PKA translocates to the nucleus of cells in response to the test compound.

Aspects of the disclosure relate to methods of identifying a candidate compound for inducing cancer stem cells to undergo a MET. In some embodiments, the methods involve (i) contacting cells with a test compound; and (ii) determining whether the Protein Kinase A (PKA) pathway is activated in the cells in response to the test compound, wherein activation of the PKA pathway in the cells indicates that the test compound is a candidate compound for inducing cancer stem cells to undergo a MET. In some embodiments, the methods further involve assessing the ability of the candidate compound to induce CSCs to undergo a MET. In some embodiments, assessing the ability of the candidate compound to induce CSCs to undergo a MET comprises assessing the effect of the compound on the level of expression of one or more CSC markers, wherein reduced expression of one or more CSC markers indicates that the candidate compound induces a MET. In some embodiments, assessing the ability of the candidate compound to sensitize CSCs to a chemotherapeutic agent or radiotherapy.

In some embodiments, methods of identifying a candidate compound for inducing a mesenchymal to epithelial transition (MET) in a cancer stem cell are provided that involve (i) contacting cells expressing one or more cancer stem cell markers with a test compound; and (ii) determining whether the test compound induces an increase in at least one indicator of an epithelial phenotype in the cells, wherein an increase in at least one indicator of an epithelial phenotype indicates that the test compound is a candidate compound for inducing a mesenchymal to epithelial transition (MET) in a cancer stem cell. In some embodiments, the cells expressing one or more cancer stem cell markers have low or absent expression of E-cadherin, and the indicator of an epithelial phenotype is expression of E-cadherin. In some embodiments, the cells comprise a nucleic acid construct comprising an E-cadherin promoter fused to a nucleic acid sequence that encodes a detectable marker. In some embodiments, the methods further involve contacting cancer stem cells with a candidate compound; and determining whether the candidate compound reduces the tumor initiation capacity of the cells. In some embodiments, the methods further involve contacting cancer stem cells with a candidate compound and a chemotherapeutic agent; and determining whether the candidate compound increases the sensitivity of the cells to the chemotherapeutic agent.

BRIEF DESCRIPTION OF DRAWINGS

The drawings provided herein are illustrative only and are not required for enablement of the disclosure.

1C shows Ras-transformed HMLE cells forming well-differentiated tumors with lobular structures. FIG. 1D shows Ras-transformed NAMEC cells forming poorly differentiated tumors.

FIG. 3A shows an exemplary lentiviral vector with the E-cadherin (CDH1) promoter fused to the luciferase gene. FIG. 3B shows the lentiviral vector stably expressed in NAMEC cells that are screened in 384-well plates following treatment of the cells with 0.5 µm of a test molecule. Quantification of luciferase 6 days after the treatment is used as a readout of activation of the E-cadherin promoter. FIG. 3C shows relative CDH1 Promoter luciferase activity normalized by cells number for tested compounds. Differential activity between non-CSCs and CSC for Forskolin is indicated (around 40-fold), and a bar chart is provided.

FIG. 4A shows the relative levels of luciferase production obtained in the screen in both HMLE cells and NAMEC cells following treatment of the cells with forskolin or DMSO control. FIG. 4B shows the relative levels of luciferase production from cells that were treated with forskolin, as obtained after assay optimization. FIG. 4C shows the relative levels of luciferase production from cells that were treated with cholera toxin, as obtained after assay optimization.

FIGS. 5A-5I show induction of the mesenchymal to epithelial transition in NAMEC cells following treatment with cholera toxin (center panels) or forskolin (right panels) but not in cells treated with DMSO control (left panels). FIGS. 5A-C show exemplary bright field micrographs of cells following 12-14 days of the indicated treatment, which from left to right was DMSO, cholera toxin and forskolin. The cholera toxin or forskolin treated cells display a cobblestone morphology and formation of islands. FIGS. 5D-F show flow cytometric analysis of cells following the indicated treatment, which from left to right was DMSO, cholera toxin and forskolin. NAMEC cells treated with either cholera toxin or forskolin lose their $CD44^{hi}CD24^{lo}$ stem cell marker profile and revert back to a non-stem cell $CD44^{lo}CD24^{hi}$ phenotype. FIGS. 5G-I shows exemplary fluorescence micrographs of NAMEC cells following treatment, which from left to right was DMSO, cholera toxin and forskolin. Cells treated with either cholera toxin or forskolin show re-expression of E-cadherin at the cell junctions and loss of the mesenchymal marker, fibronectin.

FIGS. 6A-6F show NAMEC cells that have been induced to undergo a mesenchymal to epithelial transition by treatment with cholera toxin or forskolin lose properties of cancer stem cells. FIG. 6A shows a decrease in relative expression of the indicated mesenchymal markers and a gain of E-cadherin expression following treatment with cholera toxin or forskolin compared to untreated NAMEC cells. For each marker assessed, columns are expression in HMLE cells, NAMEC cells, N2 cells, and N3 cells, from left to right. FIG. 6B shows that cholera toxin or forskolin treatment reduces the migratory ability of NAMEC cells. FIG. 6C shows the cholera toxin or forskolin treatment reduces the invasive ability of NAMEC cells. FIG. 6D shows the number of mammospheres formed is lower in the NAMEC cells that have been treated with cholera toxin or forskolin compared to untreated NAMEC cells. FIGS. 6E and 6F show examples of bright field micrograph images of mammospheres in NAMEC compared with N2 cells.

FIG. 7A presents a table of the tumor-initiating frequency of the indicated cells when transformed with Ras and xenographed into NOD/SCID mice. FIG. 7B shows the measured tumor size (mm) formed by the indicated cells when xenographed into mice. FIG. 7C presents the number of lung micrometastases formed by the indicated cells. These results indicate that inducing an MET through the activation of PKA can lead to a loss of tumor-initiating ability and metastatic ability

FIGS. 10A and 10C show relative expression of PRKACB and PRKACA following shRNA targeting of PRKACB. FIGS. 10B and 10D show representative micrographs of NAMEC cells treated with cholera toxin for 10 days and treated with shRNA construct sh2 or control shRNA construct shLuc.

FIG. 11A shows relative knockdown of PFH2 following shRNA targeting of PHF2. FIGS. 11B and 11D show representative micrographs of NAMEC cells treated with cholera toxin for 10 days and treated with PHF2 shRNA constructs sh3 or sh5. FIG. 11C presents a schematic depiction of the protein domains of PHF2 with PHF8 and KIAA1718.

FIG. 12A shows PHF2 in ER-negative breast cancer. FIG. 12B shows PHF2 in basal-like breast cancer. FIG. 12C shows PHF2 following chemotherapy treatment. FIG. 12D shows PRKACA in basal-like breast cancer. FIG. 12E shows PRKACB in basal-like breast cancer. FIG. 12F shows PHF2 and PRKACA. In each plot, the ordinate is probability of survival and the abscissa is time in years.

FIG. 13A shows NAMEC-Ras tumors after 2 weeks of intraperitoneal administration of DMSO. FIG. 13B shows NAMEC-Ras tumors after 2 weeks of intraperitoneal administration of forskolin (5 mg/kg daily).

FIGS. 14A-14E show the results of activating PKA in NAMEC8-Ras tumors in vivo. FIG. 14A shows a schematic representation of the experimental set up. FIG. 14B shows tumor volume in mice secondarily transplanted with cells from mice that received doxycycline to induce PKA expression (squares) or control (no Dox, circles). FIG. 14C shows the number of lung metastases in mice secondarily transplanted with cells from mice that received doxycycline to induce PKA (Dox) or control (no Dox). FIG. 14D shows flow cytometric analysis of the CSC profile of populations of cells from mice transplanted with NAMEC-Ras PKA cells that received doxycycline to induce PKA (+Dox; bottom right panel) or control (no Dox; bottom left panel). Flow cytometric analysis of HMLE cells (top left panel) and NAMEC cells (top right panel) are provided for reference. FIG. 14E shows the tumor-initiating ability of cells isolated from mice that had received doxycycline to induce PKA (NAMEC-Ras PKAa+Dox) or control (NAMEC-Ras PKAa no Dox) following secondary transplantation at limiting dilutions.

DETAILED DESCRIPTION

Figure 1:
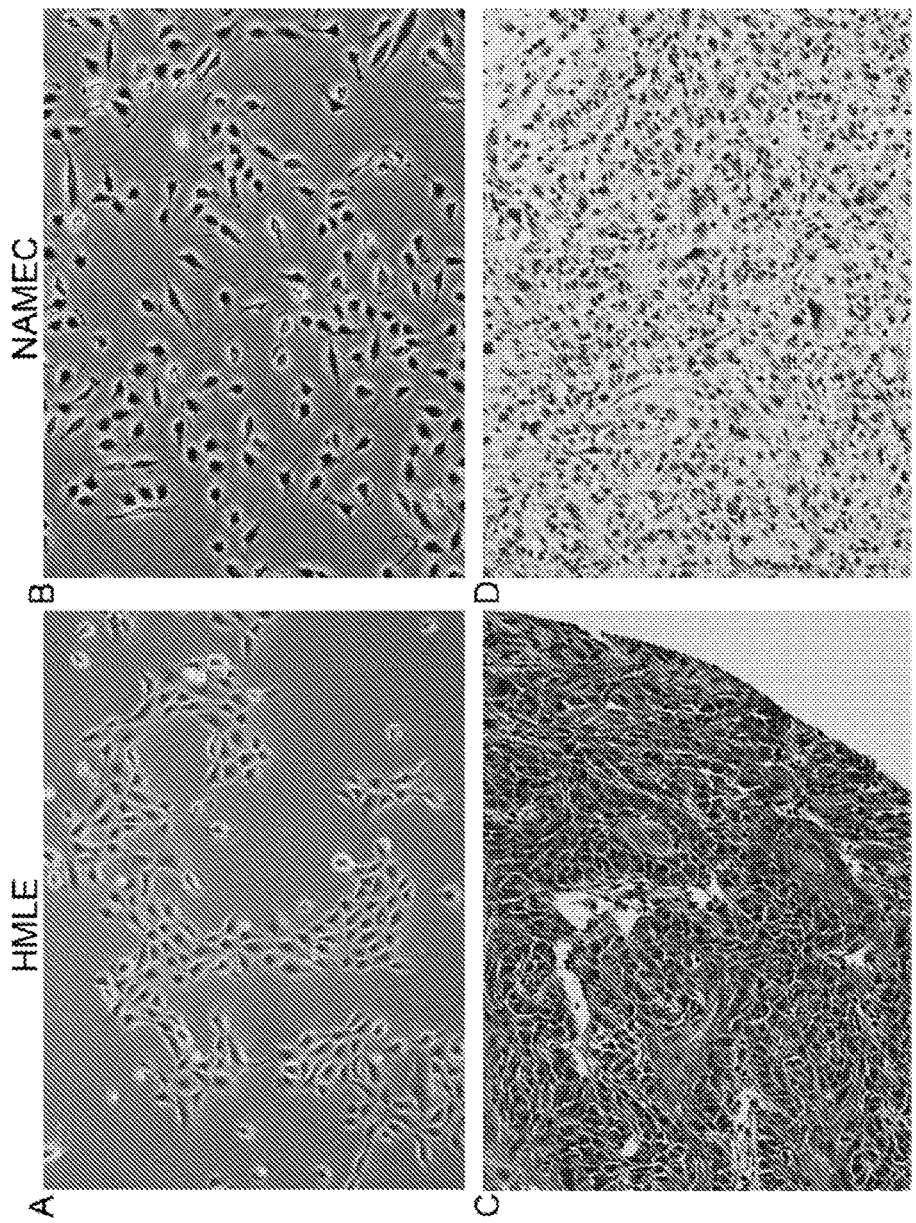
FIGS. 1A and 1B show representative bright field micrograph images of (A) HMLE cells exhibiting epithelial cobblestone-like morphology and (B) NAMEC cells exhibiting mesenchymal-like morphology.
FIGS. 1C and 1D show representative bright field micrograph images of tumor cells that had been stained with hematoxylin and eosin following transformation with Ras and orthotopic transplantation. FIG.

Aspects of the disclosure are based on a recognition that when CSCs undergo a mesenchymal-to-epithelial transition (MET) the resulting epithelial-like cells have reduced tumorigenic potential and increased susceptibility to chemotherapeutic agents compared with CSCs. In particular, it has been discovered that activation of protein kinase A (PKA) pathway induces cancer stem cells to undergo an MET. Therefore, disclosed herein are methods and compositions for inducing CSCs to undergo a MET through activation of the PKA pathway. Methods and compositions provided herein are particularly useful for treating cancer because they sensitize CSCs to conventional therapies, such as treatments involving chemotherapeutic agents or radiotherapy, and thereby minimize the likelihood of recurrence following conventional therapies.

Mesenchymal to Epithelial Transition

Aspects of the disclosure relate to the discovery that cancer stem cells (CSCs) can be induced to undergo a mesenchymal-to-epithelial transition by activating the protein kinase A (PKA) pathway. Cancer stem cells (CSC) display many mesenchymal properties including spindle-shaped morphology, migratory ability, self-renewal capacity, tumorigenicity, resistance to standard chemotherapeutic agents, increased expression of markers associated with the mesenchymal state, such as Vimentin, Fibronectin, N-cadherin, Snail, Zeb1, and Twist, and decreased expression of cell surface markers associated with the epithelial state, such as E-cadherin. Methods described herein provide novel approaches for stimulating CSCs to undergo a mesenchymal-to-epithelial transition. After undergoing the mesenchymal-to-epithelial transition, which may also be referred to as mesenchymal-to-epithelial transdifferentiation, cells exhibit properties of epithelial cells including increased expression of epithelial cell surface markers (e.g., E-cadherein), decreased expression of mesenchymal cell markers (e.g., Vimentin, Fibronectin, N-cadherin, Snail, Zeb1, Twist), a decrease in migratory ability, lower tumorigenicity, formation of well-defined tumors, and increased sensitivity to standard chemotherapy drugs. Methods and compositions of the present disclosure may enhance the therapeutic effects of conventional chemotherapeutic agents when administered concomitantly or in series.

As used herein, a "mesenchymal-to-epithelial transition" (MET) refers to a transformation of a mesenchymal cell that has one or more characteristics of a cancer stem cell into a cell having one or more epithelial properties. Cells that have undergone an MET may exhibit markers of gene expression that are characteristic of epithelial cells (e.g., cell surface markers of epithelial cells) and/or an one or more functional properties characteristic of epithelial cells. Exemplary markers for which increased expression in a cell that has undergone a MET, compared with a cell that has not undergone a MET, is indicative of the MET include E-cadherin, cytokeratins, CD24, and CD104. Examples of markers for which decreased expression in a cell that has undergone a MET, compared with a cell that has not undergone a MET, is indicative of the MET include Vimentin, Fibronectin, N-cadherin, Snail, Twist, Zeb1, and CD44. The extent to which a mesenchymal cell has undergone an MET may be assessed by determining the expression of one or more markers using an appropriate expression detection assay, such as an RNA expression detection assay (e.g., qRT-PCR assay, FISH assay, etc.) or a protein detection assay (e.g., a western blot, ELISPOT, flow cytometry based immunoassay, etc.).

It is to be understood that functional properties of any cells of the present disclosure (e.g., CSCs and epithelial cells) may be assessed using a variety of methods known in the art. Cellular morphology can be evaluated by microscopy methods including, for example, bright field and fluorescence microscopy. The expression level of cell markers associated with the mesenchymal state or the epithelial cell state can be evaluated by methods including quantitative RT-PCR, flow cytometry, cell staining, antibody detection of cell surface markers, Western blotting, and fluorescence microscopy. The migratory ability of cells can be assessed, for example, by a cell migration assay. The invasion and metastatic abilities of a cell can be evaluated, for example, by transplanting a cell into an animal model and quantifying the metastases or tissue-invading cells. Tumorigenicity of a cell can be assessed, for example, by transplanting a cell into an animal model and quantifying the number and/or size of tumors formed. Cells can be further evaluated for sensitivity to chemotherapeutic agents. Following exposure of the cell to a chemotherapeutic agent the viability of the cell can be assessed by any method known in the art, including, for example, proliferation, metabolic activity, and live/dead staining. In some embodiments, the sensitivity to chemotherapeutic agents can be represented as a half maximal inhibitory concentration (IC50). Any property of cells that have undergone a MET may be assessed by a comparison with cells that have not undergone a MET (e.g., control cells).

PKA Pathway

The present disclosure provides methods and compositions for treating cancer that involve stimulating PKA pathway activity to aid in the eradication of CSCs. In some embodiments, methods for treating cancer provided herein involve inducing one or more cells within a population to undergo a MET by activating PKA. In other embodiments, methods are provided that involve assaying PKA pathway activity to identify compounds that selectively target CSCs. As used herein, the "protein kinase A pathway" or "PKA pathway" refers to a molecular pathway of a cell that involves the activity of protein kinase A (PKA). Components of the PKA pathway include biomolecules that are upstream or downstream of PKA, including, but not limited to receptors, enzymes, signaling factors, second messengers, transcription factors, etc. For example, the PKA pathway may include, without limitation, cyclic AMP, adenylate cyclases, phosphodiesterases (e.g., PDE1, 2, 3, 4, 7, 8 10 and 11), receptors, including G-protein coupled receptors, and any substrate of PKA kinase activity, including proteins containing a Arginine-Arginine-X-Serine motif.

As used herein, "PKA" refers to protein kinase A, which is also known as cAMP-dependent protein kinase. PKA belongs to a serine/threonine protein kinase family and is a holoenzyme comprising a regulatory subunit dimer and two catalytic subunits. In humans, there are four identified PKA regulatory subunits, encoded by genes PRKAR1A, PRKAR1B, PRKAR2A, and PRKAR2B, and three identified catalytic subunits, encoded by genes PRKACA, PRKACB, and PRKACG. There are at least two isoforms of PKA, type I and type II, that differ in subunit composition. PKA is generally regulated by cAMP levels. In conditions of low cAMP levels in a cell, catalytic subunits of PKA associate with the inhibitory domain of the regulatory subunit dimer, rendering PKA inactive. In conditions of high cAMP levels in a cell, cooperative binding of cAMP to the nucleotide binding sites of the regulatory subunit dimer allows release and activation of the catalytic subunits. Active PKA phosphorylates target molecules, such as PHF2, hormone sensitive lipase (HSL), acetyl-CoA carboxylase, CREB, Atg13, ryanodine receptor, heat shock protein Hsp20, and myosin binding protein.

In some embodiments, the phosphorylation state of a PKA substrate, e.g., PHF2, may be evaluated to determine the activity of PKA. In some embodiments, a PKA phosphorylation substrate is selected from PHF2, CREB, CBP, NF-κB, eNOS, VASP, Rho, DARPP32, RyR, PHK, Pin, CRP, Thh1, GSK3, Ezrin, Gli1, Gli2, Gli3, and GYS. In some embodiments, the PKA substrate is Ezrin which may be phosphorylated and activated by PKA phosphorylation at Ser66. In some embodiments, the PKA substrate is Gli1, Gli2, or Gli1 which may be phosphorylated by PKA on multiple sites.

In some embodiments, CREB-dependent transcription is assessed to determine the activity of PKA. In some embodiments, the PKA pathway activity in a cell may be evaluated to determine whether a cell is in a mesenchymal or epithelial state. For example, low-levels of PKA kinase activity may be indicative of a mesenchymal state; whereas high-levels of PKA kinase activity may be indicative of an epithelial state. In some embodiments, PKA pathway activity may be evaluated to determine the extent to which a cell has transitioned from a mesenchymal to epithelial state (e.g., to determine the status of a mesenchymal to epithelial transition). Moreover, in other embodiments PKA pathway activity may be evaluated to determine the extent to which a cell has transitioned from a epithelial to mesenchymal state (e.g., to determine the status of a epithelial to mesenchymal transition.

The activity of a PKA pathway can be evaluated by any appropriate method, including, without limitation, i) assessing the phosphorylation state of PKA, ii) assessing the phosphorylation state of one or more substrates of PKA, iii) evaluating the extent to which PKA catalytic subunit dimers are associated with regulatory subunit dimers, iv) evaluating the activity of upstream regulators of PKA (e.g., G-protein coupled receptor activity, adenylate cyclase activity, phosphodiesterase activity, etc.), v) evaluating the intracellular localization of PKA (in which nuclear localization is associated with active PKA) and/or vi) evaluating levels of cAMP. Antibodies that can be used to detect the phosphorylation state of PKA or a PKA target molecule are known in the art and may be used to evaluate PKA activity; non-limiting examples include anti-phospho-PKA substrate antibodies (Cell Signaling Technology), anti-phospho-Ser/Thr PKA substrate antibodies (Cell Signaling Technology), anti-phospho-Ser 359 antibodies (Santa Cruz Biotechnology), and anti-C alpha antibodies (Santa Cruz Biotechnology).

As used herein, "cAMP" refers to cyclic 3'-5'-adenosine monophosphate. In some embodiments, the level of cAMP may be evaluated to determine whether a cell has undergone a MET. In some embodiments, the level of cAMP in a cell (e.g., concentration) is compared to the level of cAMP in a second cell (e.g., a control cell), and the designation of high or low level of cAMP in the first cell is relative to the level in the second cell. The level of cAMP in a cell (e.g., concentration) can be measured by any method known in the art including, a cAMP reporter system, a fluorometric assay as described in U.S. Pat. No. 5,316,907, antibody detection by ELISA, mass spectrometry, high performance liquid chromatography, and any cAMP detection kit, for example that described in U.S. Pat. No. 6,541,196. In some embodiments, the cAMP level in cells of a population (e.g. a tissue from a subject) can be evaluated. In some embodiments, the level of cAMP is compared to a threshold level of cAMP. As used herein, a "threshold level of cAMP" is a predetermined value the distinguishes between two conditions, e.g., high and low concentrations of cAMP. In some embodiments, the cAMP level in a cell indicates a state of a cell (e.g., mesenchymal or epithelial). In some embodiments, a cAMP level above a threshold indicates a cell is in an epithelial cell state. In some embodiments, a cAMP level below a threshold indicates a cell is a mesenchymal cell. In some embodiments, the level of cAMP in a cell can identify whether a cell is a candidate for treatment, as described herein.

As used herein, a "PKA pathway activator" refers to an agent that directly or indirectly activates PKA. In some embodiments, a PKA pathway activator is an agent that directly or indirectly increases cAMP levels in a cell. In some embodiments, a PKA pathway activator is an agent that directly or indirectly increases levels and/or activity of adenylate cyclase in a cell. In some embodiments, a PKA pathway activator is an agent that directly or indirectly decreases levels and/or activity of a phosphodiesterase in a cell. In some embodiments, a PKA pathway activator is an agent that directly activates PKA kinase activity.

In some embodiments, an agent that directly activates PKA kinase activity binds to a catalytic or regulatory subunit dimer of PKA. Non-limiting examples of PKA activators include 3,3'-diamino-4,4'-dihydroxydiphenylmethane (FMP-API-1), 6-Bnz-cAMP, dibutyryl-cAMP, adenosine 3',5'-cyclic monophosphate acetoxymethyl ester, adenosine-3',5'-cyclic monophosphorothioate acetoxymethyl ester, Sp-Adenosine 3',5'-cyclic monophosphorothioate triethylammonium salt hydrate, Rp-Adenosine 3',5'-cyclic monophosphorothioate triethylammonium salt, 8-AHA-cAMP, 8-Bromoadenosine 3',5'-cyclic monophosphate, 8-Bromoadenosine 3',5'-cyclic monophosphate sodium salt, 8-Chloroadenosine 3',5'-cyclic-monophosphate, 8-(4-Chlorophenylthio)adenosine 3',5'-cyclic monophosphate sodium salt, 8-(4-Chlorophenylthio)-2'-O-methyladenosine 3',5'-cyclic monophosphate monosodium hydrate, N6,2'-O-Dibutyryladenosine 3',5'-cyclic monophosphate sodium salt, Sp-8-pCPT-cAMPS, 8-PIP-cAMP, CW008, and derivatives of any of the foregoing.

Activation of G protein coupled receptors that couple to Gs alpha subunit leads to increased cAMP levels by activating adenylate cyclase. Accordingly, in some embodiments, a PKA pathway activator is an agonist of one or more of such G protein coupled receptors. For example, a PKA pathway activator may be an agonist of one or more of the following G protein coupled receptors: 5-HT receptor types 5-HT4 and 5-HT7; ACTH receptor; adenosine receptor types A2a and A2b; arginine vasopressin receptor 2; β-adrenergic receptors types β1, β2 and β3; calcitonin receptor; calcitonin gene-related peptide receptor; corticotropin-releasing hormone receptor; dopamine receptor D1-like family types (D1 and D5), FSH-receptor; gastric inhibitory polypeptide receptor; glucagon receptor; histamine H2 receptor; luteinizing hormone/choriogonadotropin receptor; melanocortin receptors MC1R, MC2R, MC3R, MC4R, and MC5R; parathyroid hormone receptor 1; prostaglandin receptor types D2 and I2; secretin receptor; and thyrotropin receptor.

On the other hand, activation G protein coupled receptors that couple to Gi alpha subunit leads to decreased cAMP levels by inhibiting adenylate cyclase. Thus, in some embodiments, a PKA pathway activator is an antagonist of a G protein coupled receptors that couples to the Gi alpha subunit. For example, a PKA pathway activator may be an antagonist of one or more of the following G protein coupled receptors: acetylcholine M2 and M4 receptors; adenosine A1 and A3 receptors; adrenergic α2A, α2B, and α2C receptors; apelin receptor; calcium-sensing receptor; cannabinoid receptors (CB1 and CB2); chemokine CXCR4 receptor; dopamine D2, D3 and D4 receptors; GABAB receptor; glutamate mGluR2, mGluR3, mGluR4, mGluR6, mGluR7, and mGluR8 receptors; histamine H3 and H4 receptors; melatonin MT1, MT2, and MT3 receptors; opioid δ, κ, μ, and nociceptin receptors; prostaglandin EP1, EP3, FP, and TP receptors; serotonin 5-HT1 and 5-HT5 receptor; and somatostatin sst1, sst2, sst3, sst4 and sst5 receptors.

Adenylate cyclases catalyze the formation of 3,5 cyclic AMP (cAMP) from ATP. There are six distinct classes of adenylate cyclases of which class III cyclases are present in mammals. Class III adenylate cyclases are further divided into ten isoforms, ADCY1, ADCY2, ADCY3, ADCY4, ADCY5, ADCY6, ADCY7, ADCY8, ADCY9, ADCY10. In some aspects of the present disclosure, the PKA pathway activator may activate PKA by increasing the level of cAMP within a cell through stimulating the activity of one or more cAMP adenylate cyclases. Exemplary molecules that activate cAMP adenylate cyclases include, forskolin, cholera toxin, colforsin daropate (CD), and derivatives thereof.

Certain phosphodiesterases (PDEs) mediate the hydrolysis of cAMP to 5' AMP. There are 11 families of general phosphodiesterases of which families 1, 2, 3, 4, 7, 8, 10, and 11 are able to hydrolyze cAMP. The opposing activities of cAMP adenylate cyclases and cAMP phosphodiesterases function to regulate and maintain intracellular concentrations of cAMP in response to intracellular or extracellular signals to the cell. In some embodiments of the present disclosure, a PKA pathway activator increases the level of cAMP within a cell by decreasing the level and/or activity of one or more PDEs in a cell. In some embodiments, the level of cAMP within a cell is increased by decreasing the expression of one or more PDEs in a cell. In some embodiments, a PKA pathway activator is an PDE inhibitor. Exemplary PDE inhibitors include, without limitation, 1,3-Dipropylxanthine, 5'-Deoxy-5'methylioadenosine, 7-(β-Hydroxyethyl)-theophylline, 8-MeOM-IBMX, Acetidenafil, Aminophylline, Amrinone, Anagrelide, Anagrelide-13C3, Anagrelide hydrochloride, BAY 60-7550, BC 11-38, BRL-50481, Butein, Caffeine, CaM Kinase II (290-309, Calmodulin Antagonist, CDP 840 hydrochloride, CGH 2466, Chlorpromazine Hydrochloride, Cilomilast, Cilostamide (OPC 3689), Cilostamide Enoxamone, Cilostazol, CP 80633, Denbufylline, Dihydro-pyridazinone, Diphylline, Dipyridamole, Doxofylline, Drotaverine, E6 Berbamine, EHNA, EHNA hydrochloride, EHNA (MEP-1), Enoximone, Etazolate Hydrochloride, Furafylline, Gisadenafil besylate, GSK256066, IBMx, Ibudilast, ICI 63197, Inamrinone, Irsogladine maleate, J-8 hydrochloride, Ketotifen fumarate, KS-505a, Levosimendan, Lixazinone, LY 171883, Luteolin, MDL-12,330A.HCl, Mesembrine, Mesopram, Methylated xanthines, Methylxanthine, Milrinone, Milrinone Siguazodan, Nicardipine, Nimodipine, Obscurolide A1, Ophiobolin A, Oxindole, Papaverine, Papverine hydrochloride, Paraxanthine, PDP, Pentoxifylline, PF-2545920, Piclamilast, Prazosin hydrochloride, Quazinone (Ro 13-6438), Quercetin, Quercetin Dihydrate, R-(−)Rolipram, Reticulol, Roflumilast, Roflumilast-d3, Rolipram, RS 25344 hydrochloride, S-(+)-Rolipram, Siguazodan, Tadalafil, Theobromine, Theophylline, Trequinsin hydrochloride, Trifluoperazine-2HCl (Stelazine), Vardenafil Dihydrochloride Salt, Vinpocetine, W-5, YM 976, W-12 hydrochloride, Zaprinast, and Zardaverine.

In some embodiments, a selective cAMP phosphodiesterase inhibitor is used in the methods described herein. In some embodiments, the selective cAMP phosphodiesterase inhibitor inhibits a phosphodiesterase that selectively hydrolyzes cAMP, such as a phosphodiesterase that belongs to PDE family 4, 7, or 8. Examples of selective cAMP phosphodiesterase inhibitors include, without limitation, Mesembrine, Ibudilast, Piclamilast, Luteolin, Drotaverine, Rolipram, R-(−)Rolipram, S-(+)-Rolipram, Roflumilast, Roflumilast-d3, CDP 840 hydrochloride, Denbufylline, Etazolate Hydrochloride, GSK256066, ICI 63197, Mesopram RS 25344 hydrochloride, YM 976, Cilomilast, BRL-50481, CGH 2466, Dihydro-pyridazinone.

Any additional method known in the art can be used to activate a PKA pathway. For example, inhibitory nucleic acids can target and inhibit PDEs (e.g., siRNA, shRNA, miRNA). In another example, inhibitory nucleic acids can target and inhibit a molecule that negatively regulates a cAMP adenylate cyclase (e.g., a guanosine nucleotide-binding proteins (G proteins) and G protein-coupled receptors). Inhibitory nucleic acids can be delivered to a cell as a vector for stable integration, as described herein.

In some embodiments, the PKA pathway activator can be conjugated to a molecule that targets the PKA pathway activator to a CSC cell. Specific targeting of the PKA pathway activator may enhance the desired effect of the PKA pathway activator (e.g., phosphorylation of a PKA substrate), increase internalization of the PKA pathway activator, or minimize PKA activation in cells that are not CSC cells. In some embodiments, the PKA pathway activator is conjugated to an antibody. In such embodiments, the antibody may comprise one or more antigen-binding domains that binds to a molecule that is present on a CSC. In some embodiments, the antibody binds to a molecule that is present on a CSC but is not present on non-CSCs. In some embodiments, the PKA pathway activator is conjugated to a non-antibody targeting agent, such as a small molecule, a receptor ligand, a nanoparticle, or any other molecule known in the art to selectively bind to a CSC. Non-limiting examples of molecules present on CSCs that may be targeted by antibodies or other targeting agents conjugated to PKA pathway activators include CD44, p-glyco-protein1, hyaluronate receptor, EpCAM Epidermal surface antigen, CD326, flotillin, CD133 Prominin-1, CXCR-4, IL-4, IL-6, PSCA, CD200, CD123, DLL4, Frizzled, Wnt, Notch, Patched, Integrin, ALDH-1, and VEGF/VEGFR. Methods of conjugating a molecule, such as a PKA pathway activator, to a targeting molecule, such as an antibody or other targeting agent, are well known in the art.

In some embodiments, PKA pathway activators are provided that result in a reduction in the half maximal inhibitory concentration (IC50) of a chemotherapeutic agent against a cell (e.g., a cancer stem cell). IC50 is the concentration that is half of the concentration producing a maximal inhibitory effect on cells. In some embodiments, the inhibitory effect is inhibition of cell growth or proliferation. In some embodiments, the inhibitory effect is an induction of cell killing or a decrease in cell viability. In this context, cells may be identified as "sensitized" to a chemotherapeutic agent by a PKA pathway activator when treatment with the activator results in at least a 2-fold, 5-fold, 10-fold, 20-fold, 50-fold, or 100-fold reduction the IC50 of a chemotherapeutic agent.

Cells

Aspects of the disclosure relate to methods for inducing cells to undergo a mesenchymal-to-epithelial transition, for example, by activating protein kinase A (PKA) in the cells. Further aspects of the disclosure relate to methods that involve evaluating PKA pathway activity in cells, e.g., for purposes of identifying or characterizing PKA pathway activators. Cells may be in vitro or in vivo. In some embodiments, cells are mammalian cells, e.g., human cells or non-human animal cells, e.g., cells of non-human primate, rodent (e.g., mouse, rat, guinea pig, rabbit), origin, or interspecies hybrids. In certain embodiments the cells are obtained from a biopsy (e.g., tissue biopsy, fine needle biopsy, etc.) or at surgery for a cancerous or noncancerous condition. In some embodiments, the cell is of a cancer cell line. Exemplary human cancer cell lines include, without limitation, MCF7Ras, HCC1806, SUM159, MDA-MB-231, Hs578T, and MD-MD-468 cells. In some embodiments, cells used in methods disclosed herein do not have detectable promoter methylation of an E-Cadherin gene.

In some embodiments, cells for use of the present disclosure may be derived from a cancer (e.g., naturally occurring cancer). In some embodiments, the cancer from which cells are derived is a colon carcinoma, a pancreatic cancer, a breast cancer, an ovarian cancer, a prostate cancer, a squamous cell carcinoma, a cervical cancer, a lung carcinoma, a small cell lung carcinoma, a bladder carcinoma, a squamous cell carcinoma, a basal cell carcinoma, an adenocarcinoma, a sweat gland carcinoma, a sebaceous gland carcinoma, a papillary carcinoma, a papillary adenocarcinoma, a cystadenocarcinoma, a medullary carcinoma, a bronchogenic carcinoma, a renal cell carcinoma, a hepatocellular carcinoma, a bile duct carcinoma, a choriocarcinoma, a seminoma, a embryonal carcinoma, a Wilms' tumor, melanoma, or a testicular tumor. In one embodiment, cancer is a lung carcinoma. In one embodiment, cancer is a breast carcinoma. Other cancers will be known to one of ordinary skill in the art.

In some embodiments the cancer is a spontaneously arising cancer. In some embodiments the cancer is a cancer associated with a known or characteristic genetic mutation or polymorphism. In some embodiments the cancer is an experimentally produced cancer. In some embodiments the cancer is a hormone-responsive cancer. In some embodiments the cells are derived from an early stage cancer or precancerous lesion, e.g., a papilloma, adenoma, dysplastic lesion, etc., or a carcinoma in situ. In some embodiments the cancer is one that is responsive to a chemotherapeutic agent or combination thereof (e.g., any one or more of the chemotherapeutic agents discussed below). In some embodiments the cancer is one that is resistant to a chemotherapeutic agent or combination thereof. In some embodiments, methods provided herein result in decreased resistance of the cancer to a chemotherapeutic agent, radiotherapy, or a combination thereof.

In some embodiments, cells that are used in methods disclosed herein are Naturally Arising MEsenchymal Cells (NAMECs). These cells are derived from Human Mammary Epithelial Cells (HMLE) cells and are formed in the absence of introduced exogenous EMT-inducing master transcription factors (EMT-TFs), such as Twist, Snail and Slug and/or in the absence of genetic modification that inhibits E-cadherin expression. In some embodiments NAMECs are formed from cells that are free of genetic modification that would cause such cells to undergo an EMT. In some embodiments NAMECs are formed from cells that are free of genetic modification provided, however, that in some embodiments such cells contain a genetic modification to immortalize such cells, a genetic modification to cause them to express a detectable marker, and/or a genetic modification to cause them to express an oncogene or have reduced or absent expression of a tumor suppressor gene. In some embodiments NAMECs express elevated levels of one or more endogenous EMT-TFs (e.g., Twist, Snail, Slug, Zeb1 and/or Zeb2). In some embodiments, a PKA pathway activator induces NAMECs to undergo an MET transition.

In some embodiments NAMECs express elevated levels of one or more associated EMT markers or EMT indicators (e.g., vimentin, N-cadherin and fibronectin). In some embodiments NAMECs express reduced levels of the epithelial adherens junction protein, E-cadherin. In some embodiments, NAMECs are characterized as CD44hi/CD24lo, similar to mammary epithelial stem cells that are naturally present within HMLE populations. In some embodiments, NAMECs have relatively high mammosphere-forming ability compared with corresponding epithelial cells that have not undergone an EMT. In some embodiments NAMECs are characterized as having elevated (e.g., high) expression of any one or more markers characteristic of epithelial stem cells, e.g., epithelial stem cells found in or originating from a particular organ or tissue type. In some embodiments NAMECs are characterized as having elevated (e.g., high) expression of any one or more markers characteristic of cancer stem cells, e.g., CSCs originating found in a particular organ or tissue type or originating from epithelial cells from a particular organ or tissue type. In some embodiments a marker of epithelial stem cells or CSCs comprises a physical property such as differential light scattering, dye exclusion, etc., as compared with non-stem cells.

Methods of Treatment

Methods of treating a subject having a cancer (e.g., carcinoma) are provided herein. In some embodiments, methods are provided that involve inducing a cancer stem cell of the carcinoma to undergo a MET. In some embodiments, methods are provided that involve administering to a subject an effective amount of a PKA pathway activator. Methods provided herein may also involve administering to the subject a chemotherapeutic agent or radiotherapy, as described herein. In some embodiments, methods are provided that involve administering to the subject an effective amount of a PKA pathway activator; and administering to the subject a chemotherapeutic agent or a radiotherapy. In some embodiments, the PKA pathway activator increases the concentration of cAMP in a cell. In some embodiments, the methods involve administering to the subject an effective amount of a molecule that increases the concentration of cAMP; and administering to the subject a chemotherapeutic agent or radiotherapy.

In some embodiments, the cancer (e.g., carcinoma) is evaluated for one or more markers or indicators of a cancer stem cell. The cancer (e.g., carcinoma) may be evaluated prior to administration of a compound to induce the cancer (e.g., carcinoma) to undergo a MET or after administration. For example, the cancer may be assessed to determine whether it contains basal-like cancer cells. The cancer may be assessed to determine whether it is resistant to at least one chemotherapeutic agent. The cancer may be assessed to determine whether it is resistant to radiotherapy. Following administration of the molecule to induce a MET, any one or more mesenchymal or epithelial property of the cell, as described herein, may be evaluated to determine whether the treatment was effective.

In some embodiments, methods for assessing a subject having a cancer (e.g., carcinoma) are provided. The methods may be used to determine if the subject is a candidate for a particular treatment, to monitor progression of the cancer, or to monitor effectiveness of the treatment. The methods may involve obtaining a sample of the cancer from the subject and determining the mesenchymal or epithelial state of cells within the sample. In some embodiments, the methods involve determining activity of PKA in the cell. For example, the methods may involve assessing the levels of expression of a cell marker associated with the mesenchymal or epithelial state, the concentration of cAMP in the cell, and/or the activity of PKA in the cell. Any of such assessment can be compared to control cell or cell that have not undergone a MET.

Some aspects of the disclosure are methods for treating a subject having, or suspected of having, cancer (e.g., carcinoma) comprising administering to the subject an effective amount of a compound that selectively targets cancer stem cells. In some embodiments, the treatment methods of the disclosure involve treatment of a subject having (e.g., harboring) or at risk of having a cancer stem cell (CSC) and/or a CSC-dependent tumor.

Some aspects of the disclosure provide methods for treating cancer in a subject that was previously identified as having and/or treated for low PKA activity. Such subjects are treated by administration of a chemotherapeutic agent or radiotherapy, as described herein.

Some aspects of the disclosure provide methods for treating cancer in a subject that was previously treated with a chemotherapeutic agent. Such subjects are treated by administration of a molecule that induces the MET, such as a PKA pathway activator, as described herein.

As used herein, a subject may be a mammal, including but not limited to a dog, cat, horse, cow, pig, sheep, goat, chicken, rodent, or primate. In some embodiments, subjects are human subjects. The human subject may be a pediatric or adult subject. In some embodiments the adult subject is a geriatric subject. Whether a subject is deemed "at risk" of having cancer (e.g., a carcinoma) is a determination that may be within the discretion of the skilled practitioner caring for the subject. Any suitable diagnostic test and/or criteria can be used. For example, a subject may be considered "at risk" of having cancer if (i) the subject has a mutation, genetic polymorphism, gene or protein expression profile, and/or presence of particular substances in the blood, associated with increased risk of developing or having cancer relative to other members of the general population not having mutation or genetic polymorphism; (ii) the subject has one or more risk factors such as having a family history of cancer, having been exposed to a carcinogen or tumor-promoting agent or condition, e.g., asbestos, tobacco smoke, aflatoxin, radiation, chronic infection/inflammation, etc., advanced age; (iii) the subject has one or more symptoms of cancer, etc. In some embodiments, if the compound is one that has been previously (prior to the instant disclosure) administered to subjects for purposes other than treating cancer, e.g., for treatment of a condition other than cancer, the subject is not one to whom the compound would normally be administered for such other purpose and/or the compound is administered in a formulation or at a dose distinct from that known in the art to be useful for such other purpose.

Moreover, as used herein treatment or treating includes amelioration, cure, and/or maintenance of a cure (i.e., the prevention or delay of relapse) of a disorder (e.g, a tumor). Treatment after a disorder has started aims to reduce, ameliorate or altogether eliminate the disorder, and/or its associated symptoms, to prevent it from becoming worse, to slow the rate of progression, or to prevent the disorder from re-occurring once it has been initially eliminated (i.e., to prevent a relapse). Alleviating or ameliorating a target disease/disorder includes delaying the development or progression of the disease, or reducing disease severity. Alleviating the disease does not necessarily require curative results. A suitable dose and therapeutic regimen may vary depending upon the specific compound used, the mode of delivery of the compound, and whether it is used alone or in combination.

As used herein, a therapeutically effective amount generally refers to an amount of a compound that inhibits formation, progression, growth and/or spread (e.g., metastasis) of a tumor or cell. In some embodiments, therapeutically effective amount is an amount of a compound sufficient to inhibit growth of a cell. In some embodiments, therapeutically effective amount is an amount of a compound (e.g., a PKA pathway activator) sufficient to induce a cell (e.g. a CSC) to undergo a MET. In some embodiments, a therapeutically effective amount is an amount of a PKA pathway activator sufficient activate PKA in a cell. In some embodiments, a therapeutically effective amount is an amount of a PKA pathway activator sufficient to increase the cAMP concentration in a cell. In some embodiments, a therapeutically effective amount is an amount sufficient of a PKA pathway activator to increase the sensitivity of a cell to a chemotherapeutic agent.

Methods for establishing a therapeutically effective amount for any compounds (e.g., PKA pathway activators) or compositions described herein will be known to one of ordinary skill in the art. As used herein, pharmacological compositions comprise compounds or compositions that have therapeutic utility, and a pharmaceutically acceptable carrier, e.g., that facilitate delivery of compounds or compositions, in a therapeutically effective amount. The effective amount for any particular application can also vary depending on such factors as the cancer being treated, the particular compound being administered, the size of the subject, or the severity of the disease or condition. One of ordinary skill in the art can empirically determine the effective amount of a particular molecule without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned with the goal of avoiding substantial toxicity and yet effective to treat the particular subject. In some embodiments a useful compound increases the average length of survival, increases the average length of progression-free survival, and/or reduces the rate of recurrence, of subjects treated with the compound in a statistically significant manner.

Subject doses of the compounds described herein typically range from about 0.1 μg to 10,000 mg, more typically from about 1 μg to 8000 mg, e.g., from about 10 μg to 100 mg once or more per day, week, month, or other time interval. Stated in terms of subject body weight, typical dosages in certain embodiments of the disclosure range from about 0.1 μg to 20 mg/kg/day, e.g., from about 1 to 10 mg/kg/day, e.g., from about 1 to 5 mg/kg/day. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. It is often the case that a maximum dose be used, that is, the highest safe dose according to sound medical judgment.

The dose used may be the maximal tolerated dose or a sub-therapeutic dose or any dose there between. Multiple doses of the molecules of the disclosure are also contemplated. When the molecules of the disclosure are administered in combination a sub-therapeutic dosage of either of the molecules, or a sub-therapeutic dosage of both, may be used in the treatment of a subject having, or at risk of developing, cancer. When the two classes of drugs are used together, the cancer medicament may be administered in a sub-therapeutic dose to produce a desirable therapeutic result. A "sub-therapeutic dose" as used herein refers to a dosage which is less than that dosage which would produce a therapeutic result in the subject if administered in the absence of the other agent. Thus, the sub-therapeutic dose of a cancer medicament is one which would not produce the desired therapeutic result in the subject in the absence of the administration of the molecules of the disclosure. Therapeutic doses of cancer medicaments are well known in the field of medicine for the treatment of cancer. These dosages have been extensively described in references such as Remington's Pharmaceutical Sciences; as well as many other medical references relied upon by the medical profession as guidance for the treatment of cancer.

Cancers

The methods described herein have broad application to treating disorders, such as cancer, that are associated with cancer stem cells. Cancer is a disease characterized by uncontrolled or aberrantly controlled cell proliferation and other malignant cellular properties. As used herein, the term cancer includes, but is not limited to, the following types of cancer: breast cancer; biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. In preferred embodiments, cancer is a colon carcinoma, a pancreatic cancer, a breast cancer, an ovarian cancer, a prostate cancer, a squamous cell carcinoma, a cervical cancer, a lung carcinoma, a small cell lung carcinoma, a bladder carcinoma, a squamous cell carcinoma, a basal cell carcinoma, an adenocarcinoma, a sweat gland carcinoma, a sebaceous gland carcinoma, a papillary carcinoma, a papillary adenocarcinoma, a cystadenocarcinoma, a medullary carcinoma, a bronchogenic carcinoma, a renal cell carcinoma, a hepatocellular carcinoma, a bile duct carcinoma, a choriocarcinoma, a seminoma, a embryonal carcinoma, a Wilms' tumor, or a testicular tumor. In one embodiment, cancer is a lung carcinoma. In one embodiment, cancer is a breast carcinoma. In one embodiment, the cancer is a basal-like breast cancer. In one embodiment, the cancer is an ER-negative breast cancer. Other cancers will be known to one of ordinary skill in the art.

Some aspects of the disclosure are methods for treating a subject having, or suspected of having, cancer comprising administering to the subject an effective amount of a PKA pathway activator that induces cancer stem cells to undergo a MET. Other aspects of the disclosure are methods for treating a subject having, or suspected of having, cancer comprising administering to the subject an effective amount of a cancer chemotherapeutic (e.g., doxorubicin, paclitaxel, actinomycin D, camptothecin, and staurosporine) in combination with a PKA pathway activator to induce cancer stem cells to undergo a MET. In some embodiments, a subject is treated with a DNA replication inhibitor (e.g., a DNA intercalating agent) and/or a mitosis inhibitor (e.g., a microtubulin stabilizing agent), and a PKA pathway activator to induce cancer stem cells to undergo a MET. In some embodiments, a subject is treated with a DNA intercalating agent and/or a microtubulin stabilizing agent, and a PKA pathway activator to induce cancer stem cells to undergo a MET. In some embodiments, a subject is treated with a DNA intercalating agent and/or a microtubulin stabilizing agent and a PKA pathway activator. In some embodiments, a subject is treated with paclitaxel in combination with an effective amount of a pharmaceutical composition comprising a PKA pathway activator, e.g., forskolin, colforsin daropate (CD), and cholera toxin, derivatives of any of the foregoing or any other PKA pathway activator. In some embodiments, a subject is treated with doxorubicin in combination with an effective amount of a pharmaceutical composition comprising a PKA pathway activator.

Chemotherapeutic Agents

Non-limiting examples of cancer chemotherapeutics that are useful with methods disclosed herein include Alkylating and alkylating-like agents such as Nitrogen mustards (e.g., Chlorambucil, Chlormethine, Cyclophosphamide, Ifosfamide, and Melphalan), Nitrosoureas (e.g., Carmustine, Fotemustine, Lomustine, and Streptozocin), Platinum agents (i.e., alkylating-like agents) (e.g., Carboplatin, Cisplatin, Oxaliplatin, BBR3464, and Satraplatin), Busulfan, Dacarbazine, Procarbazine, Temozolomide, ThioTEPA, Treosulfan, and Uramustine; Antimetabolites such as Folic acids (e.g., Aminopterin, Methotrexate, Pemetrexed, and Raltitrexed); Purines such as Cladribine, Clofarabine, Fludarabine, Mercaptopurine, Pentostatin, and Thioguanine; Pyrimidines such as Capecitabine, Cytarabine, Fluorouracil, Floxuridine, and Gemcitabine; Spindle poisons/mitotic inhibitors such as Taxanes (e.g., Docetaxel, Paclitaxel) and Vincas (e.g., Vinblastine, Vincristine, Vindesine, and Vinorelbine); Cytotoxic/antitumor antibiotics such anthracyclines (e.g., Daunorubicin, Doxorubicin, Epirubicin, Idarubicin, Mitoxantrone, Pixantrone, and Valrubicin), compounds naturally produced by various species of *Streptomyces* (e.g., Actinomycin, Bleomycin, Mitomycin, Plicamycin) and Hydroxyurea; Topoisomerase inhibitors such as Camptotheca (e.g., Camptothecin, Topotecan and Irinotecan) and Podophyllums (e.g., Etoposide, Teniposide); Monoclonal antibodies for cancer immunotherapy such as anti-receptor tyrosine kinases (e.g., Cetuximab, Panitumumab, Trastuzumab), anti-CD20 (e.g., Rituximab and Tositumomab), and others for example Alemtuzumab, Bevacizumab, and Gemtuzumab; Photosensitizers such as Aminolevulinic acid, Methyl aminolevulinate, Porfimer sodium, and Verteporfin; Tyrosine kinase inhibitors such as Cediranib, Dasatinib, Erlotinib, Gefitinib, Imatinib, Lapatinib, Nilotinib, Sorafenib, Sunitinib, and Vandetanib; serine/threonine kinase inhibitors, (e.g., inhibitors of AbI, c-Kit, insulin receptor family member(s), EGF receptor family member(s), Akt, mTOR (e.g., rapamycin or analogs thereof, direct inhibitors of mTORC1 and/or mTORC2), Raf kinase family, phosphatidyl inositol (PI) kinases such as PI3 kinase, PI kinase-like kinase family members, cyclin dependent kinase family members, Aurora kinase family), growth factor receptor antagonists, and others such as retinoids (e.g., Alitretinoin and Tretinoin), Altretamine, Amsacrine, Anagrelide, Arsenic trioxide, Asparaginase (e.g., Pegaspargase), Bexarotene, Bortezomib, Denileukin diftitox, Estramustine, Ixabepilone, Masoprocol, Mitotane, and Testolactone, Hsp90 inhibitors, proteasome inhibitors, HDAC inhibitors, angiogenesis inhibitors, e.g., anti-vascular endothelial growth factor agents such as Bevacizumab or VEGF-Trap, matrix metalloproteinase inhibitors, pro-apoptotic agents (e.g., apoptosis inducers), anti-inflammatory agents, etc.

In some embodiments, the chemotherapeutic agent comprises a molecule that intercalates into DNA. In some embodiments, the molecule that intercalates into DNA is doxorubicin. In some embodiments, the chemotherapeutic agent comprises a molecule disrupts microtubulin function. In some embodiments, the molecule that disrupts microtubulin function is paclitaxel.

Radiotherapy

Examples of radiotherapy methods that are useful with methods disclosed herein include irradiation with x-rays and other ionizing radiation, such as external beam radiation therapy, brachytherapy, sealed source radiation therapy, systemic radioisotope therapy, or unsealed source radiotherapy.

Pharmaceutical Compositions

It should be appreciated that PKA pathway activators as described herein or any other agent described herein can be mixed with a pharmaceutically acceptable carrier (excipient), including buffer, to form a pharmaceutical composition for use in treating a target disease. In some embodiments, a chemotherapeutic drug is also mixed or combined with a PKA pathway activator and a pharmaceutically acceptable carrier. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The compositions (e.g., compositions comprising a PKA pathway activator) disclosed herein may be administered by any suitable means such as orally, intranasally, subcutaneously, intramuscularly, intravenously, intra-arterially, parenterally, intraperitoneally, intrathecally, intratracheally, ocularly, sublingually, vaginally, rectally, dermally, or as an aerosol. Depending upon the type of condition (e.g., cancer) to be treated, compounds may, for example, be inhaled, ingested or administered by systemic routes. Thus, a variety of administration modes, or routes, are available. The particular mode selected will depend, of course, upon the particular compound selected, the particular condition being treated and the dosage required for therapeutic efficacy. The methods of this disclosure, generally speaking, may be practiced using any mode of administration that is medically acceptable, meaning any mode that produces acceptable levels of efficacy without causing clinically unacceptable adverse effects. Preferred modes of administration are parenteral and oral routes. The term "parenteral" includes subcutaneous, intravenous, intramuscular, intraperitoneal, and intrasternal injection, or infusion techniques. In some embodiments, inhaled medications are of particular use because of the direct delivery to the lung, for example in lung cancer patients. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. Other appropriate routes will be apparent to one of ordinary skill in the art.

According to the methods of the disclosure, compounds (e.g., PKA pathway activators) may be administered in a pharmaceutical composition. Administering the pharmaceutical composition of the present disclosure may be accomplished by any means known to the skilled artisan. In addition to the active agent, the pharmaceutical compositions of the present disclosure typically comprise a pharmaceutically-acceptable carrier. The term "pharmaceutically-acceptable carrier", as used herein, means one or more compatible solid or liquid filler diluents or encapsulating substances which are suitable for administration to a human or lower animal. In preferred embodiments, a pharmaceutically-acceptable carrier is a non-toxic material that does not interfere with the effectiveness of the biological activity of the active ingredients. The term "compatible", as used herein, means that the components of the pharmaceutical compositions are capable of being comingled with the compound of the present disclosure, and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil and oil of theobrama; polyols such as propylene glycol, glycerin, sorbitol, mannitol, and polyethylene glycol; sugar; alginic acid; pyrogen-free water; isotonic saline; phosphate buffer solutions; cocoa butter (suppository base); emulsifiers, such as the Tweens; as well as other non-toxic compatible substances used in pharmaceutical formulation. Wetting agents and lubricants such as sodium lauryl sulfate, as well as coloring agents, flavoring agents, excipients, tableting agents, stabilizers, antioxidants, and preservatives, can also be present.

The pharmaceutically-acceptable carrier employed in conjunction with the compounds of the present disclosure is used at a concentration sufficient to provide a practical size to dosage relationship. The pharmaceutically-acceptable carriers, in total, may comprise from about 60% to about 99.99999% by weight of the pharmaceutical compositions of the present disclosure, e.g., from about 80% to about 99.99%, e.g., from about 90% to about 99.95%, from about 95% to about 99.9%, or from about 98% to about 99%.

Pharmaceutically-acceptable carriers suitable for the preparation of unit dosage forms for oral administration and topical application are well-known in the art. Their selection will depend on secondary considerations like taste, cost, and/or shelf stability, which are not critical for the purposes of the subject disclosure, and can be made without difficulty by a person skilled in the art.

Pharmaceutically acceptable compositions can include diluents, fillers, salts, buffers, stabilizers, solubilizers and other materials which are well-known in the art. The choice of pharmaceutically-acceptable carrier to be used in conjunction with the compounds of the present disclosure is basically determined by the way the compound is to be administered. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the disclosure. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. It will also be understood that the compound can be provided as a pharmaceutically acceptable pro-drug, or an active metabolite can be used. Furthermore it will be appreciated that agents may be modified, e.g., with targeting moieties, moieties that increase their uptake, biological half-life (e.g., pegylation), etc.

The formulations of the disclosure are administered in pharmaceutically acceptable solutions, which may routinely contain pharmaceutically acceptable concentrations of salt, buffering agents, preservatives, compatible carriers, adjuvants, and optionally other therapeutic ingredients.

The compounds of the disclosure may be formulated into preparations in solid, semi-solid, liquid or gaseous forms such as tablets, capsules, powders, granules, ointments, solutions, depositories, inhalants and injections, and usual ways for oral, parenteral or surgical administration. The disclosure also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

When the compounds described herein are used therapeutically, in certain embodiments a desirable route of administration may be by pulmonary aerosol. Techniques for preparing aerosol delivery systems containing compounds are well known to those of skill in the art. Generally, such systems should utilize components which will not significantly impair the biological properties of the peptides (see, for example, Sciarra and Cutie, "Aerosols," in Remington's Pharmaceutical Sciences). Those of skill in the art can readily determine the various parameters and conditions for producing aerosols without resort to undue experimentation.

The compounds of the disclosure may be administered directly to a tissue. Preferably, the tissue is one in which the cancer cells are found. Alternatively, the tissue is one in which the cancer is likely to arise. Direct tissue administration may be achieved by direct injection. The peptides may be administered once, or alternatively they may be administered in a plurality of administrations. If administered multiple times, the peptides may be administered via different routes. For example, the first (or the first few) administrations may be made directly into the affected tissue while later administrations may be systemic.

For oral administration, the compounds can be formulated readily by combining the active compounds with pharmaceutically acceptable carriers well known in the art. Such carriers enable the compounds of the disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art.

All formulations for oral administration should be in dosages suitable for such administration. For buccal administration, the compositions may take the form of tablets or lozenges formulated in conventional manner.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In yet other embodiments, the preferred vehicle is a biocompatible microparticle or implant that is suitable for implantation into the mammalian recipient. Exemplary bioerodible implants that are useful in accordance with this method are described in PCT International Application Publication No. WO 95/24929, entitled "Polymeric Gene Delivery System", which reports on a biodegradable polymeric matrix for containing a biological macromolecule. The polymeric matrix may be used to achieve sustained release of the agent in a subject. In accordance with one aspect of the instant disclosure, the agent described herein may be encapsulated or dispersed within the biocompatible, preferably biodegradable polymeric matrix. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface.

The matrix composition also can be selected not to degrade, but rather, to release by diffusion over an extended period of time.

Both non-biodegradable and biodegradable polymeric matrices can be used to deliver the agents of the disclosure to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the disclosure may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the peptide, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for prophylactic treatment of subjects at risk of developing a recurrent cancer. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

Methods for Identifying Compounds that Induce MET

It should be appreciated that any of the methods, compositions, cells, and vectors provided herein can be used to identify compounds that induce a MET in a cell. In some aspects, the present disclosure provides methods of identifying a candidate compound for inducing a MET in a cancer stem cell comprising (i) contacting cells with a test compound, and (ii) determining whether the test compound induces an increase in at least one marker or indicator of an epithelial phenotype indicates that the test compound is a candidate compound for inducing a MET in a cancer stem cell. In some embodiments, the cells that are contacted with a test compound express one or more cancer stem cell markers.

Some aspects of the disclosure provide methods for testing and identifying candidate compounds or compositions (e.g., PKA pathway inhibitors) that induce a mesenchymal-to-epithelial transition in a population of cells. Such methods may be referred to as "screening" methods. Screening may be carried out in vitro or in vivo using any of the assays disclosed herein. As described herein, compounds or compositions that substantially affect the MET transition can be uncovered using the disclosed screening methods. In some embodiments, the test compound induces an increase in intracellular cAMP levels. In some embodiments, the test compound activates a cAMP adenylate cyclase. In some embodiments, the test compound inhibits a phosphodiesterase that hydrolyzes cAMP. In some embodiments, the test compound is an activator of PKA.

As used herein, compounds or compositions may in some cases be referred to as test agents. In some embodiments the effect of an identified compound on CSCs, non-CSCs, or a combination thereof may be assessed. In some embodiments the effect of an identified compound on test cells, control cells, or a combination thereof may be assessed. A compound that exhibits a desired effect, e.g., induces an MET program in CSCs, may be identified.

In some embodiments, compounds are contacted with cells at a predetermined dose. In one embodiment the dose may be about up to 1 nM. In another embodiment the dose may be between about 1 nM and about 100 nM. In another embodiment the dose may be between about 100 nM and about 10 uM. In another embodiment the dose may be at or above 10 uM. Following incubation for an appropriate time, optionally a predetermined time, the effect of compounds or composition on the growth and/or survival of the test cell is determined by an appropriate method known to one of ordinary skill in the art. Cells can be contacted with compounds for various periods of time. In certain embodiments cells are contacted for between 12 hours and 20 days, e.g., for between 1 and 10 days, for between 2 and 5 days, or any intervening range or particular value. Cells can be contacted transiently or continuously. The following provides further examples of test compounds and is not meant to be limiting. Those of ordinary skill in the art will recognize that there are numerous additional types of suitable test compounds that may be tested using the methods, cells, and/or animal models of the disclosure. Test compounds can be small molecules (e.g., compounds that are members of a small molecule chemical library). The compounds can be small organic or inorganic molecules of molecular weight below about 3,000 Daltons. The small molecules can be, e.g., from at least about 100 Da to about 3,000 Da (e.g., between about 100 to about 3,000 Da, about 100 to about 2,500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The small molecules can be natural products, synthetic products, or members of a combinatorial chemistry library. A set of diverse molecules can be used to cover a variety of functions such as charge, aromaticity, hydrogen bonding, flexibility, size, length of side chain, hydrophobicity, and rigidity. Combinatorial techniques suitable for synthesizing small molecules are known in the art (e.g., as exemplified by Obrecht and Villalgrodo, Solid-Supported Combinatorial and Parallel Synthesis of Small-Molecular-Weight Compound Libraries, Pergamon-Elsevier Science Limited (1998)), and include those such as the "split and pool" or "parallel" synthesis techniques, solid-phase and solution-phase techniques, and encoding techniques (see, for example, Czarnik, A. W., Curr. Opin. Chem. Biol. (1997) 1:60). In addition, a number of small molecule libraries are publicly or commercially available (e.g., through Sigma-Aldrich, TimTec (Newark, Del.), Stanford School of Medicine High-Throughput Bioscience Center (HTBC), and ChemBridge Corporation (San Diego, Calif.).

Compound libraries screened using the new methods can comprise a variety of types of test compounds. A given library can comprise a set of structurally related or unrelated test compounds. In some embodiments, the test compounds are peptide or peptidomimetic molecules. In some embodiments, test compounds include, but are not limited to, peptide analogs including peptides comprising non-naturally occurring amino acids, phosphorous analogs of amino acids, amino acids having non-peptide linkages, or other small organic molecules. In some embodiments, the test compounds are peptidomimetics (e.g., peptoid oligomers, e.g., peptoid amide or ester analogues, D-peptides, L-peptides, oligourea or oligocarbamate); peptides (e.g., tripeptides, tetrapeptides, pentapeptides, hexapeptides, heptapeptides, octapeptides, nonapeptides, decapeptides, or larger, e.g., 20-mers or more); cyclic peptides; other non-natural peptide-like structures; and inorganic molecules (e.g., heterocyclic ring molecules). In some embodiments a polypeptide comprises an affibody, adnectin, DARPin, knottin, anticalins, or steffin. The polypeptide, e.g., affibody, adnectin, DARPin, knottin, anticalins, or steffin, may be designed or selected to bind to a target of interest. Test compounds can also be nucleic acids.

The test compounds and libraries thereof can be obtained by systematically altering the structure of a first "hit" compound, also referred to as a lead compound, that has a desired effect (e.g., induces a MET program in a CSC), and correlating that structure to a resulting biological activity (e.g., a structure-activity relationship study).

Such libraries can be obtained using any of the numerous approaches in combinatorial library methods known in the art, including: peptoid libraries (libraries of molecules having the functionalities of peptides, but with a novel, non-peptide backbone which are resistant to enzymatic degradation but which nevertheless remain bioactive; see, e.g., Zuckermann, et al., J. Med. Chem., 37:2678-85 (1994)); spatially addressable parallel solid phase or solution phase libraries; synthetic library methods requiring deconvolution; the "one-bead one-Compound" library method; and synthetic library methods using affinity chromatography selection (Lam, Anticancer Drug Des. 12:145 (1997)). Examples of methods for the synthesis of molecular libraries can be found in the art, for example in: DeWitt et al., Proc. Natl. Acad. Sci. USA, 90:6909 (1993); Erb et al., Proc. Natl. Acad. Sci. USA, 91:11422 (1994); Zuckermann et al., J. Med. Chem., 37:2678 (1994); Cho et al., Science, 261:1303 (1993); Carrell et al., Angew. Chem. Int. Ed. Engl., 33:2059 (1994); Carell et al., Angew. Chem. Int. Ed. Engl., 33:2061 (1994); and in Gallop et al., J. Med. Chem., 37:1233 (1994). Libraries of compounds can be presented in solution (e.g., Houghten (1992) Biotechniques, 13:412-421), or on beads (Lam (1991) Nature, 354:82-84), chips (Fodor (1993) Nature, 364:555-556), bacteria (Ladner, U.S. Pat. No. 5,223, 409), spores (Ladner, U.S. Pat. No. 5,223,409), plasmids (Cull et al. (1992) Proc. Natl. Acad. Sci. USA, 89:1865-1869) or on phage (Scott and Smith (1990) Science, 249: 386-390; Devlin (1990) Science, 249:404-406; Cwirla et al. (1990) Proc. Natl. Acad. Sci. USA, 87:6378-6382; Felici (1991) J. Mol. Biol., 222:301-310; Ladner, supra.).

In some embodiments, the methods of the disclosure are used to screen "approved drugs". An "approved drug" is any compound (which term includes biological molecules such as proteins and nucleic acids) which has been approved for use in humans by the FDA or a similar government agency in another country, for any purpose.

Applicants reserve the right to exclude any particular compound, compounds, or compound class from the scope of "test compound" and/or from the compositions and methods of the disclosure. In some embodiments the "test compound" is not a compound found in, or known in the art as an ingredient of, tissue culture medium, e.g., a compound provided for purposes of culturing the cells. In some embodiments the test compound may be one found in, or known in the art as an ingredient of, tissue culture medium, but is used as a test compound at concentrations differing from those at which it is typically used as an ingredient of tissue culture medium. In some embodiments the compound is not a compound known in the art as being useful for treating cancer and/or for reducing side effects associated with chemotherapy.

Certain results of the compound identification and characterization methods disclosed herein may be clinically beneficial, such as if the compound induces a MET program in a CSC, as those disclosed herein. Still other clinically beneficial results include: (a) inhibition or arrest of primary tumor growth, (b) inhibition of metastatic tumor growth and (c) extension of survival of a test subject. Compounds with clinically beneficial results are potential chemotherapeutics, and may be formulated as such.

Compounds identified as inducing an MET program in CSCs may be referred to herein as lead compounds and can be selected and systematically altered, e.g., using rational design, to optimize binding affinity, avidity, specificity, or other parameters. Such optimization can also be screened for using the methods described herein. Thus, one can screen a first library of small molecules using the methods described herein, identify one or more compounds that are "hits" or "leads" by virtue of, for example, their ability to induce an MET program, and subject those hits to systematic structural alteration to create a second library of compounds (e.g., refined lead compounds) structurally related to the hit. The second library can then be screened using the methods described herein. A refined lead compound can be produced by modifying the lead compound to achieve (i) improved potency, (ii) decreased toxicity (improved therapeutic index); (iii) decreased side effects; (iv) modified onset of therapeutic action and/or duration of effect; and/or (v) modified pharmacokinetic parameters (absorption, distribution, metabolism and/or excretion). The lead compound could be, e.g., purified from natural sources or chemically synthesized. Modifications could be made directly to the lead compound, or refined lead compounds (e.g., derivatives) could be synthesized from suitable starting materials.

In certain embodiments of the disclosure, a compound identified using the inventive methods induces a MET program in CSCs as assessed by monitoring one or more mesenchymal and/or epithelial properties of the CSCs, as described herein. The mesenchymal and/or epithelial cell property, for example expression of a cell surface marker (e.g. E-cadherin) can be compared in CSCs that have been exposed to a test compound relative to the same property in control cells or cells that have not been exposed to the test compound. For example, the expression of a mesenchymal-specific protein may be about 2, 3, 4, 5, 6, 7, 8, 9, 10, 15, 20, 30, 40, 50, 100, 150-fold lower in cells that have been exposed to a test compound compared to cells that have not been exposed to the test compound. In some embodiments, the expression of a mesenchymal-specific protein may be about 2, 3, 4, 5, 6, 7, 8, 9, 10, 15, 20, 30, 40, 50, 100, 150-fold lower in cells that have undergone a MET compared to cells that have not undergone an MET. For example, the expression of an epithelial-specific protein may be about 2, 3, 4, 5, 6, 7, 8, 9, 10, 15, 20, 30, 40, 50, 100, 150-fold higher in cells that have been exposed to a test compound compared to cells that have not been exposed to the test compound. In some embodiments, the expression of an epithelial-specific protein may be about 2, 3, 4, 5, 6, 7, 8, 9, 10, 15, 20, 30, 40, 50, 100, 150-fold higher in cells that have undergone a MET compared to cells that have not undergone an MET.

In some cases it is desirable to determine the potency of a compound of the disclosure using a dose response assay. Methods for determining the potency of compounds or compositions are well known in the art. In some embodiments, potency is characterized as a half maximal effective concentration (EC50) of a compound. As used herein, the term half maximal effective concentration (EC50) refers to the concentration of a compound that induces a response in a biological system (e.g., one or more cells) halfway between the baseline response (e.g., no compound) and the maximal response. EC50 is commonly used in the art as a measure of compound potency (e.g., drug potency). The EC50 of a dose response curve represents the concentration of a compound where 50% of its maximal effect (also referred to as maximal response) is observed. EC50 is related to the half maximal inhibitory concentration (IC50), which is often used as a measure of inhibition by a compound (50% inhibition) in a biological assay (e.g., cell growth or viability) or biochemical assay. Methods for determining EC50/IC50 values are well known in the art.

A variety of techniques useful for determining the structures of compounds are known and can be used in the methods described herein (e.g., NMR, mass spectrometry, gas chromatography equipped with electron capture detectors, fluorescence, and absorption spectroscopy).

Assays for determining whether a test compounds has induced a cell or population of cells to undergo a MET may be conducted in vitro or ex vivo and/or in vivo using cells (e.g., cancer stem cells identified or generated using any suitable method, cancer cells, cancer cell lines, etc.) and methods of the disclosure or any suitable system for testing efficacy. For example, a test compound may be administered to a nonhuman subject to which has been administered (e.g., implanted or injected with) a plurality of the test cells described herein, e.g., a number of cancer stem cells sufficient to induce the formation of one or more tumors (e.g., CSC-dependent tumors), a tumor xenograft, etc. The nonhuman subject can be, e.g., a rodent (e.g., a mouse). Optionally the nonhuman subject is immunocompromised, e.g., a Nude, SCID, NOD-SCID, Rag1-/-, and Rag2-/- mouse. In some embodiments the test subject is a cancer-prone animal, e.g., an animal model harboring an activated oncogene and/or lacking a tumor suppressor gene, or an animal that has been exposed to a condition, compound, or stimulus that renders the animal prone to develop cancer. As used herein, a non-human test subject may also be referred to as an animal host.

Assay systems comprising test cells, control cells, and one or more test compounds, e.g., 10, 100, 1000, 10,000, or more test compounds, wherein the cells and test agents are arranged in one or more vessels in a manner suitable for assessing effect of the test compound(s) on the cells, are aspects of the disclosure. Typically the vessels contain a suitable tissue culture medium, and the test compounds are present in the tissue culture medium. One of skill in the art can select a medium appropriate for culturing a particular cell type. In some embodiments, a medium is free or essentially free of serum or tissue extracts while in other embodiments such a component is present. In some embodiments, cells are cultured on a plastic or glass surface. In some embodiments cells are cultured on or in a material comprising collagen, laminin, Matrigel®, or a synthetic material, e.g., a synthetic hydrogel, intended to provide an environment that resembles in at least some respects the extracellular environment found in many tissues. In some embodiments test and/or control cells are cultured with non-cancerous stromal cells. In some embodiments test and/or control cells are cultured with fibroblasts. In some embodiments test and/or control cells are cultured in three-dimensional culture matrix. In some embodiments, test cells and control cells are maintained in separate vessels (e.g., separate wells of a microwell plate) under substantially identical conditions.

Vectors

Aspects of the disclosure relate to a vector for use in methods, cells, and/or compositions provided herein. As used herein, a "vector" may be any of a number of nucleic acid molecules into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes or portions thereof. Vectors may be used for a variety of purposes. For example, a vector may be used to deliver a reporter or other nucleic acid construct to a cell. In some embodiments, a vector comprises components that when expressed in a cell provide an indication of the state of the cell (e.g., mesenchymal state, epithelial state). For example, a vector comprise a reporter gene coupled to a promoter responsive to a transcription factor that is a target of PKA (e.g., CREB), such that the reporter can be used to assay for changes in PKA activity that relate to the mesenchymal or epithelial state of the cell. In some embodiments, a vector is used to generate a cell related to methods provided herein, such as a stable cancer cell line. In some embodiments, a vector is used to deliver nucleic acids to a cell. In some embodiments, the nucleic acids delivered to a cell are inhibitory nucleic acids (e.g., shRNAs, miRNA) that target one or more components of a PKA pathway. In some embodiments, the inhibitory nucleic acid target and inhibits the expression of a G-protein coupled receptor that associates with a $G_i$ alpha subunit. In some embodiments, the inhibitory nucleic acid target and inhibits the expression of a phosphodiesterase.

A vector as described herein, is one in which a desired nucleic acid encoding a regulatory sequence (e.g. a promoter sequence) of a gene may be inserted, e.g., by restriction and ligation, such that it is operably joined to a reporter gene that will be expressed as an RNA transcript. Vectors may further contain one or more marker sequences suitable for use in the identification of cells that have or have not been transformed or transfected with the vector. Markers include, for example, genes encoding proteins that increase or decrease either resistance or sensitivity to antibiotics or other compounds, genes that encode enzymes whose activities are detectable by standard assays known in the art (e.g., β-galactosidase or alkaline phosphatase), and genes that visibly affect the phenotype of transformed or transfected cells, tissues, hosts, colonies or plaques (e.g., green fluorescent protein).

As used herein, a coding sequence of a reporter gene and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide. It will be appreciated that a coding sequence need not encode a protein but may instead, for example, encode a functional RNA such as an shRNA.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include leader or signal sequences. The choice and design of an appropriate vector is within the ability and discretion of one of ordinary skill in the art. One of skill in the art will be aware of appropriate regulatory sequences for expression of interfering RNA, e.g., shRNA, miRNA, etc.

In some aspects of the disclosure, the regulatory sequences are derived from a gene of interest, for example a gene encoding a cell surface protein that is associated with the mesenchymal or the epithelial state. In some embodiments, the regulatory sequences include the promoter region of a gene a cell surface protein that is associated with the mesenchymal or the epithelial state. In some embodiments, the cell surface protein is associated with the epithelial state. In some embodiments, the cell surface protein is E-cadherin. In such embodiments, the vector includes a promoter of E-cadherin that is operably linked to a gene encoding a reporter protein. When such a vector is present in a cell, activation of the E-cadherin promoter results in expression of the reporter protein that can be subsequently detected to evaluate the state of the cell. In some embodiments, expression of the reporter protein indicates the cell is in an epithelial-like state. Non-limiting examples of reporter proteins that are compatible for practice of the instant disclosure include any fluorescent protein (e.g., green fluorescent protein (GFP), red fluorescent protein (RFP), yellow fluorescent protein (YFP), mCherry, etc.), β-galactosidase, β-glucuronidase, alkaline phosphatase, drug resistance protein (e.g., neomycin phosphotransferase), and any luciferase (e.g. a Firefly luciferase, a bacterial luciferase). In some embodiments, the reporter protein is luciferase. In some embodiments, the vector comprises the E-cadherin promoter operably linked to a gene encoding luciferase. In such embodiments, activation of the E-cadherin promoter results in expression of luciferase.

In some embodiments, a virus vector for delivering a nucleic acid molecule is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses (e.g., Xiang et al., Virology 219:220-227, 1996; Eloit et al., J. Virol. 7:5375-5381, 1997; Chengalvala et al., Vaccine 15:335-339, 1997), a modified retrovirus (Townsend et al., J. Virol. 71:3365-3374, 1997), a nonreplicating retrovirus (Irwin et al., J. Virol. 68:5036- 5044, 1994), a replication defective Semliki Forest virus (Zhao et al., Proc. Natl. Acad. Sci. USA 92:3009-3013, 1995), canarypox virus and highly attenuated vaccinia virus derivative (Paoletti, Proc. Natl. Acad. Sci. USA 93:11349-11353, 1996), non-replicative vaccinia virus (Moss, Proc. Natl. Acad. Sci. USA 93:11341-11348, 1996), replicative vaccinia virus (Moss, Dev. Biol. Stand. 82:55-63, 1994), Venzuelan equine encephalitis virus (Davis et al., J. Virol. 70:3781-3787, 1996), Sindbis virus (Pugachev et al., Virology 212:587-594, 1995), lentiviral vectors (Naldini L, et al., Proc Natl Acad Sci USA. 1996 Oct. 15; 93(21):11382-8) and Ty virus-like particle (Allsopp et al., EMr. J Immunol 26:1951-1959, 1996).

Another virus useful for certain applications is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other useful viral vectors are based on non-cytopathic eukaryotic viruses in which non-essential genes have been replaced with the gene of interest. Non-cytopathic viruses include certain retroviruses, the life cycle of which involves reverse transcription of genomic viral RNA into DNA with subsequent proviral integration into host cellular DNA. In general, the retroviruses are replication-deficient (i.e., capable of directing synthesis of the desired transcripts, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E J. Ed. "Methods in Molecular Biology," vol. 7, Humana Press, Inc., Clifton, N.J. (1991).

Various techniques may be employed for introducing nucleic acid molecules of the disclosure into cells, depending on whether the nucleic acid molecules are introduced in vitro or in vivo in a host. Such techniques include transfection of nucleic acid molecule-calcium phosphate precipitates, transfection of nucleic acid molecules associated with DEAE, transfection or infection with the foregoing viruses including the nucleic acid molecule of interest, liposome-mediated transfection, and the like. Other examples include: N-TER™ Nanoparticle Transfection System by Sigma-Aldrich, FectoFly™ transfection reagents for insect cells by Polyplus Transfection, Polyethylenimine "Max" by Polysciences, Inc., Unique, Non-Viral Transfection Tool by Cosmo Bio Co., Ltd., Lipofectamine™ LTX Transfection Reagent by Invitrogen, SatisFection™ Transfection Reagent by Stratagene, Lipofectamine™ Transfection Reagent by Invitrogen, FuGENE® HD Transfection Reagent by Roche Applied Science, GMP compliant in vivo-jetPEI™ transfection reagent by Polyplus Transfection, and Insect Gene-Juice® Transfection Reagent by Novagen.

As used herein, the terms "approximately" or "about" in reference to a number are generally taken to include numbers that fall within a range of 1%, 5%, 10%, 15%, or 20% in either direction (greater than or less than) of the number unless otherwise stated or otherwise evident from the context (except where such number would be less than 0% or exceed 100% of a possible value).

All references described herein are incorporated by reference for the purposes described herein.

EXAMPLES

Example 1: Identification of Factors that Induce a Mesenchymal-to-Epithelial Transition in Mesenchymal Cancer Stem Cells by High-Throughput Screening The epithelial-to-mesenchymal transition (EMT) represents a program that leads to the formation of both normal and neoplastic epithelial stem cells, the latter representing cells that exhibit CSC-like properties. Epithelial cells, including those in normal mammary gland, for example, and by extension in other epithelial organs, employ components of the EMT program as the main route for entering into the SC state.

Activation of the EMT program results in the formation of epithelial cells that have stem-like properties. In the context of cancer, the resulting mesenchymal cells have enhanced tumor-initiating ability, mammosphere-forming ability (in the case of breast cancer), and exhibit cell-surface marker and gene expression profiles similar to both normal stem cells and cancer stem cells (CSCs). Moreover, the CSCs that are generated when neoplastic cells undergo an EMT have been shown to be more resistant to various chemotherapeutic drugs that are capable of eliminating the bulk epithelial cell populations of primary tumors. Due to a difficulty of eliminating these metastatic and highly resistant cells, strategies were developed herein to induce the reverse transition of mesenchymal CSCs toward an epithelial state.

Figure 2:
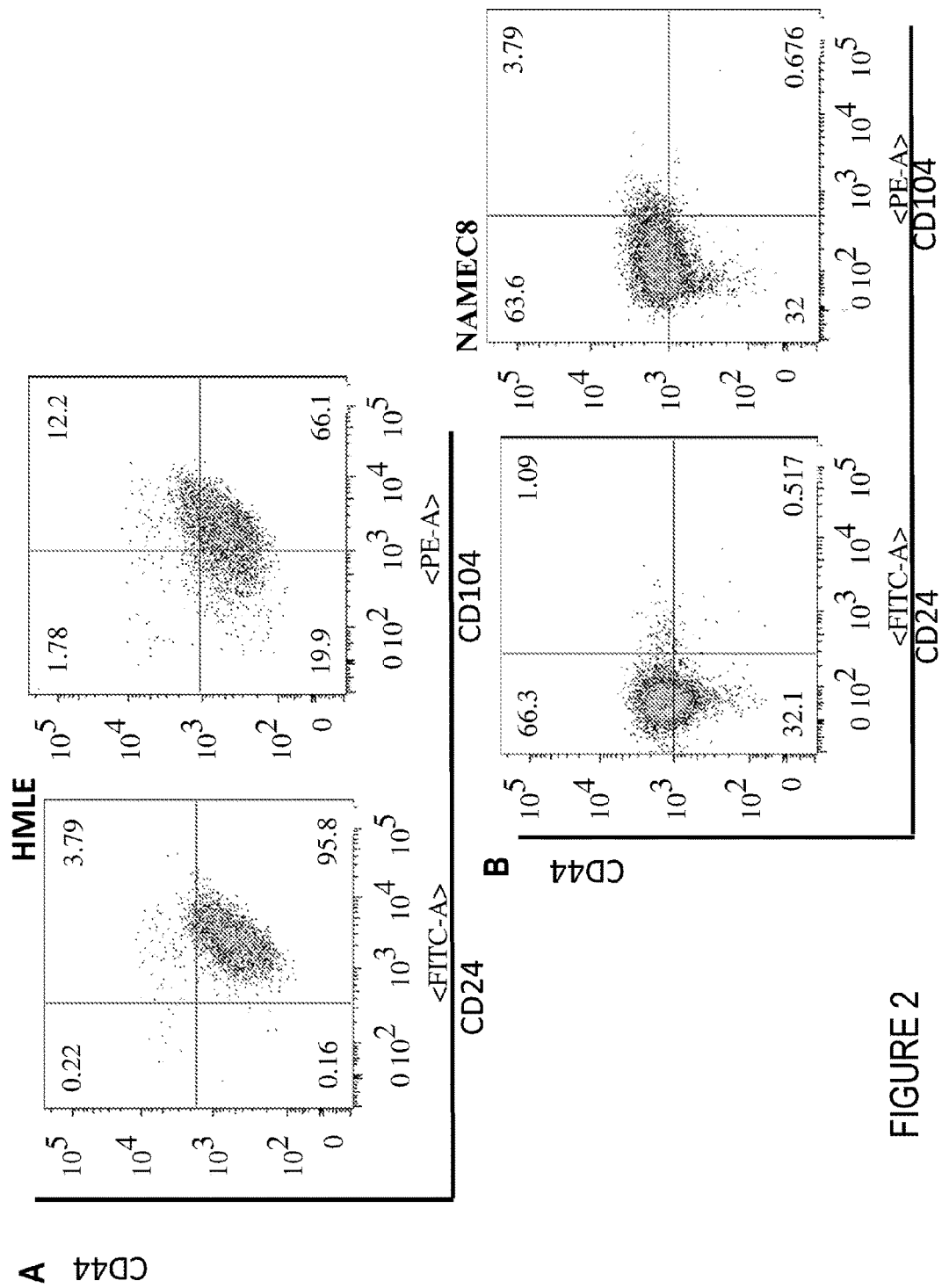
FIGS. 2A and 2B show flow cytometric analysis of populations of (A) immortalized and partially transformed human mammary epithelial cells (HMLE) and (B) a subpopulation of HMLE cells that are naturally arising mesenchymal cells (NAMEC).

The experimental model cells for the work described herein include experimentally immortalized human mammary epithelial cells (HMLE) and their mesenchymal counterparts. These mesenchymal cells exhibited a $CD44^{hi}CD24^{lo}$ expression marker profile and were referred to as naturally arising mesenchymal cells (NAMEC cells). Through immunofluorescence, it has been established that these HMLE and NAMEC cells express cytokeratins 5 and p63 among other basal markers, and hence recapitulate a number of traits of human basal-like breast cancer cells. Intratumoral heterogeneity is also modeled appropriately in the HMLE system with different subpopulations that possess various mesenchymal/SC properties. Upon transformation with an introduced mutant RAS oncogene, NAMECs exhibited a ~100-fold higher tumor-initiating ability than populations of parental HMLE cells transformed in parallel. RAS-transformed HMLE cells, when transplanted orthotopically into the fat pads of immunocompromised mice, formed benign, well-differentiated tumors containing lobular structures, whereas those arising from NAMEC cells formed aggressive, poorly differentiated tumors that were more invasive and metastatic (FIGS. 1C and 1D). These phenotypes of transformed/neoplastic cells reflected the preexisting state of differentiation of the immortalized cells observed in vitro prior to their transformation by RAS. As shown in FIG. 1A and FIG. 2A, HMLE cells exhibited an epithelial cobblestone-like morphology with well-defined cell junctions and expressed a $CD44^{lo}$ $CD24^{hi}$ non-SC, cell-surface marker profile. In contrast, NAMEC cells exhibited mesenchymal properties, did not form epithelial islands, had spindle-shaped morphology, and expressed the $CD44^{hi}$ $CD24^{lo}$ SC-like marker profile (FIG. 1B and FIG. 2B).

NAMEC cells, as described above, recapitulate a number of traits of therapy resistant, metastatic human basal-like breast cancer cells. In effort to identify factors that may stimulate differentiation of CSCs by inducing a mesenchymal-to-epithelial transition and render the NAMEC cells less tumorigenic and epithelial cell-like, a high-throughput screen was performed.

Figure 3A:
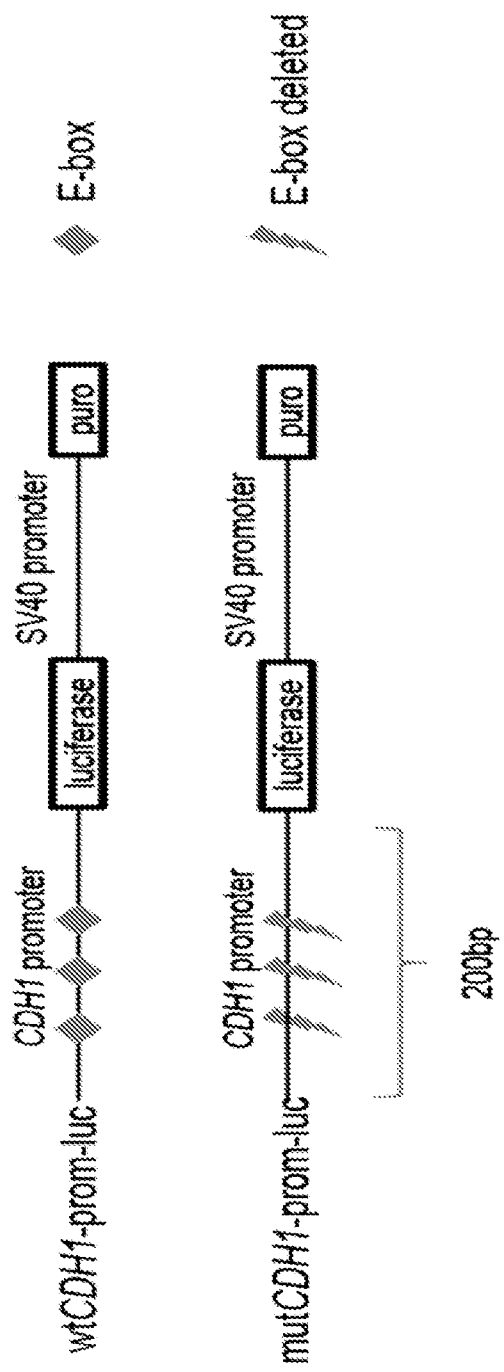
FIGS. 3A-3C depict a screen to identify factors that induce a mesenchymal to epithelial transition.
Figure 3B:
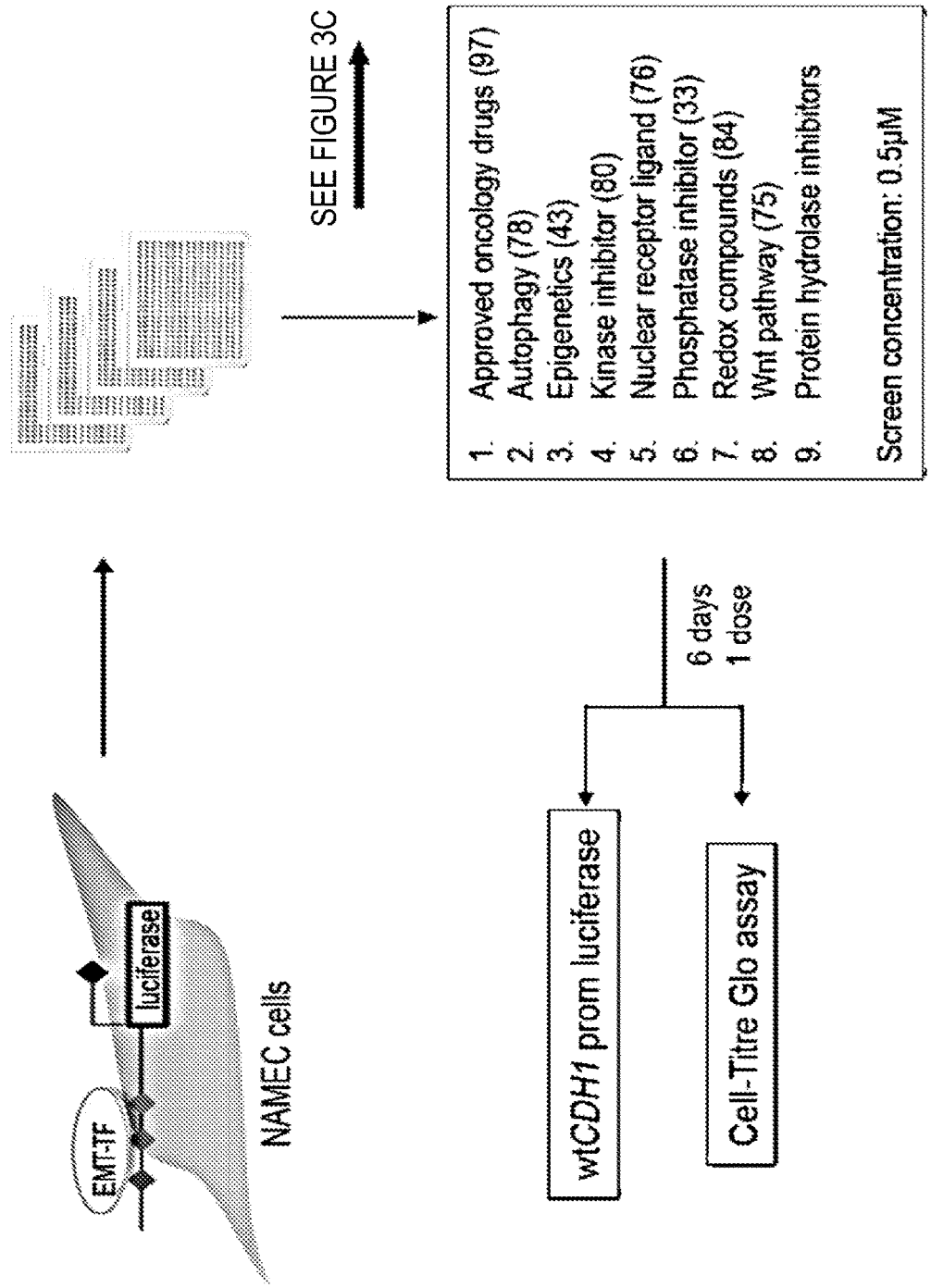
Figure 3C:
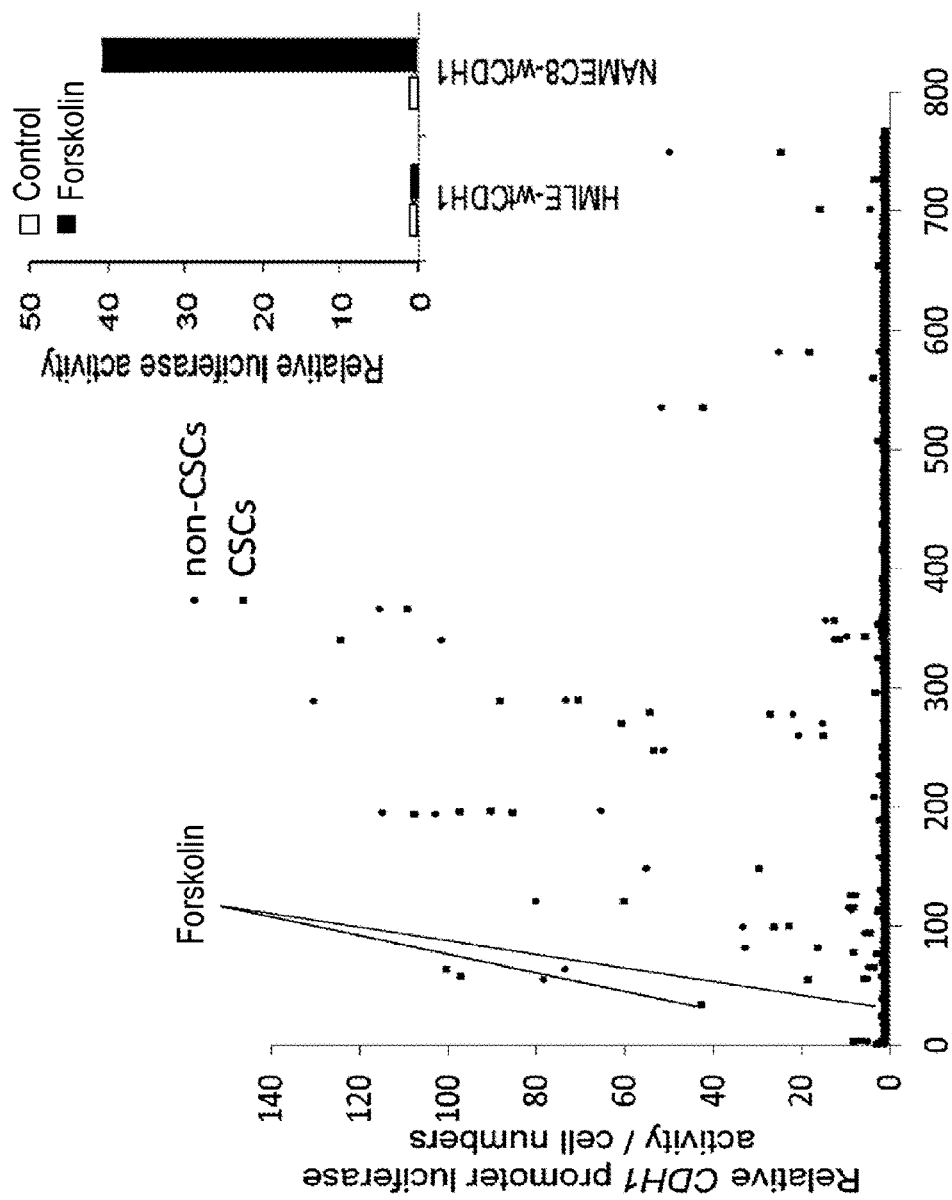

E-cadherin (also known as CDH1) is an epithelial cell marker that is highly down-regulated in NAMEC cells. The promoter region of E-cadherin/CDH1 was chosen to drive expression of the reporter gene Firefly luciferase. As presented schematically in FIG. 3, a stably-expressed lentiviral construct was generated with the E-box containing E-cadherin/CDH1 promoter transcriptionally fused to the gene encoding luciferase ("WT Luc"). A second stably-expressed lentiviral construct was generated in which the E-box sequences were removed ("Mut Luc"). The lentiviral constructs were expressed in NAMEC cells for the in vitro high-throughput screen. As shown in FIG. 3, cells were plated in 384-well plates and exposed to a standard concentration of 0.5 µM of each of the tested compounds for 6 days. The test compounds included approved oncology drugs, kinase inhibitors, nuclear receptor ligands, phosphatase inhibitors, protein hydrolase inhibitors, and compounds involved in autophagy, epigenetic regulation, redox, and the Wnt pathway. After 6 days, luciferase activity was quantified using a luminometer and adjusted for cell number, as measured by Cell-Titer Glo (Promega).

Figure 4:
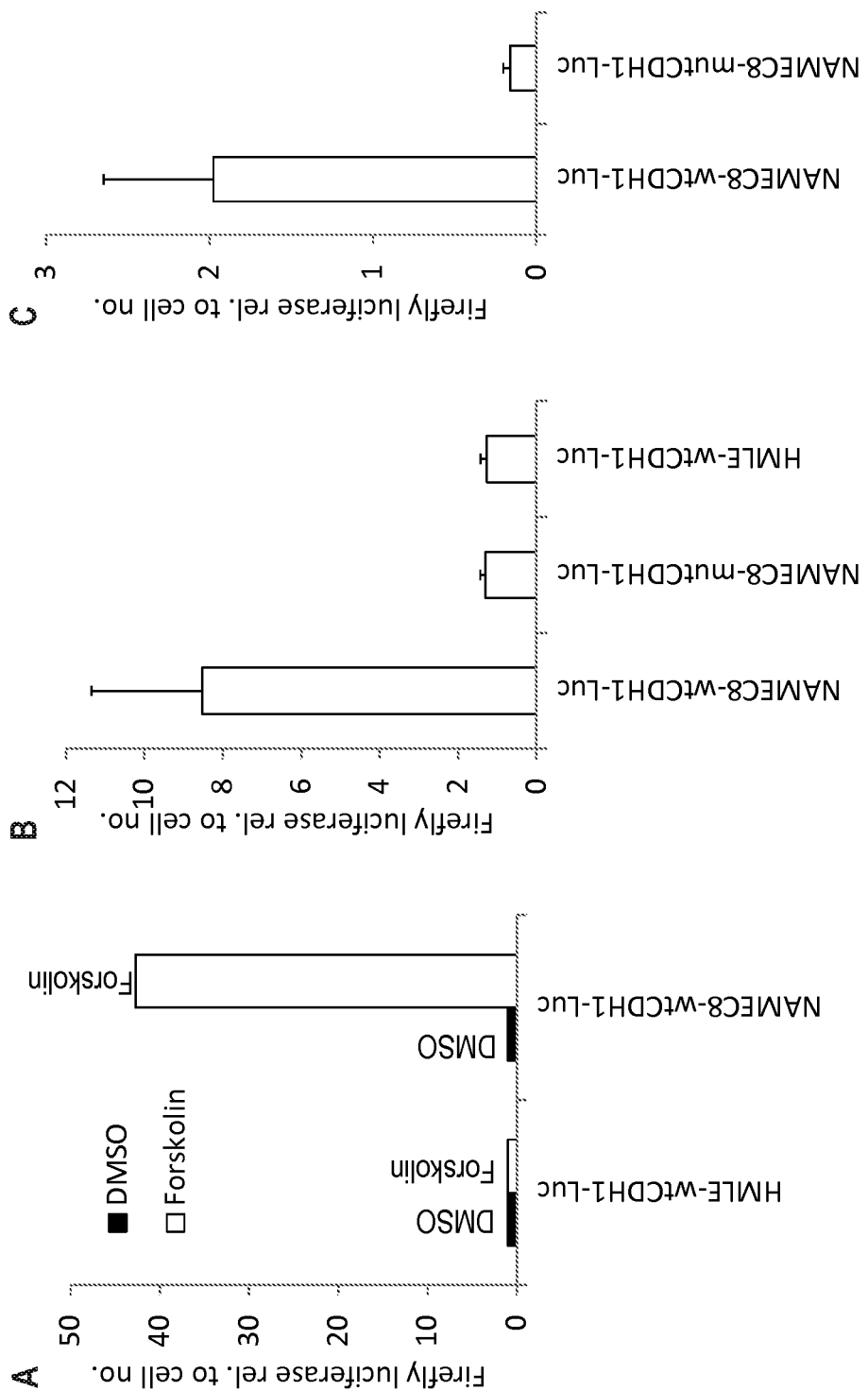
FIGS. 4A-4C present candidate molecules identified in a high-throughput screen that induced MET in NAMEC cells expressing the E-cadherin-luciferase construct.

After testing more than 400 compounds, forskolin, an activator of adenylate cyclase, was identified as able to induce transcription of the E-cadherin reporter by 40-fold compared to the control after normalization to cell number (FIG. 4A). The results from the screen were validated to confirm the ability of forskolin and cholera toxin, another activator of adenylate cyclase, to induce luciferase expression (FIGS. 4B and 4C).

Figures 5G, 5H, 5I:
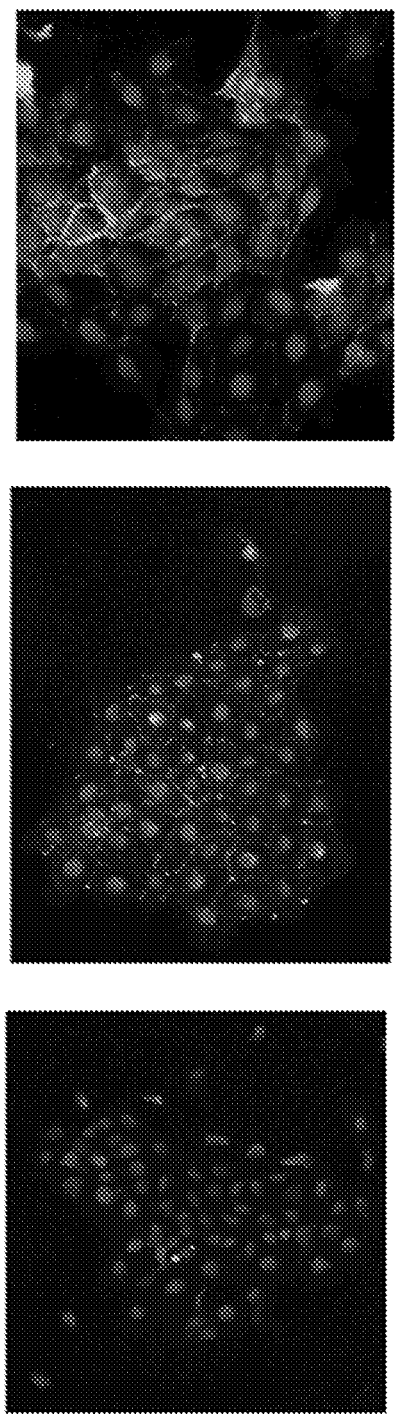

Example 2: Characterization of Factors that Induced a Mesenchymal-to-Epithelial Transition in Mesenchymal Cancer Stem Cells To further characterize the effects of forskolin and cholera toxin in inducing the MET in NAMEC cells, the cells were treated with 100 µg/ml cholera toxin or 10 µM forskolin over 12 days, replenishing the media containing the cholera toxin or forskolin every other day (EOD). Following this treatment, the NAMEC cells attained a cobblestone-like epithelial morphology (FIGS. 5A-5C), and expressed junctional E-cadherin, as shown by fluorescent microscopy using an anti-E-cadherin detection antibody (FIGS. 5G-5I). Under these conditions, 95% of cells expressing the SC-like $CD44^{hi}CD24^{lo}$ marker profile reverted to expressing the non-SC $CD44^{lo}CD24^{hi}$ profile (FIGS. 5G-5F). Similar results were obtained when using Ras-transformed NAMEC cells when treated with these compounds (data not shown).

Figure 6A:
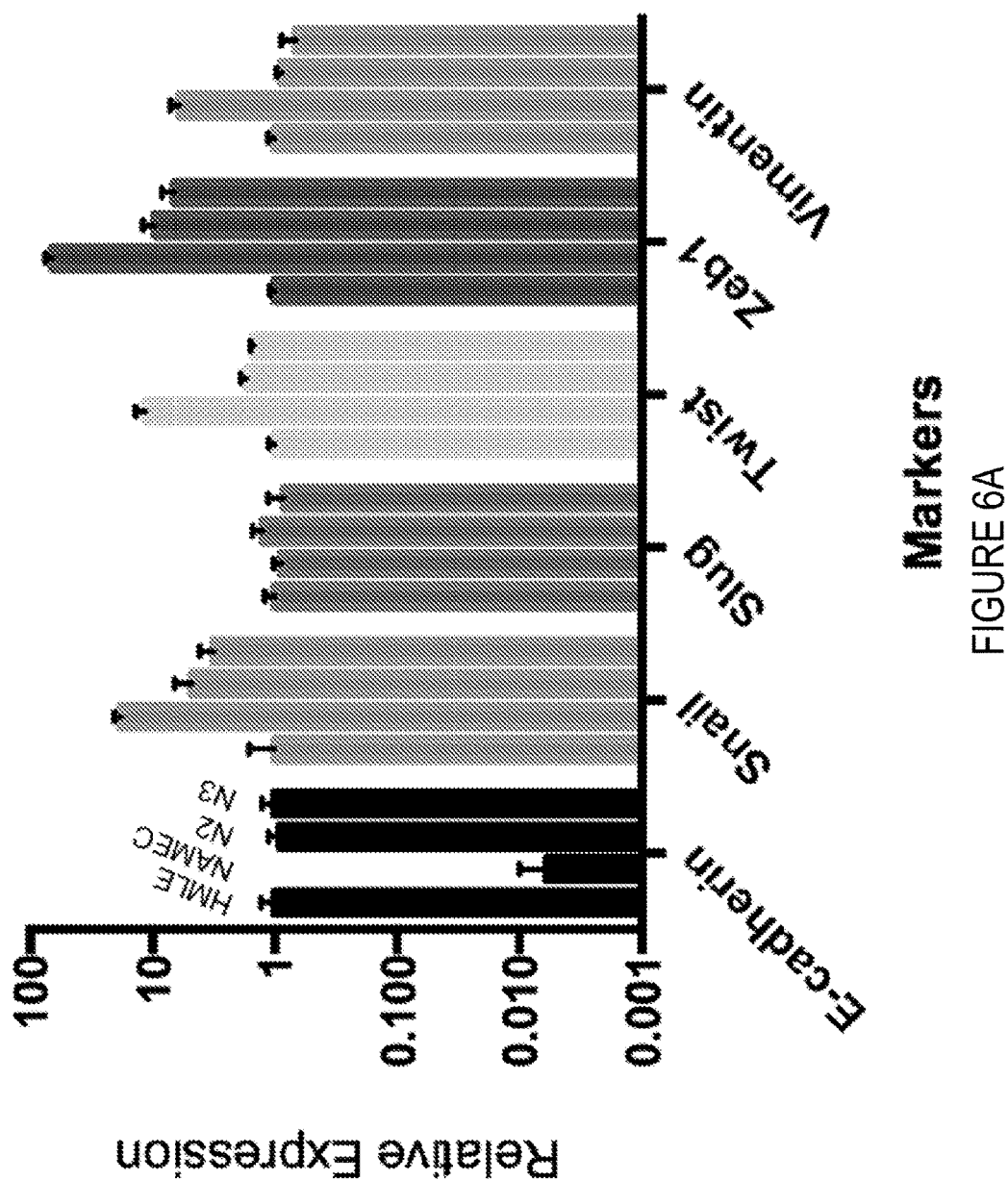

Transcriptional analysis of mesenchymal markers revealed a 5-fold down-regulation of mRNA levels of Vimentin, Fibronectin and N-cadherin, a decrease in expression of Snail and Twist by 10-fold, and Zeb1 by 5-fold, as well as a 100-fold increase in expression levels of E-cadherin (FIG. 6A), further confirming the cells had undergone MET.

The ability of NAMEC cells treated with cholera toxin or forskolin to exhibit CSC characteristics was further evaluated using Boyden chamber assays. Following treatment with either cholera toxin or forskolin, NAMEC cells exhibited a loss of migratory and invasive properties (FIGS. 6B and 6C). Either treatment also resulted in a complete loss of mammosphere-forming ability upon reversion, indicating a loss of the stem-like properties of the NAMEC cells (FIG. 6D).

Figure 7:
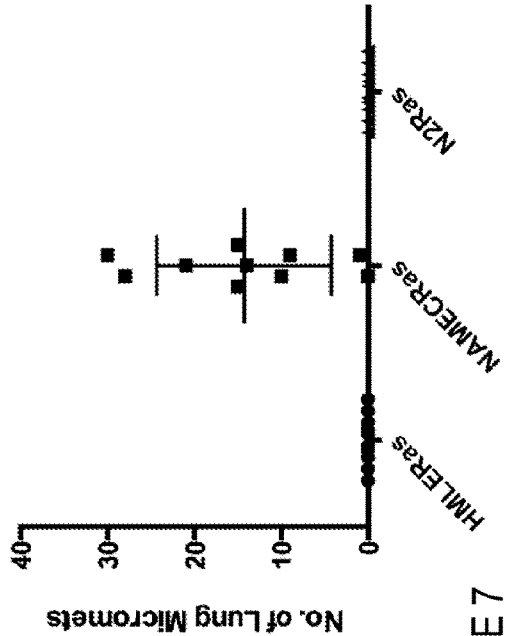
FIGS. 7A-7C show that NAMEC cells that have been induced to undergo a mesenchymal to epithelial transition lose their tumorigenic ability.
Figure 7:
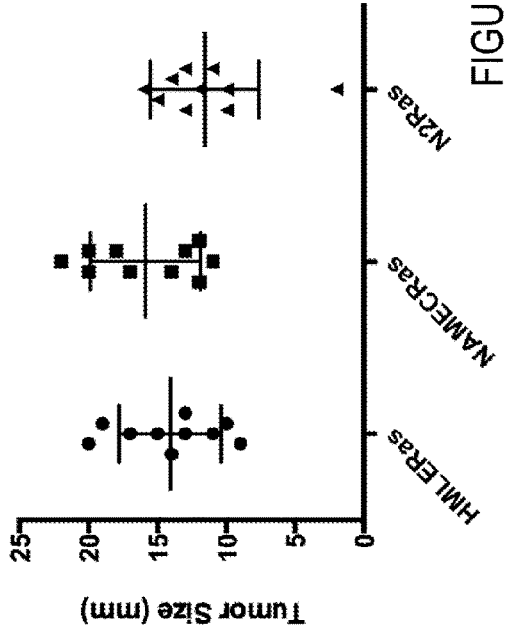

HMLE cells, NAMEC cells, and NAMEC cells treated with cholera toxin were transformed with Ras then xenografted into NOD/SCID mouse mammary fat pads. The NAMEC cells that had been treated with cholera toxin to undergo MET had a surprising 100-fold loss of tumor-initiating ability and a complete loss of micrometastatic foci seeded in the lungs, compared to untreated NAMEC cells, despite that both treated and untreated NAMEC cells resulted in similar overall primary tumor size (FIGS. 7A-7C).

Figure 8:
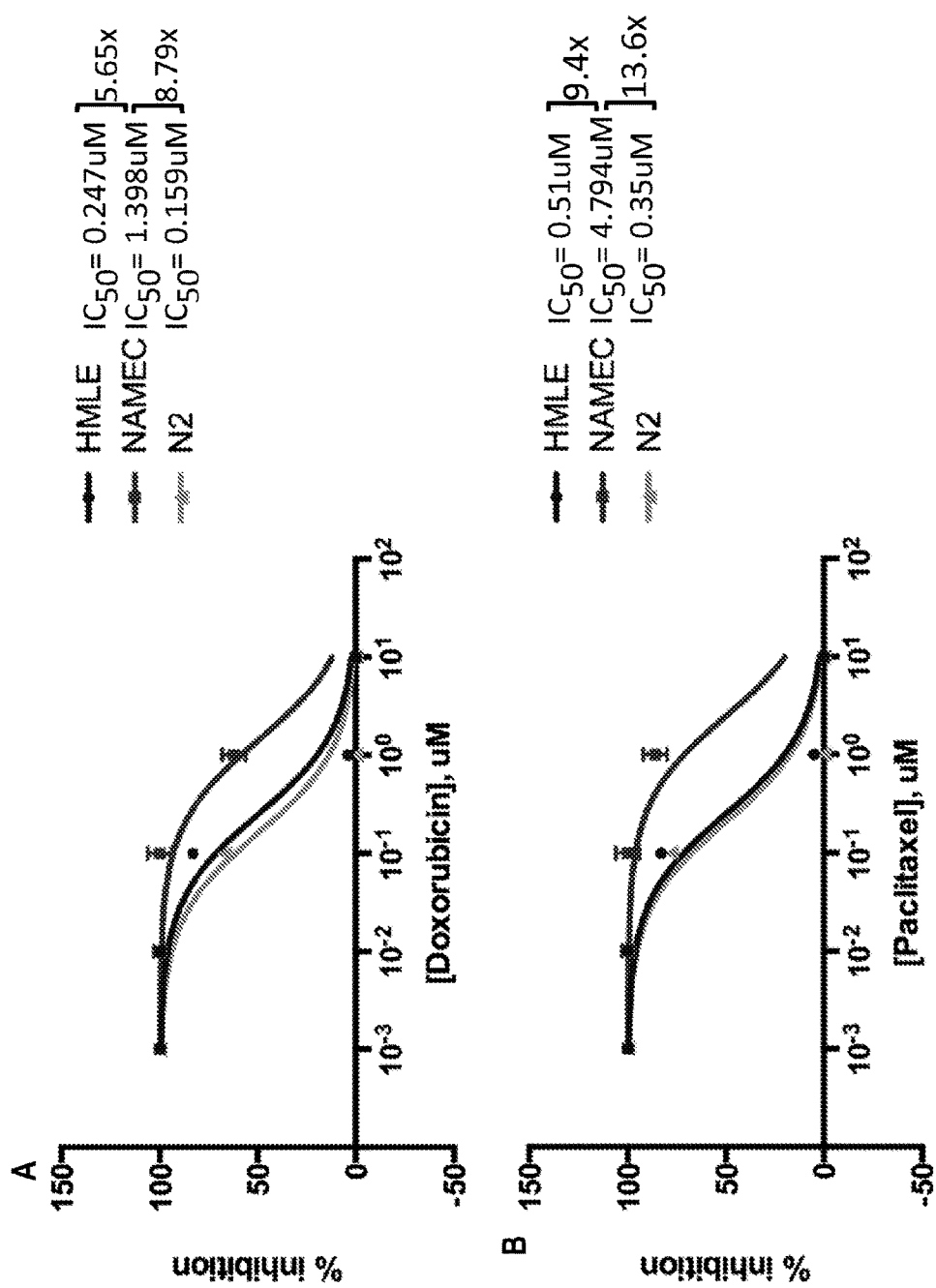
FIGS. 8A and 8B show dose response curves and calculated $IC_{50}$ values for HMLE, NAMEC and NAMEC cells treated with cholera toxin following exposure to a range in concentration of the chemotherapeutic drugs doxorubicin (A) and paclitaxel (B). Induction of a mesenchymal to epithelial transition in NAMEC cells by cholera toxin treatment renders the cells more susceptible to commonly used chemotherapeutic agents both such as doxorubicin and paclitaxel.

NAMEC cells that had been treated with cholera toxin were also evaluated for their susceptibility to chemotherapeutic drugs. As described above, the high level of resistance to conventional chemotherapeutic drugs is one of the primary reasons for the difficulty in eliminating cancer stems cells. As demonstrated in the dose response curves in FIGS. 8A and 8B, HMLE cells were susceptible to inhibition by doxorubicin and paclitaxel, whereas NAMEC cells were highly resistant to both drugs. In contrast to untreated NAMEC cells, NAMEC cells that were treated with cholera toxin had become more susceptible to inhibition by both doxorubicin and paclitaxel (FIGS. 8A and 8B).

Figure 9:
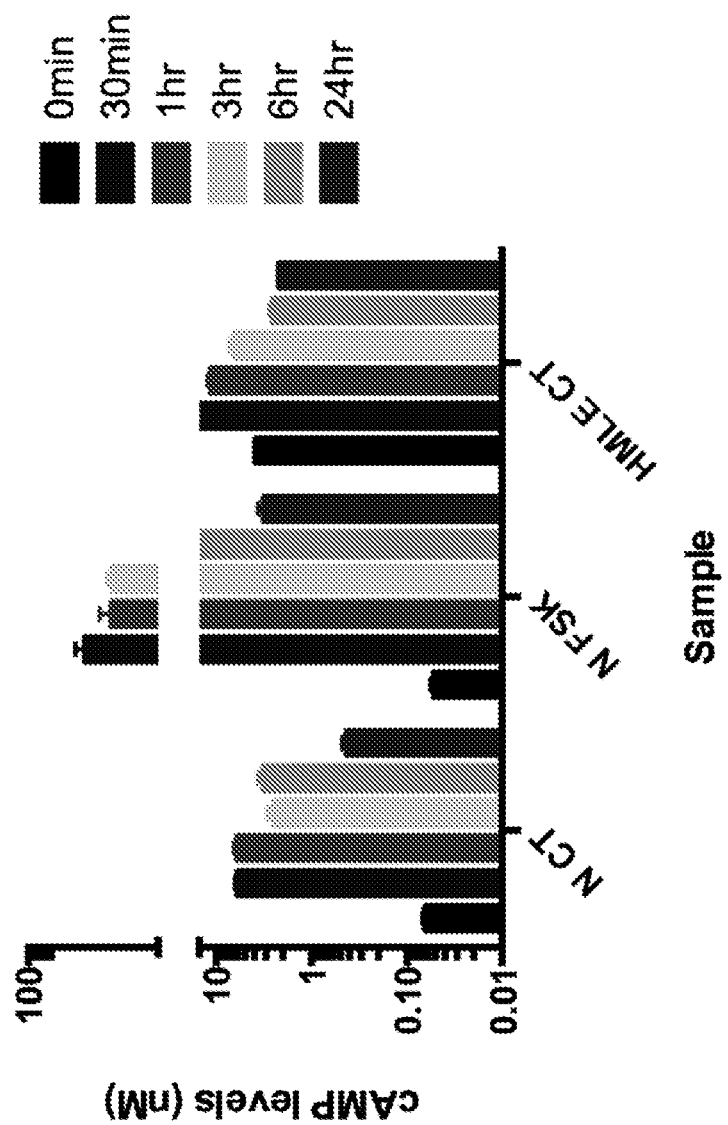
FIG. 9 presents intracellular cAMP levels (nM) in HMLE cells or NAMEC (N) cells that have been treated with cholera toxin (CT) or forskolin (FSK). Both these agents induce an increase in intracellular cAMP levels. For each sample, columns are 0 mins, 30 mins, 1 hr, 3 hr, 6 hr, and 24 hr, from left to right.

To further validate that treatment of NAMEC cells with cholera toxin and forskolin did affect intracellular cAMP levels, cAMP concentrations were assessed in NAMEC and HMLE cells treated with cholera toxin or forskolin over the course of 24 hours. As predicted, both cholera toxin and forskolin independently elevated the intracellular cAMP concentration in NAMEC cells to at least that of HMLE cells (FIG. 9).

In sum, these results indicated that factors that activate adenylate cyclase in mesenchymal cells induce the cells to revert toward the epithelial state, as well as reduce the tumor-initiating and metastatic capacities of the cells. Furthermore, the increased adenylate cyclase activity also resulted in susceptibility to chemotherapeutic drugs that had been ineffective in inhibiting untreated NAMEC cells.

Example 3: Characterization of the Role of Protein Kinase A (PKA) in Regulating the Epithelial State Two of the primary cellular targets of cAMP are Protein Kinase A (PKA), a holoenzyme that is able to phosphorylate a wide range of substrates regulating various cellular and metabolic processes, and Exchange Proteins Activated by cAMP (EPAC). To test which downstream pathway was involved in stimulating the MET, NAMEC cells were treated with 8-Br-cAMP, a cAMP analog that specifically activates PKA, or 8-CPT-2Me-cAMP, a cAMP analog that specifically activates EPACs. Following treatment for 12 days, only the NAMEC cells that had been treated with 8-Br-cAMP, and not the cells that had been treated with 8-CPT-2Me-cAMP, displayed epithelial morphologies (data not shown), indicating that PKA was the primary target of cAMP involved in stimulating the transition.

Figure 10:
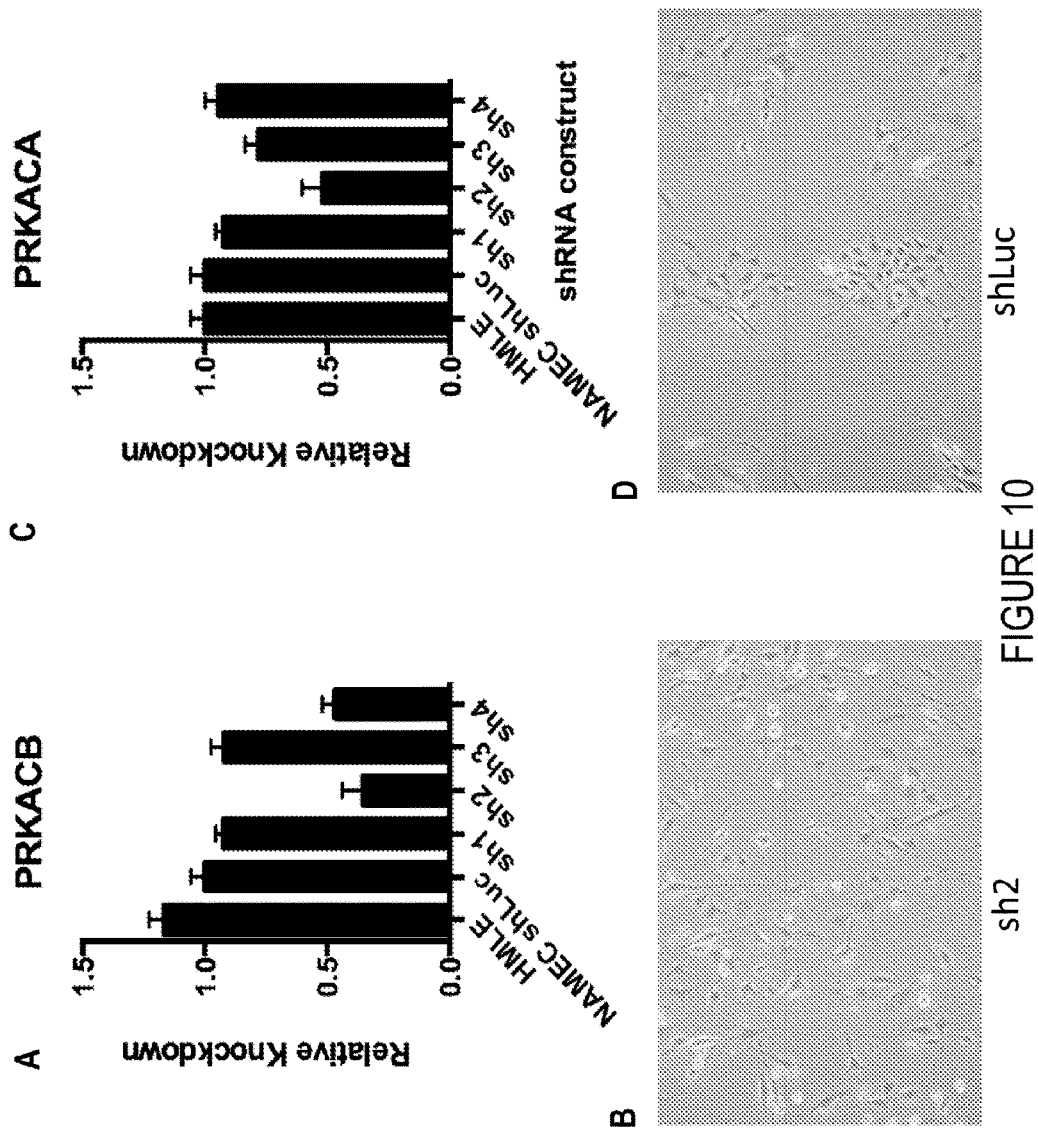
FIGS. 10A-10D show that knockdown of PKA subunits abrogates the ability of cholera toxin to induce a mesenchymal to epithelial transition of NAMEC cells.

To further confirm the role of PKA in the MET, PKACB and PKACA, the catalytic subunits of PKA, were knocked down using shRNA constructs (FIGS. 10A and 10C). The PKACB/PKACA knockdown achieved using shRNA construct 2 (sh2) prevented MET induction in NAMEC cells treated with cholera toxin compared to control constructs (shLuc) (FIGS. 10B and 10D). These results indicated a critical role for PKA in the maintenance of the epithelial state.

Figure 11:
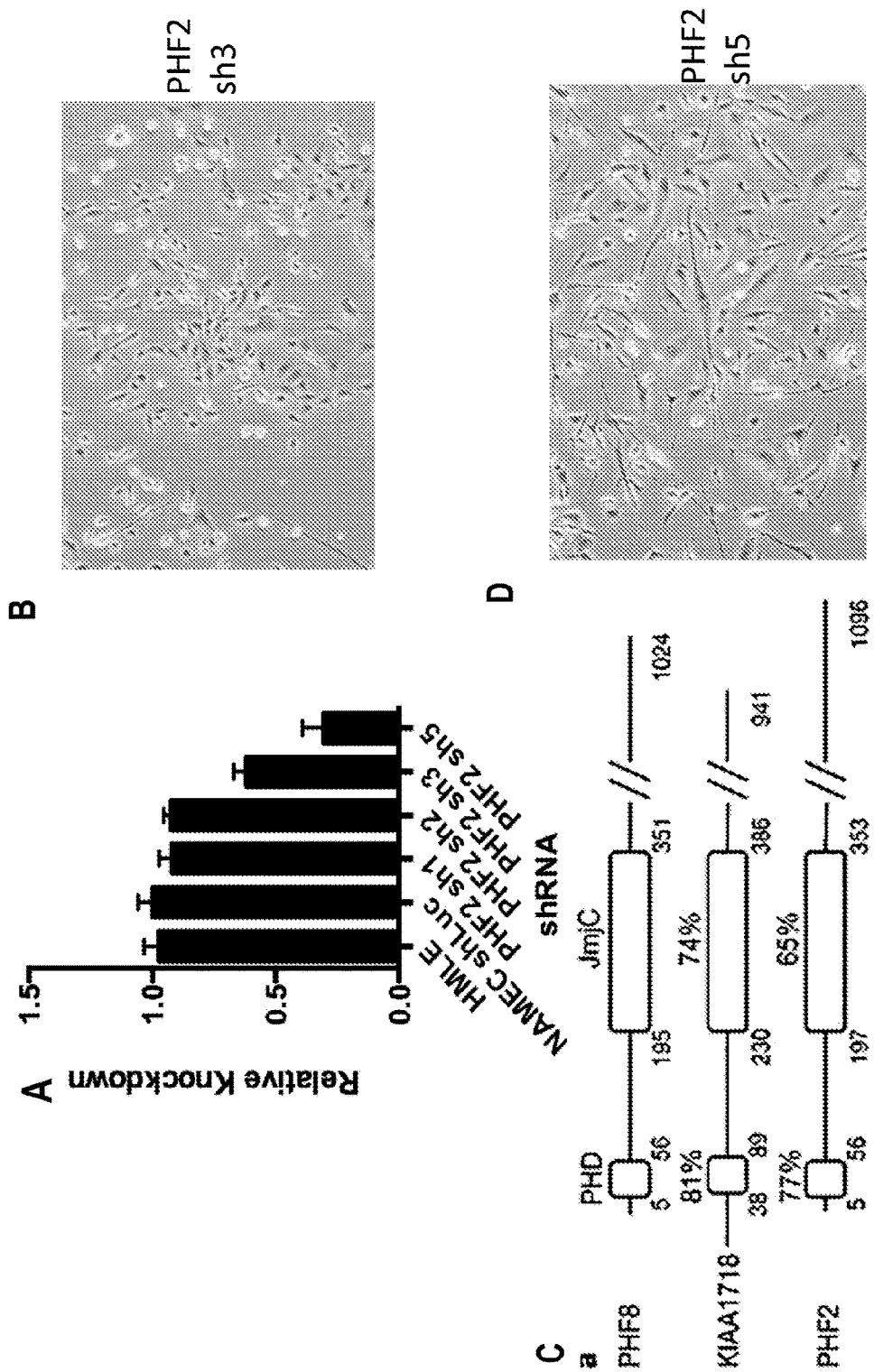
FIGS. 11A-11D show knockdown of PHF2 abrogates the ability of cholera toxin to induce a mesenchymal to epithelial transition of NAMEC cells.
Figures 12A, 12B:
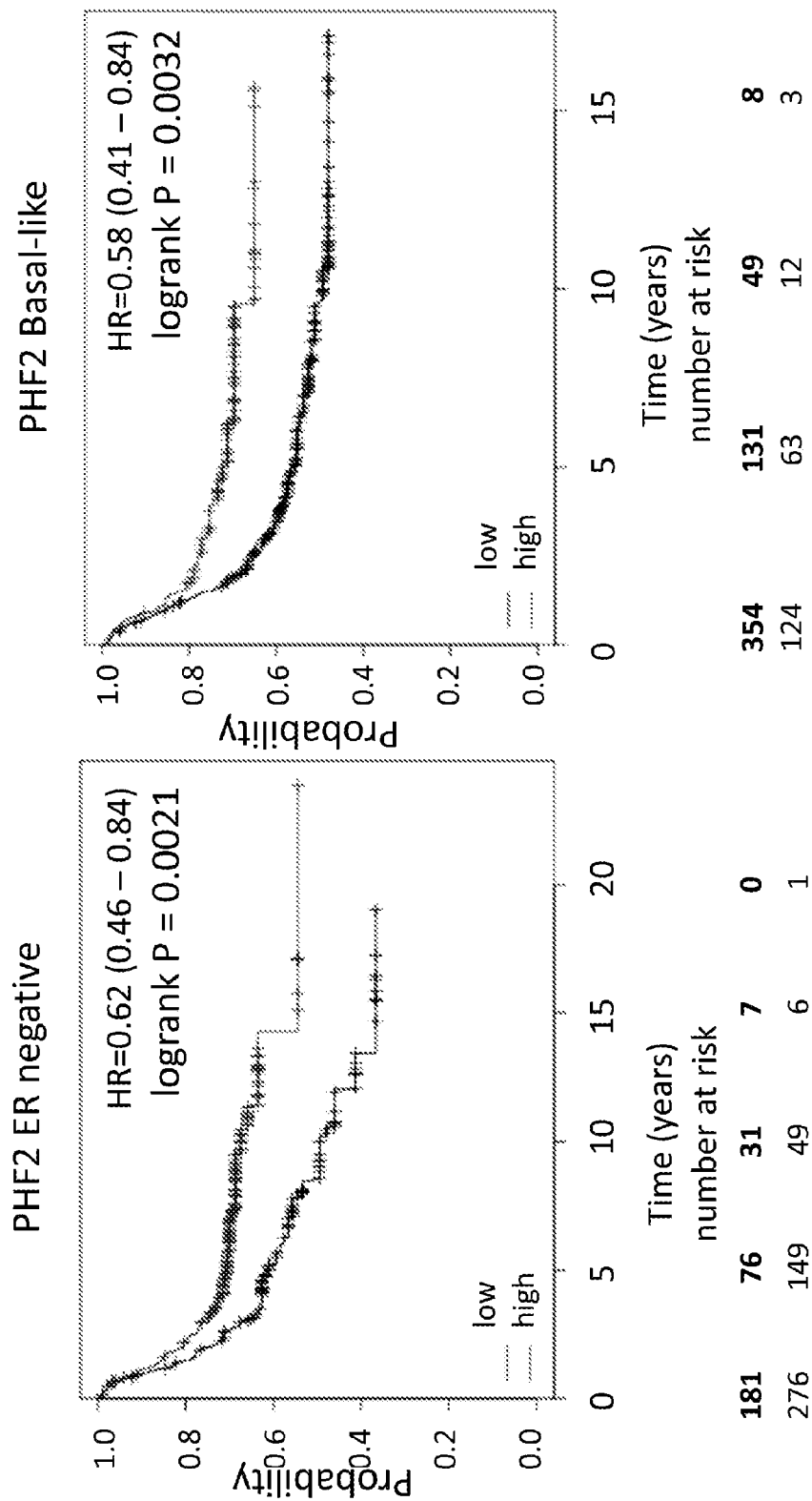
FIGS. 12A-12F show PHF2 and PRKACA/B used to stratify basal-like breast cancer and ER-negative breast cancer patients. Patients that exhibit higher expression of PHF2, PRKACA, or both proteins have a better relapse-free survival. Black lines depict low expression and gray lines depict high expression of the indicated protein.
Figure 12D:
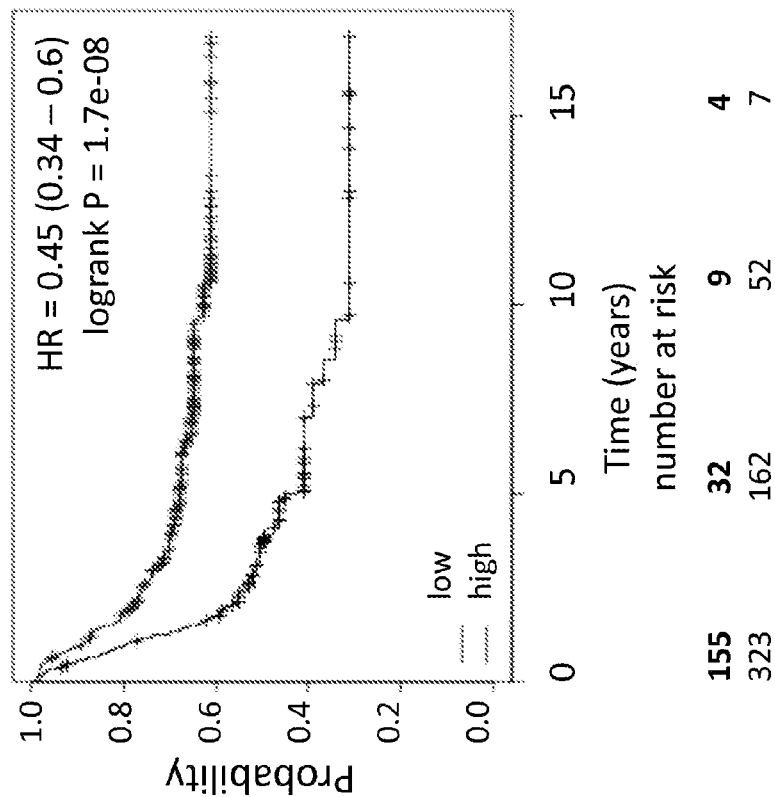
Figure 12C:
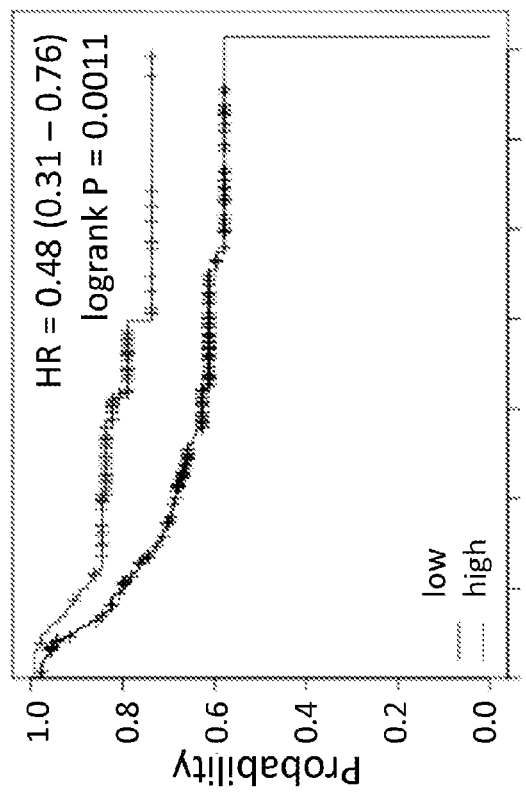
Figures 12E, 12F:
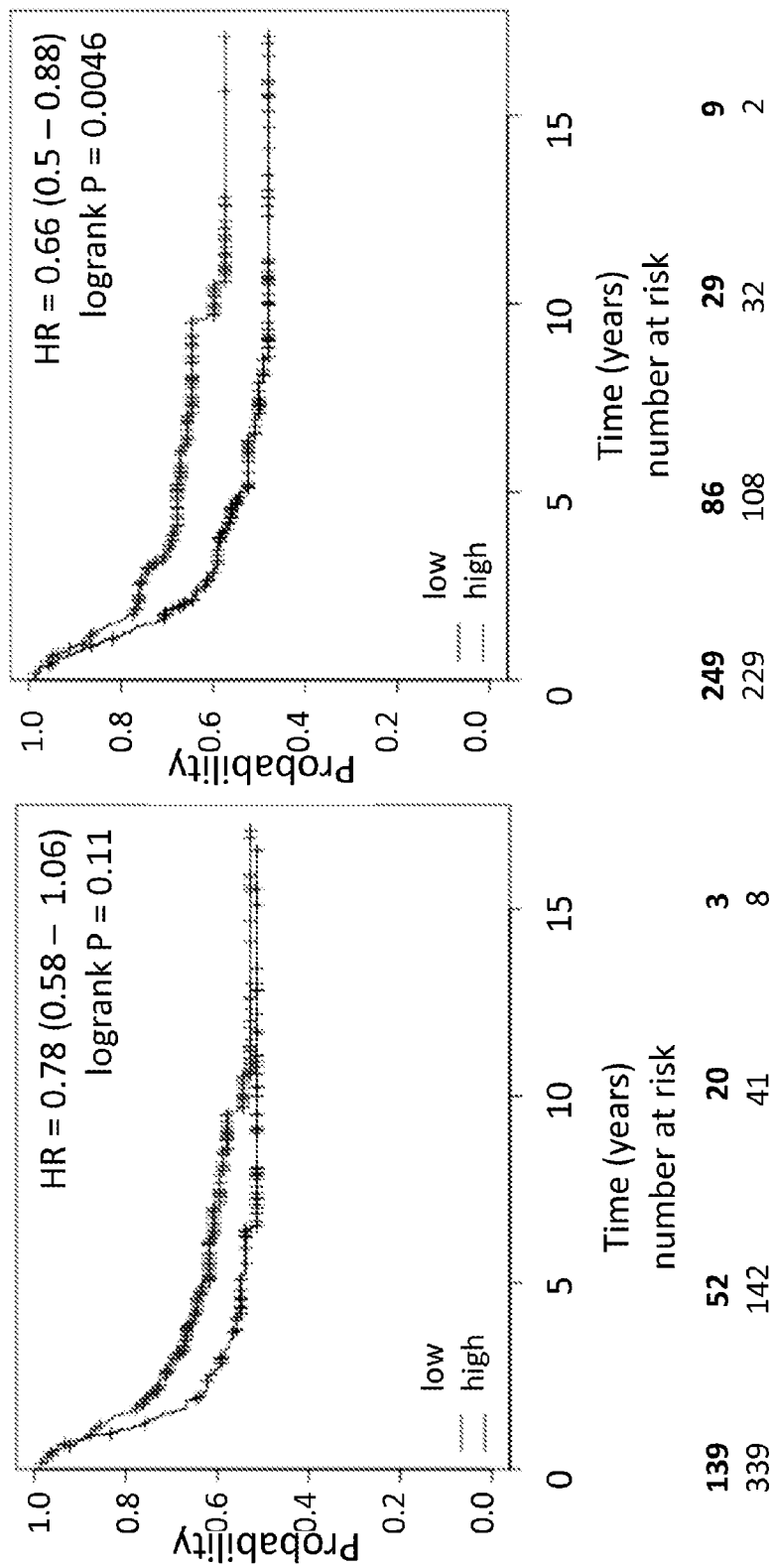
Figure 13:
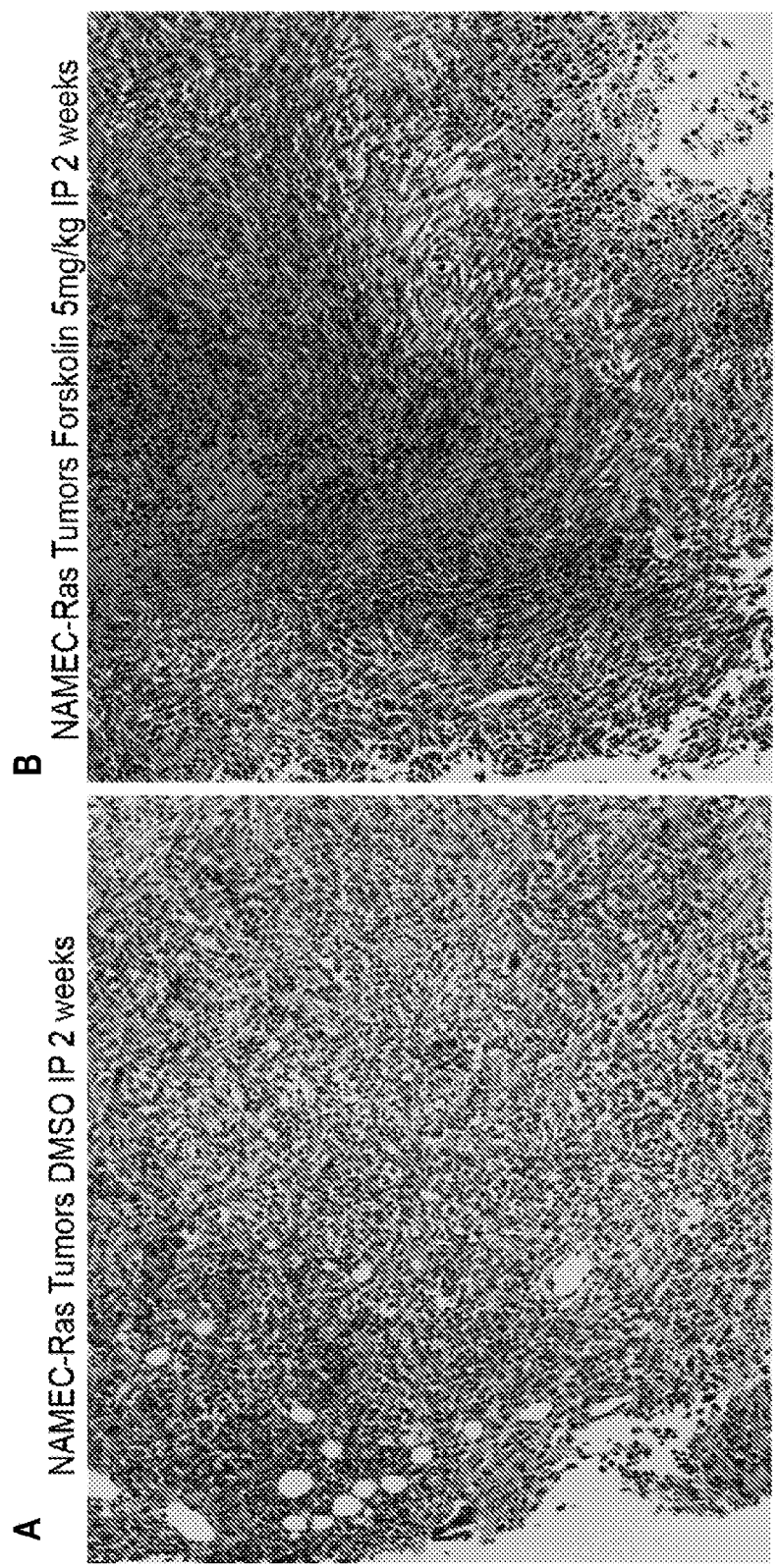
FIGS. 13A and 13B show representative micrographs of hematoxylin and eosin-stained NAMEC-Ras tumors in vivo.

PHF2, a histone lysine demethylase that demethylates the H3K9me2 repressive histone, has been identified as a substrate of PKA. To evaluate whether PHF2 also played a role in the MET, it was knocked down using shRNA constructs (FIG. 11A). Similar to knockdown of the PKA subunits, shRNA-mediated knockdown of PHF2 also prevented the MET transition in NAMEC cells treated with cholera toxin (FIGS. 11B and 11D).

Based on the confirmed roles of PKA and its substrate PHF2 in the MET, monitoring expression or activity of these molecules can be used to predict relapse-free survival of patients with basal-like breast cancer and ER-negative breast cancer. As shown in FIGS. 12A-12F, increased expression of PHF2, PRKACA and PRKACB correlated with an increased probability of survival.

Example 4: Evaluation of cAMP-Elevating Agents in Combination with Chemotherapy

The chemosensitivity of the cells that have undergone an MET are tested by cell proliferation assays using CyQuant Dye (Invitrogen) to accurately assay cell numbers and apoptosis assays using Annexin V staining and FACS with a dead-cell discriminator such as DAPI. Dose response curves are generated from these assays using the following strategies:

i) Doxorubicin or Paclitaxel treatment of HMLE and NAMEC cells to compare the differences in sensitivities of NAMEC cells and the reverted NAMECs (N2) to doxorubicin and paclitaxel. These assays allow calculation of the IC50 of the chemotherapeutic agents that can be used as a control for further experiments.

ii) Doxorubicin or Paclitaxel treatment on NAMEC cells that have previously been reverted using forskolin or cholera toxin.

iii) Doxorubicin or Paclitaxel treatment of NAMEC cells in combination with forskolin or cholera toxin on NAMEC cells before reversion. This allow evaluation of the effects of combining forskolin or cholera toxin with the two chosen chemotherapeutics.

The assays are also carried out using colforsin daropate (CD), a water-soluble form of forskolin.

In Vivo Toxicity of cAMP-Elevating Agents

The in vivo toxicity of cAMP-elevating agents are also tested. cAMP-elevating agents are tested in non-tumor-bearing mice to ensure that doses used do not elicit undesired side-effects on normal tissues.

Dose escalation studies are carried out on NOD/SCID mice to test the maximum tolerated dose (MTD) that the animals can withstand without undesired side-effects. Forskolin (Fsk) has been previously tested in vivo in mice, providing an indication of doses that are appropriate to use without toxicities at 5 mg/kg with no reported side-effects. The water-soluble derivate of forskolin, colforsin daropate (CD), has also been tested in animals. To test whether this dose of forskolin/CD is sufficient to induce an increase in the levels of cAMP in the neoplastic cells within growing tumors, mice bearing NAMEC-Ras tumors are treated with 5 mg/kg forskolin intra-peritoneally (IP) and harvest the tumors 1 hr, 6 hrs and 24 hrs following treatment. Tumors sections are stained with PKA antibodies. Immunofluorescence images are used to monitor nuclear localization of PKA, a measure of its activated state. These experiments enable assessment of the pharmacodynamics of forskolin and CD and the in vivo doses required to achieve sufficient elevation of cAMP to induce the MET.

In one example of gauging effects of cAMP-elevating treatments on normal tissues, the effect of forskolin is tested on the normal mammary stem-cell-repopulating ability. Following in vivo administration of forskolin for 2 weeks, MaSCs from mammary glands of 8-week old virgin mice are sorted using markers such as CD61 and CD49f, and tested subsequently for their ability to repopulate, in limiting dilutions, entire mammary glands upon transplantation into syngeneic recipient mice with cleared mammary stromal fat pads. Additionally, the effects of forskolin treatment on the stem cells of vital organs such as the hematopoietic stem cell (HSC) and intestinal stem cell (ISC) are also assessed. In particular, the frequencies of HSCs are tested by isolating bone marrow from forskolin-treated and untreated mice and quantifying the number of CD150+CD48-Sca-1+Lineage-c-kit+ cells by flow cytometry. Similarly, the ISC frequency is tested by isolation of intestinal crypts and quantitation of Lgr5-positive cells. These results indicate the extent to which administration of forskolin has side-effects on vital organs that lead to unacceptable levels of systemic toxicity.

In Vivo Administration of MET-Inducers to NAMEC-Ras Tumors in NOD/SCID Mice

NOD/SCID mice bearing two-month old tumors (1 cm diameter) from xenotransplanted NAMEC-Ras cells are subjected to daily treatment with forskolin. At this stage the NAMEC-Ras primary tumors are capable of forming lung metastases. This treatment allows a determination of the extent to which forskolin induces regression of primary tumors following loss of stemness, even when the cells are at a stage where they have begun spawning metastases (as may often be the case with diagnosed primary breast cancers in the oncology clinic).

Following treatment for two weeks with forskolin:

a. The weight and size of the primary tumor are measured.
b. The primary tumors are resected, digested and analyzed by FACS using CD44 and CD24 markers to observe whether the tumors have lost their CSC subpopulations (CD44hiCD24lo) and moved via intermediate states (CD44hiCD24hi) to a largely epithelial (CD44loCD24hi) state.
c. RNA from the primary tumor is analyzed for expression of epithelial and mesenchymal markers.
d. The metastatic burden is estimated by enumerating the metastatic foci present in the lungs.
e. Cells from these treated tumors are analyzed for tumor-initiating ability by limiting-dilution analyses at dilutions of 106, 105, 104 and 103 cells implanted orthotopically in mammary fat pads of recipient mice.

All these parameters are compared to control untreated mice to determine the effects of treatment with forskolin. This establishes the extent to which MET occurs in vivo with the systemic administration of cAMP-elevating agents.

In Vivo Administration of cAMP-Elevating Agents and Chemotherapeutic Agents to Mice Bearing NAMEC Tumors The assays described above are performed with a combination of forskolin and a chemotherapeutic agent (e.g. doxorubicin or paclitaxel). The NAMEC-Ras tumors are treated with doxorubicin at 2 mg/kg or paclitaxel at 20 mg/kg daily, two of the most commonly used chemotherapeutic agents in the treatment of breast cancer patients in the clinic. This will determine the ability of the cAMP-elevating agents to act synergistically with cytotoxic drugs to ensure complete regression of the primary tumor and the effects of such treatments on the metastatic burden of experimental animals.

Expansion of In Vivo Testing to Different Basal-Like Breast Cancer Xenograft Tumor Additional basal-like breast cancer cell lines, for example cells of the SUM159, Hs578T and MDA-MB-468 human breast cancer lines are implanted in mouse hosts, allowed to grow up to 1 cm size, and subjected to treatment with cAMP-elevating agents and chemotherapeutic agents as described above with the NAMEC-Ras cells. Combination treatments are performed for 7 days, following which tumors are profiled for surviving CSCs. Further experiments determine the extent of efficacy of the combination cAMP-elevating agent with a chemotherapeutic agent in treatment of primary basal-like breast cancer samples.

Example 5: Treatment of NAMEC-Ras Tumors with Forskolin In Vivo

Ras-transformed NAMEC cells were transplanted into NOD/SCID mice and allowed to grow for 6 weeks at which time the mice were treated with either DMSO (control) or forskolin at 5 mg/kg daily intraperitoneally. Following treatment for 2 weeks, tumors were harvested from the mice for analysis. Tumor sections were observed after hematoxylin and eosin (H&E) staining.

Tumors isolated from mice that were treated with DMSO were poorly differentiated and displayed characteristic aggressive, sarcoma-like features. In contrast, tumors isolated from mice that had been treated with forskolin showed higher levels of necrosis, regions containing more differentiation, and carcinoma-like properties with very few sarcomatoid regions remaining. These results indicate that treatment with forskolin could be inducing in vivo differentiation of the mesenchymal NAMEC-Ras tumors.

Example 6: Activation of PKA in NAMEC-Ras Tumors In Vivo

Figure 14A:
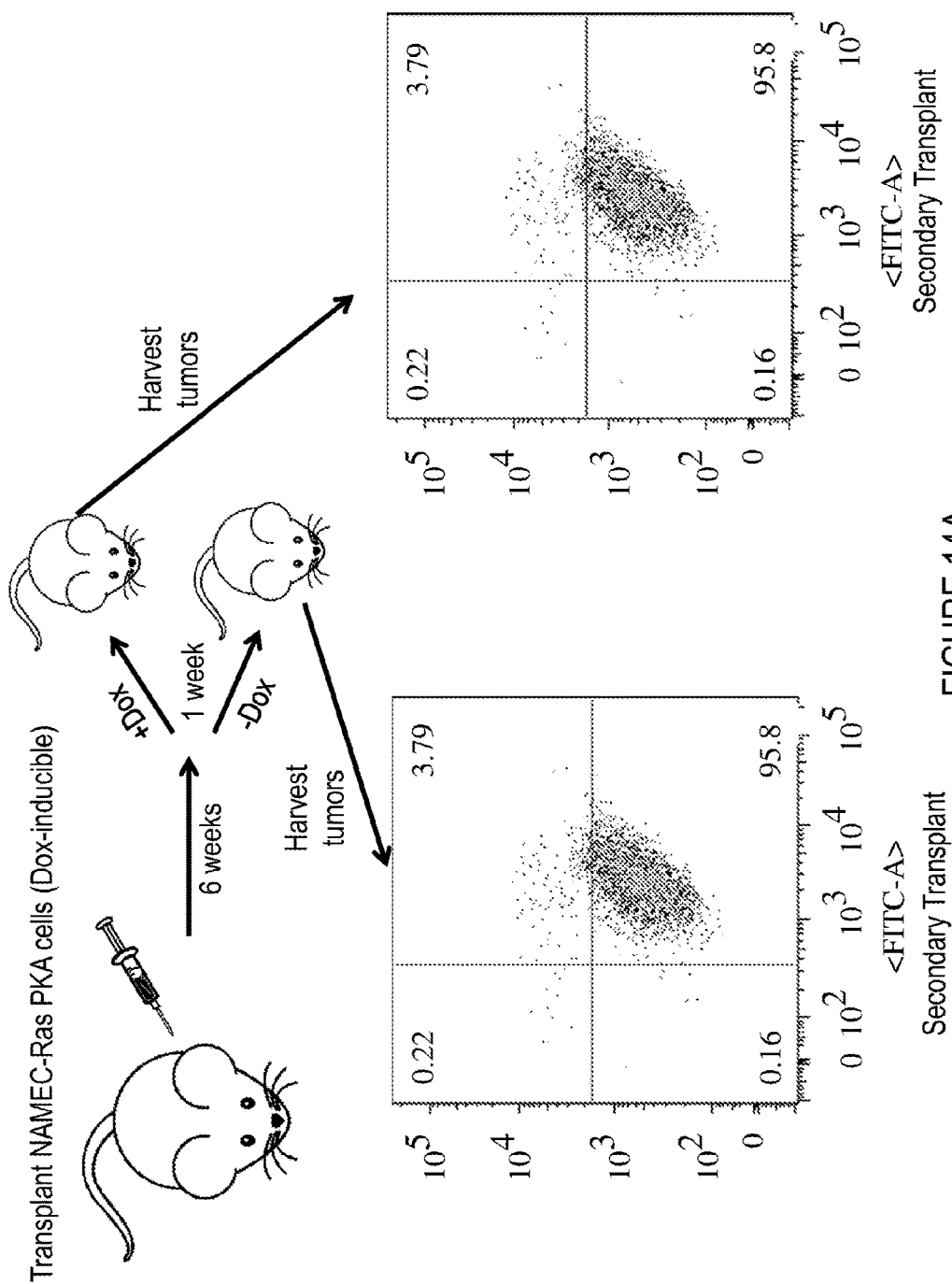

As presented schematically in FIG. 14A, active PKA was expressed in Ras-transformed NAMEC cells from a doxycycline-inducible vector, and cells were transplanted into NOD/SCID mice. After 6 weeks and once palpable tumor masses were observed, one group of mice was treated for 1 week with doxycycline in the drinking water (+Dox), whereas the other group did not receive doxycycline (−Dox). Following treatment, the tumors were harvested from the mice, digested and analyzed by FACS using CD44 and CD24 markers to observe whether the tumors had lost their CSC properties. The cells were then transplanted into secondary recipients at limiting dilutions.

Figure 14D:
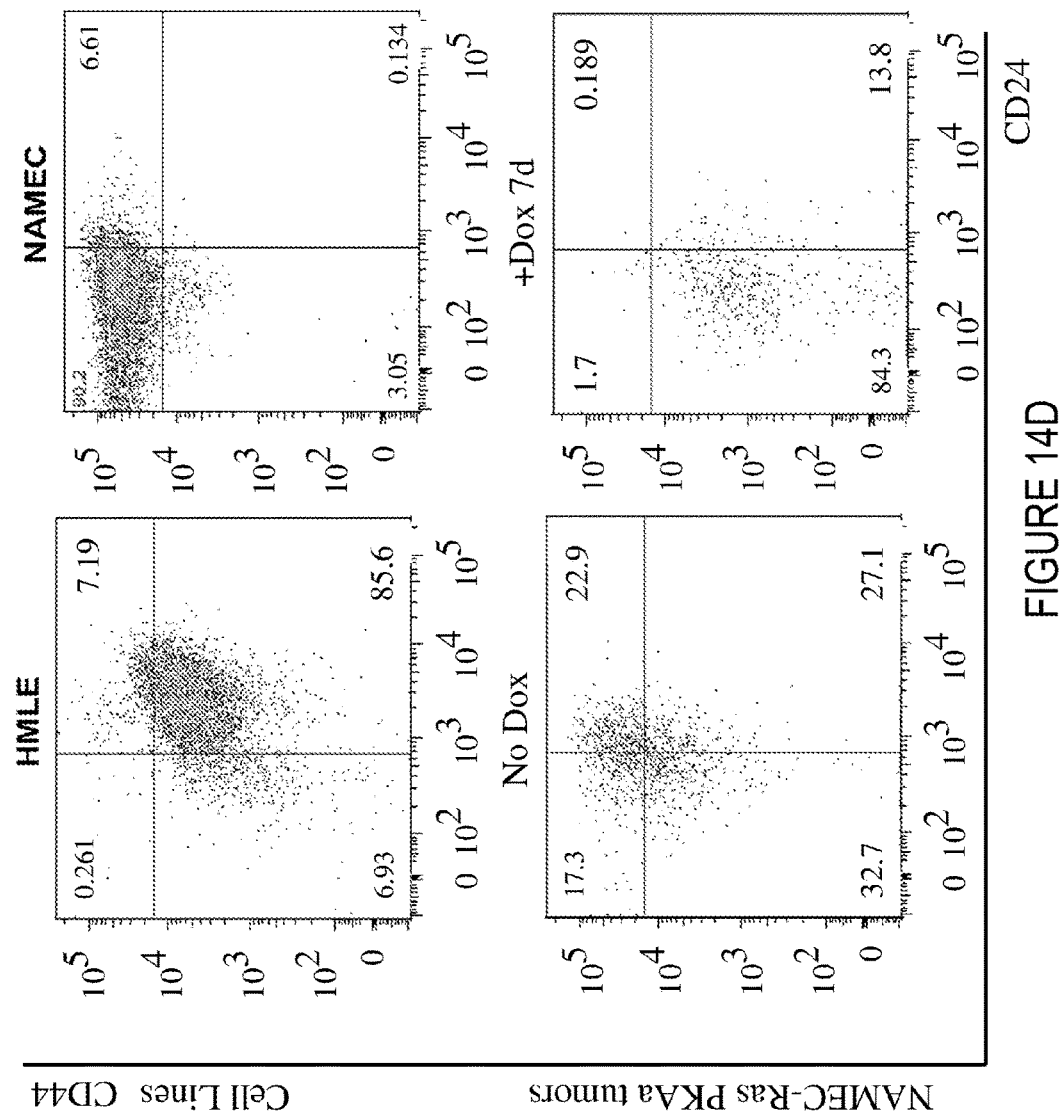

Cells isolated from mice that received doxycycline (and therefore induced PKA) showed a loss of CD44, indicating a loss of CSC properties as compared to cells isolated from that did not receive doxycycline (and therefore did not induce PKA)(FIG. 14D). Upon secondary transplantation, cells isolated from mice that received doxycycline (NAMEC-Ras PKAa+Dox) had reduced tumor initiating ability as compared to cells isolated from mice that did not receive doxycycline (NAMEC-Ras PKAa no Dox) (FIG. 14E).

The mice were further assessed for tumor volume and number of lung metastases following secondary transplantation. Although there was no significant change in tumor volume between the groups of mice (FIG. 14B), the number of lung micrometastases that could be seeded by cells that were isolated from mice treated with doxycycline were reduced compared to cells that were isolated from mice that did not receive doxycycline (FIG. 14C).

In sum, these results indicate that expression of active PKA in Ras-transformed tumor cells leads to a reduction in CSC properties including loss of CD44 expression and tumor-initiating ability.

Having thus described several aspects of at least one embodiment of this disclosure, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only. All references described herein are incorporated by reference for the purposes described herein.

Moreover, this disclosure is not limited in its application to the details of construct and arrangement of components set forth in the disclosed description or illustrated in the drawings. The disclosure is capable of other embodiments and of being practiced or of being carried out in various ways. Also, the phraseology and terminology used herein is for the purposed of description an should not be regarded as limiting. The use of "including," "comprising," or "having," "containing," "involving," and variations thereof herein, is meant to encompass the items listed thereafter and equivalents thereof as well as additional items.

This disclosure is not limited in its application to the details of construction and the arrangement of components set forth in the description or illustrated in the drawings. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A method of treating a subject having a carcinoma, the method comprising:
    administering to the subject a Protein Kinase A (PKA) pathway activator in an amount sufficient to induce cancer stem cells of the carcinoma to undergo a mesenchymal to epithelial transition;
    wherein the subject is administered the PKA pathway activator within 1 hour, 1 day, 1 week, 1 month or more prior to being administered a chemotherapeutic agent and/or radiotherapy.

2. The method of claim 1, further comprising administering to the subject an effective amount of the chemotherapeutic agent and/or radiotherapy.

3. The method of claim 1, wherein the PKA pathway activator induces adenylyl cyclase activity, thereby increasing cyclic AMP (cAMP) levels in the cells.

4. The method of claim 1, wherein the PKA pathway activator is selected from cholera toxin, forskolin, colforsin daropate (CD) and derivatives of any one of them.

5. The method of claim 1, wherein the chemotherapeutic agent is a DNA intercalating agent or a mitotic inhibitor.

6. The method of claim 5, wherein the mitotic inhibitor comprises paclitaxel, docetaxel, vinblastine, vincristine, and/or vinorelbine.

* * * * *